United States Patent
Diab et al.

(10) Patent No.: US 8,670,814 B2
(45) Date of Patent: Mar. 11, 2014

(54) LOW-NOISE OPTICAL PROBES FOR REDUCING AMBIENT NOISE

(75) Inventors: Mohamed Diab, Ladera Ranch, CA (US); Esmaiel Kiani-Azarbayjany, Laguna Niguel, CA (US); David R. Tobler, Westminster, CO (US); Thomas J. Gerhardt, Littleton, CO (US); Eugene E. Mason, Boulder, CO (US); Mike A. Mills, Golden, CO (US)

(73) Assignee: Masimo Corporation, Irvine, CA (US)

(*) Notice: Subject to any disclaimer, the term of this patent is extended or adjusted under 35 U.S.C. 154(b) by 625 days.

(21) Appl. No.: 12/360,828

(22) Filed: Jan. 27, 2009

(65) Prior Publication Data

US 2009/0143657 A1 Jun. 4, 2009

Related U.S. Application Data

(63) Continuation of application No. 10/957,843, filed on Oct. 4, 2004, now Pat. No. 7,483,730, which is a continuation of application No. 10/260,049, filed on Sep. 27, 2002, now Pat. No. 6,813,511, which is a continuation of application No. 09/898,990, filed on Jul. 3, 2001, now Pat. No. 6,792,300, which is a continuation of application No. 09/094,202, filed on Jun. 9, 1998, now Pat. No. 6,256,523, which is a continuation of application No. 08/543,789, filed on Oct. 16, 1995, now Pat. No. 5,782,757.

(51) Int. Cl.
*A61B 5/1455* (2006.01)

(52) U.S. Cl.
USPC .................................................. 600/344

(58) Field of Classification Search
USPC .................. 600/310, 322, 323, 340, 344
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,425,360 A * | 6/1995 | Nelson | 600/323 |
| 5,431,170 A | 7/1995 | Mathews | |
| D361,840 S | 8/1995 | Savage et al. | |
| 5,437,275 A * | 8/1995 | Amundsen et al. | 600/323 |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |

(Continued)

*Primary Examiner* — Eric Winakur
(74) *Attorney, Agent, or Firm* — Knobbe Martens Olson & Bear LLP

(57) ABSTRACT

An optical probe, which is particularly suited to reduce noise in measurements taken on an easily compressible material, such as a finger, a toe, a forehead, an earlobe, or a lip, measures characteristics of the material. A neonatal and adult disposable embodiment of the probe include adhesive coated surfaces to securely affix the probe onto the patient. In addition, the surface of the probe is specially constructed to reduce the effect of ambient noise.

16 Claims, 34 Drawing Sheets

(56) References Cited

U.S. PATENT DOCUMENTS

| | | |
|---|---|---|
| 5,494,043 A | 2/1996 | O'Sullivan et al. |
| 5,520,177 A * | 5/1996 | Ogawa et al. .......... 600/323 |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Pishney et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |

(56) References Cited

U.S. PATENT DOCUMENTS

| | | |
|---|---|---|
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |

\* cited by examiner

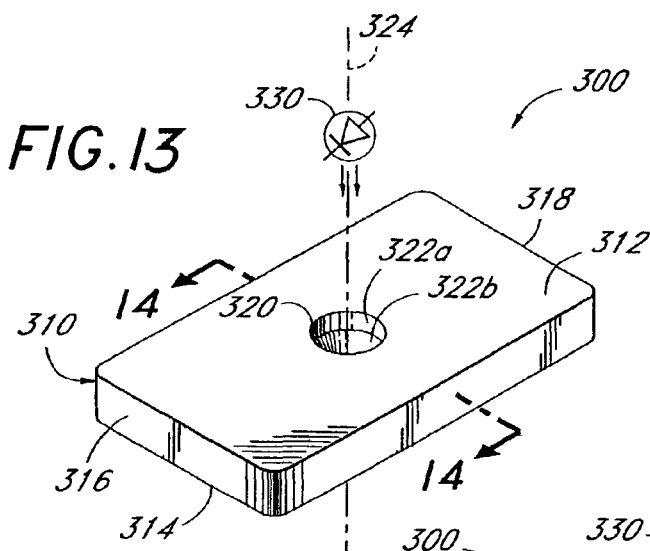
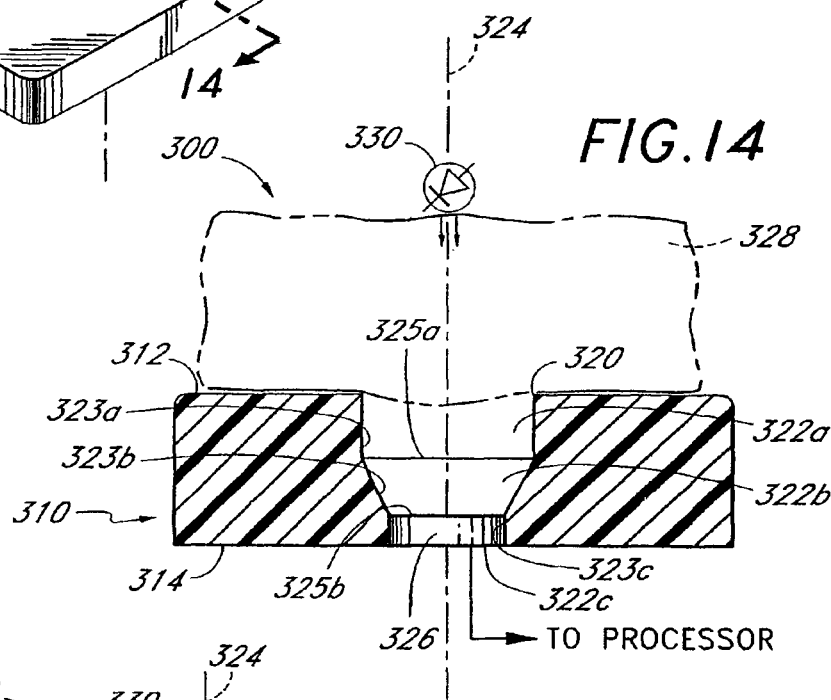
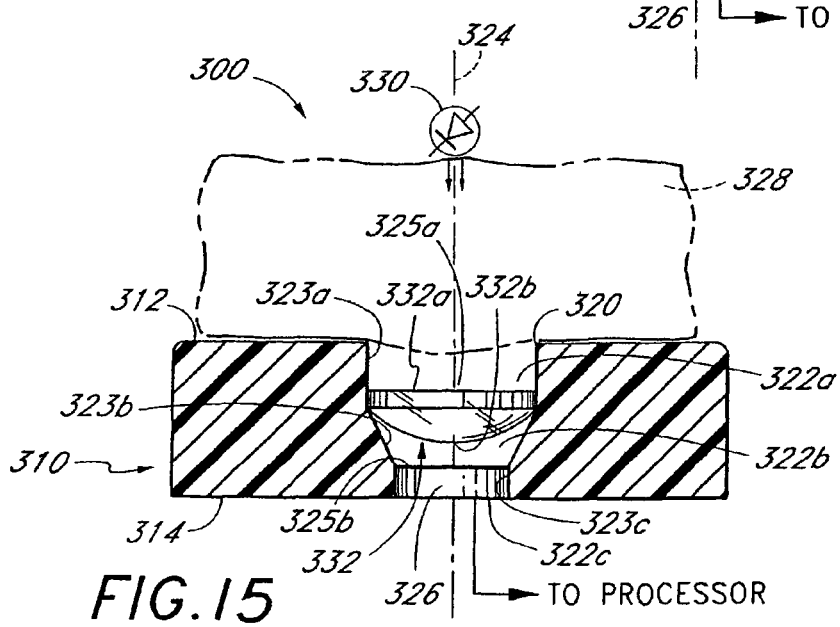

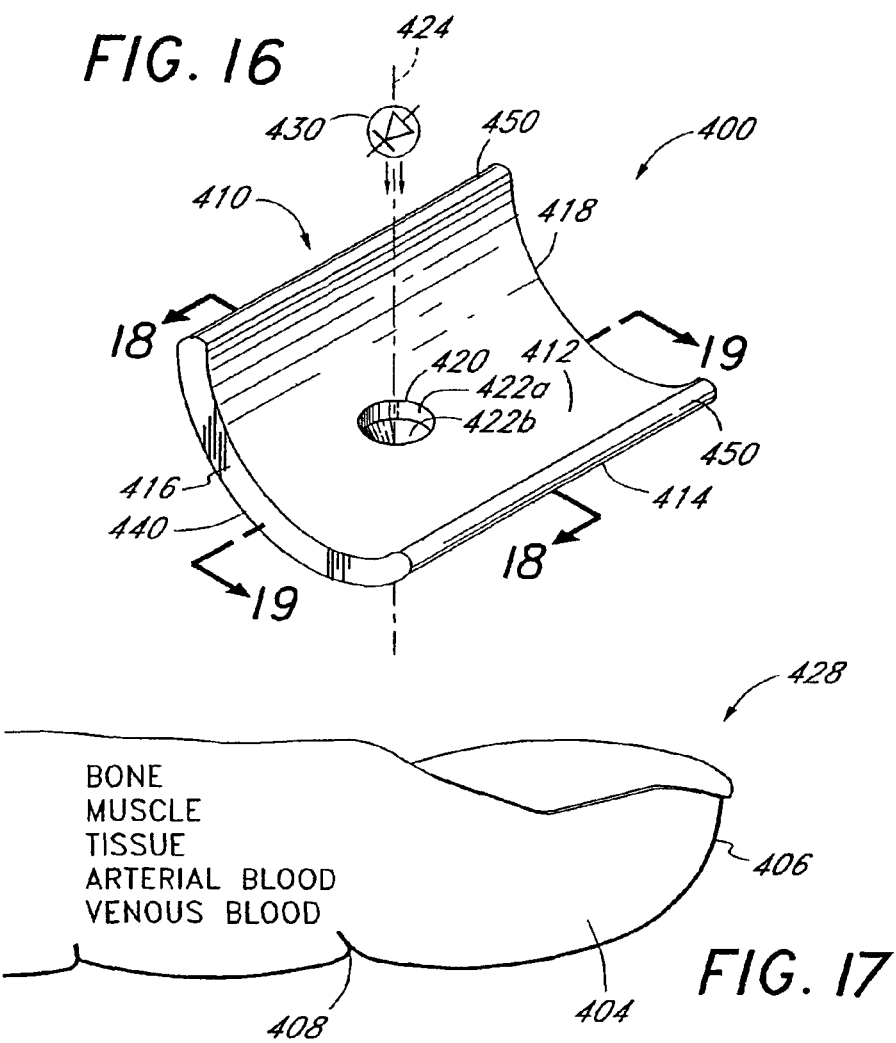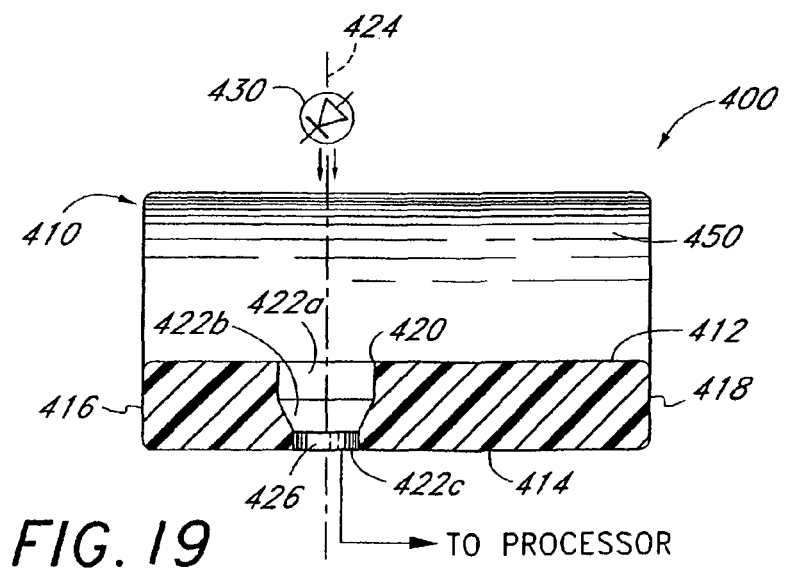

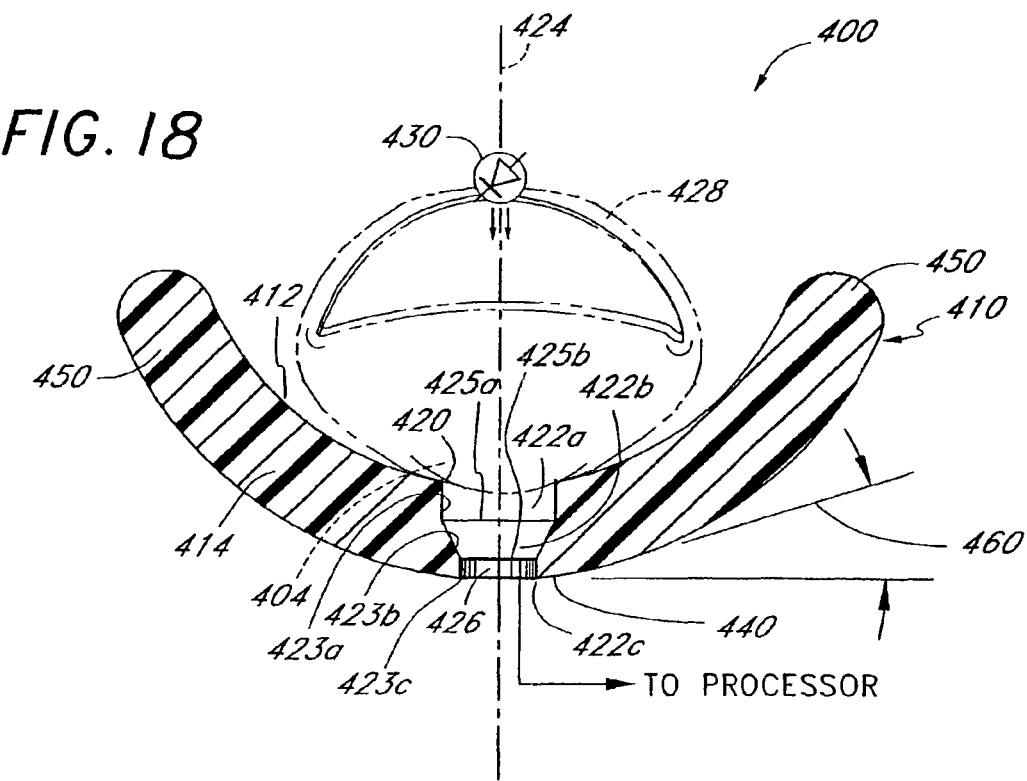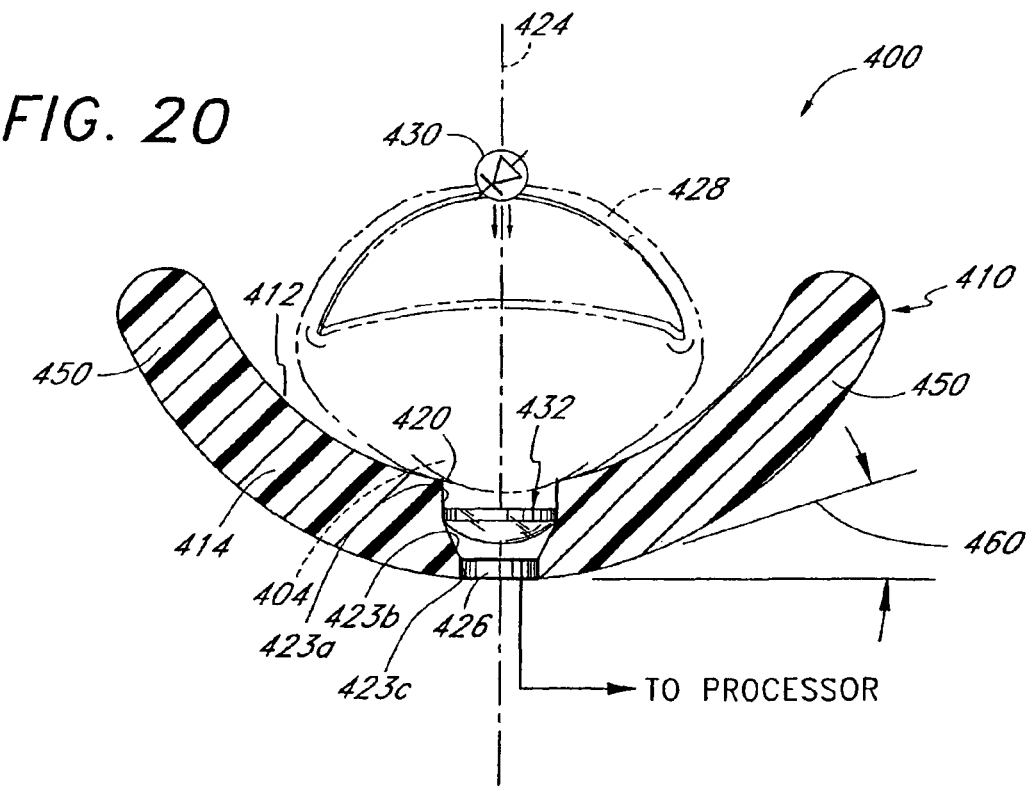

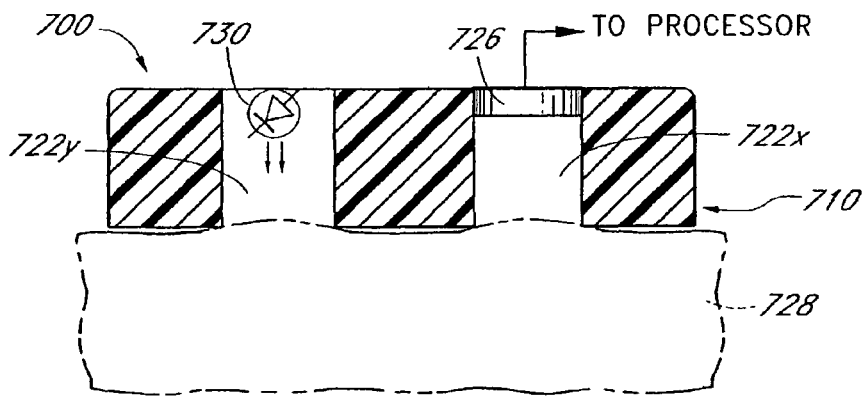
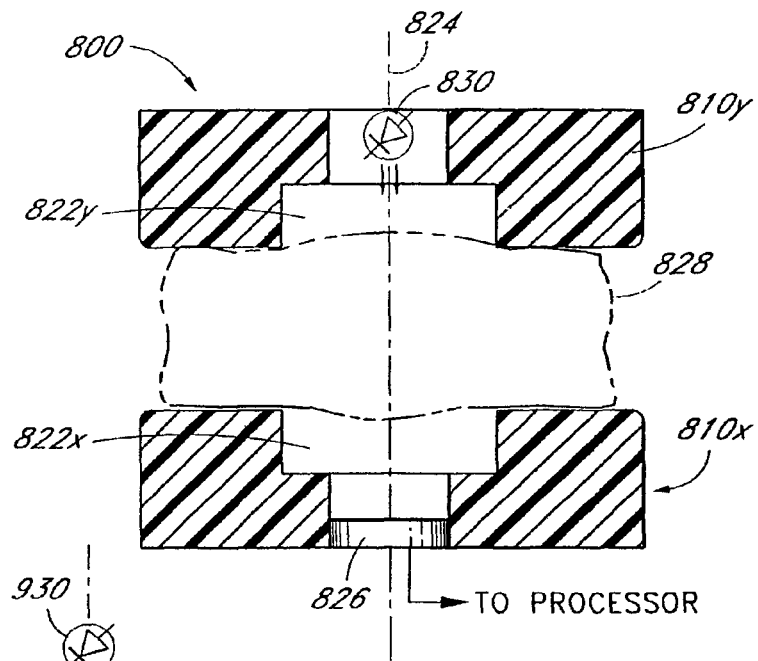
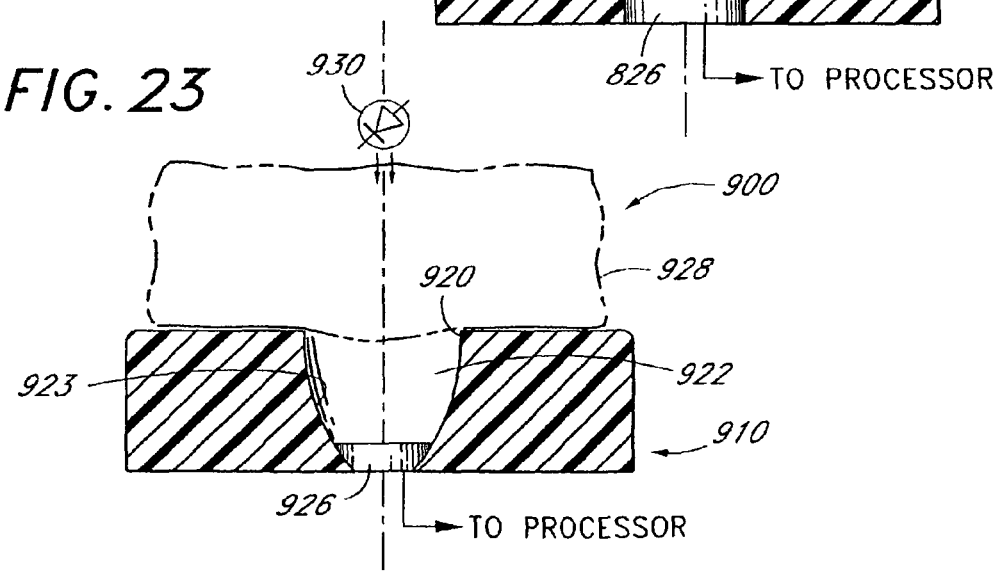

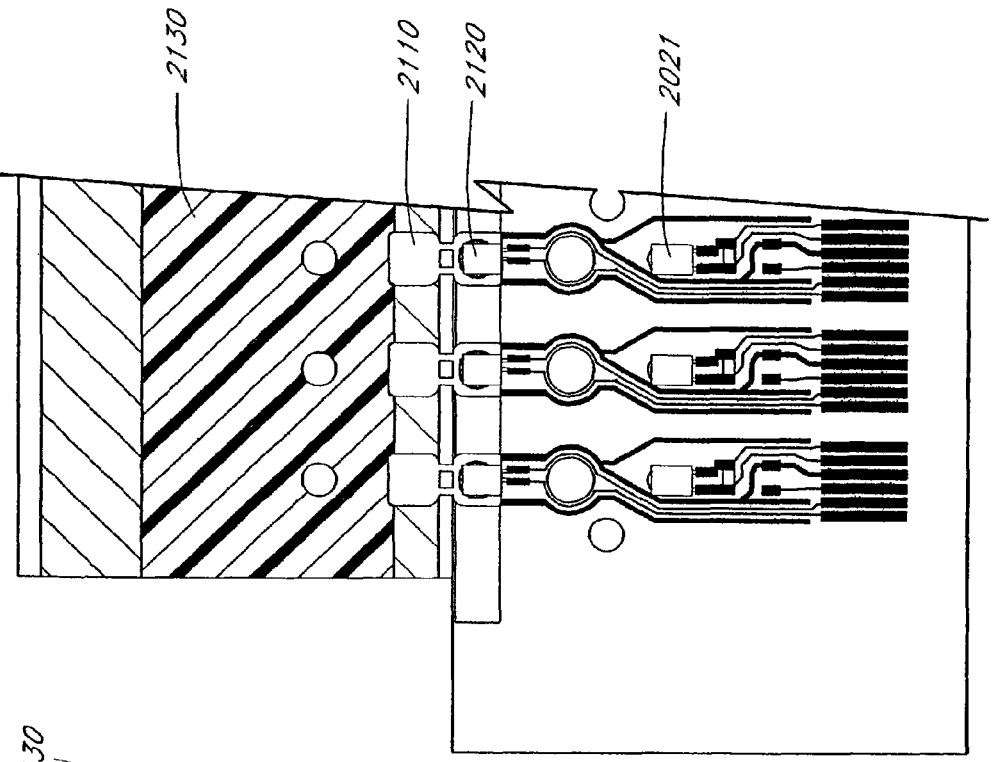
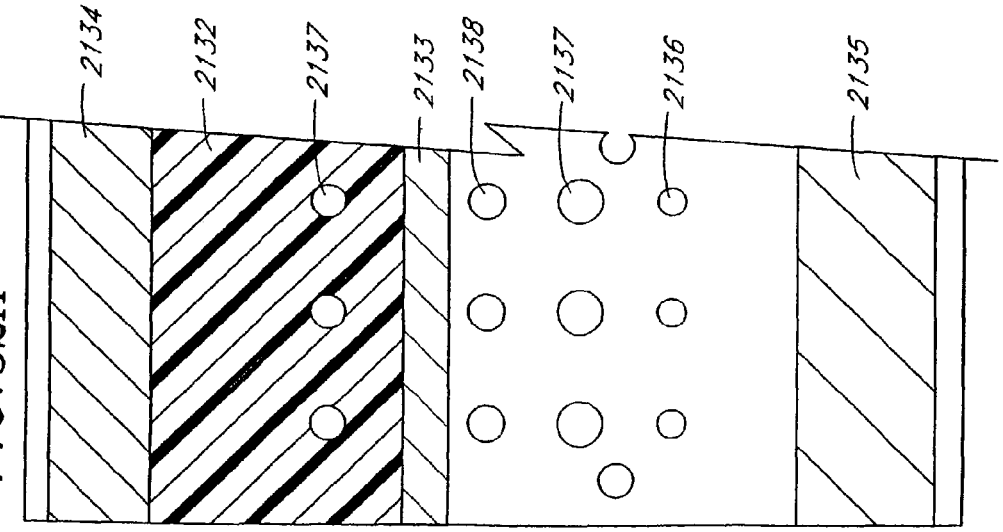

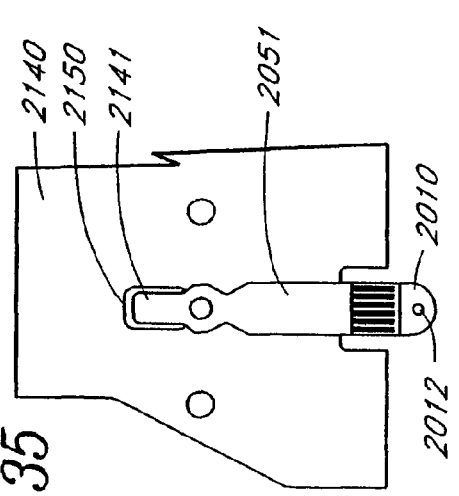
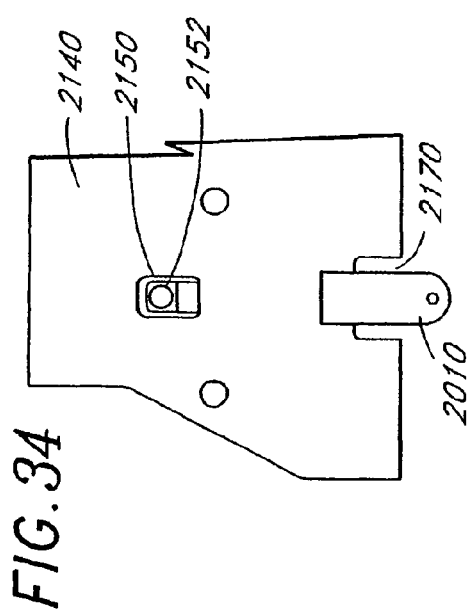
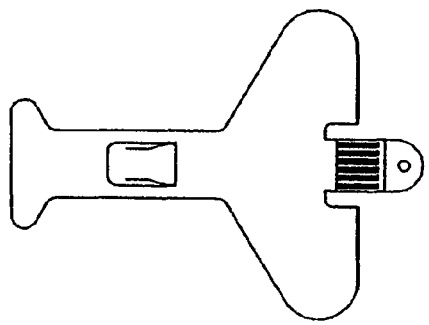
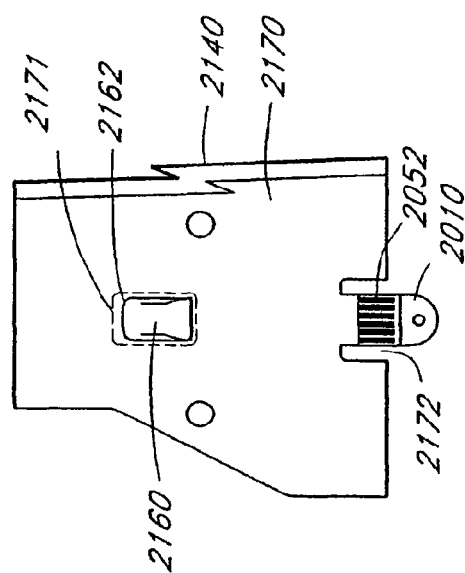
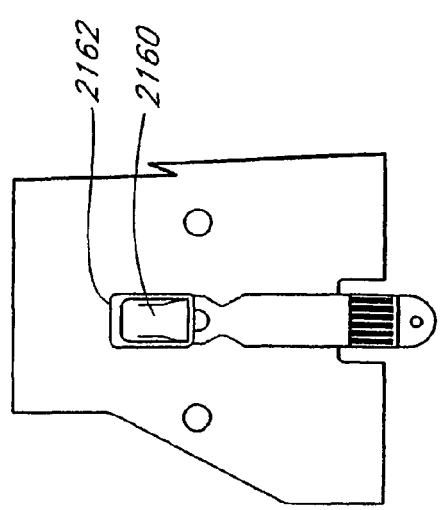

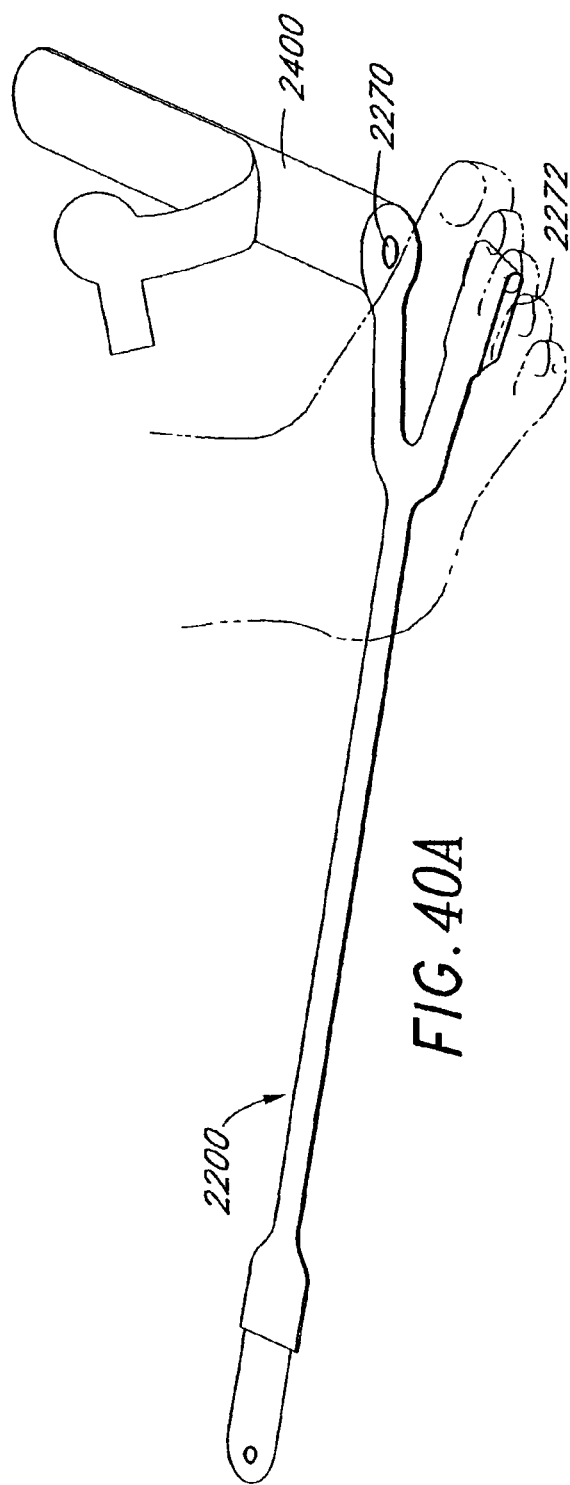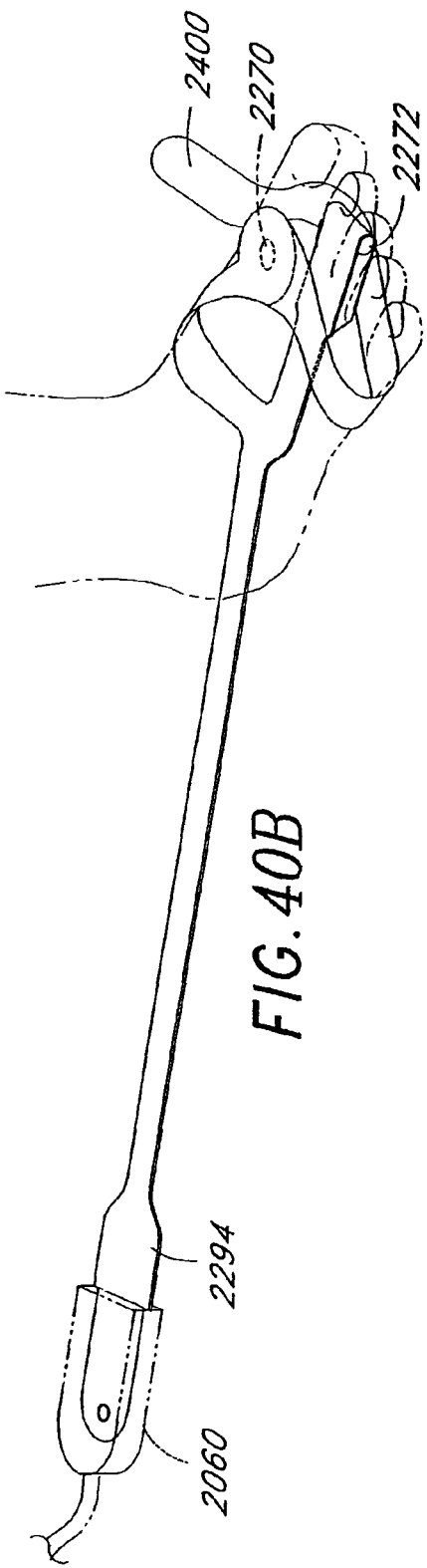
FIG. 40A
FIG. 40B

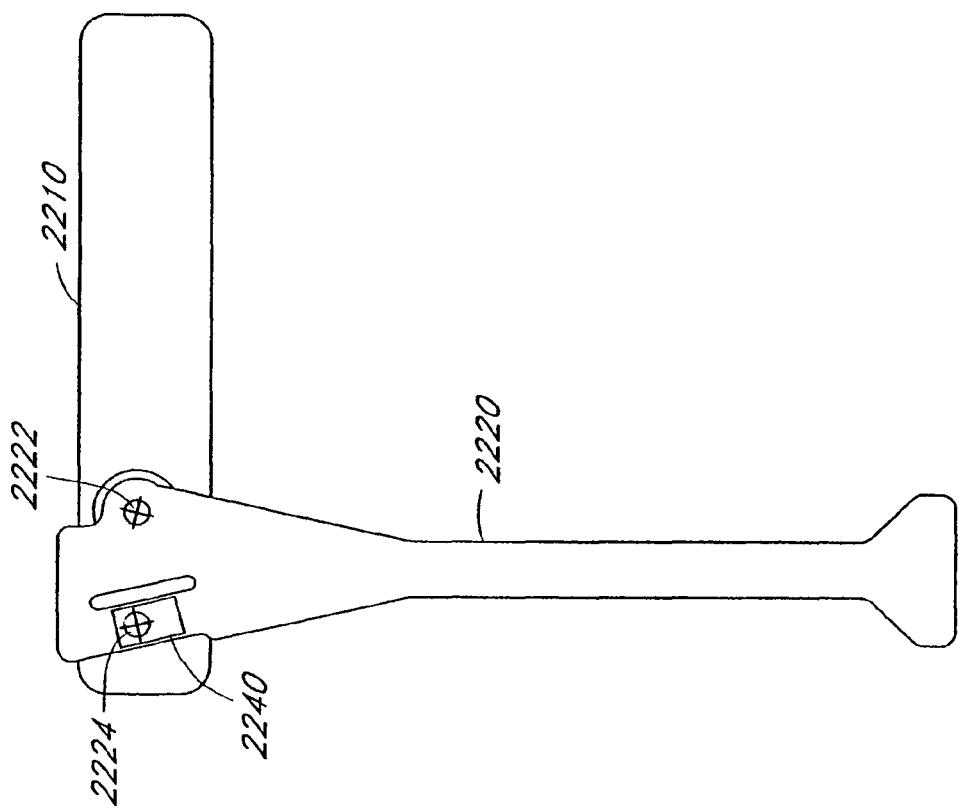
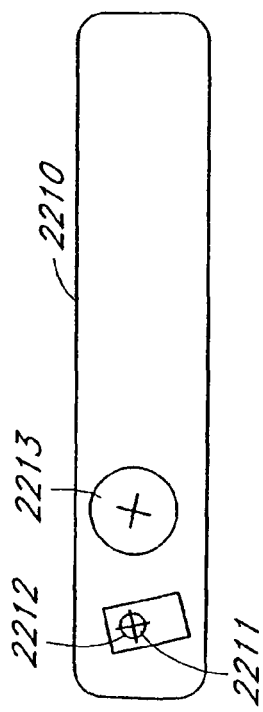

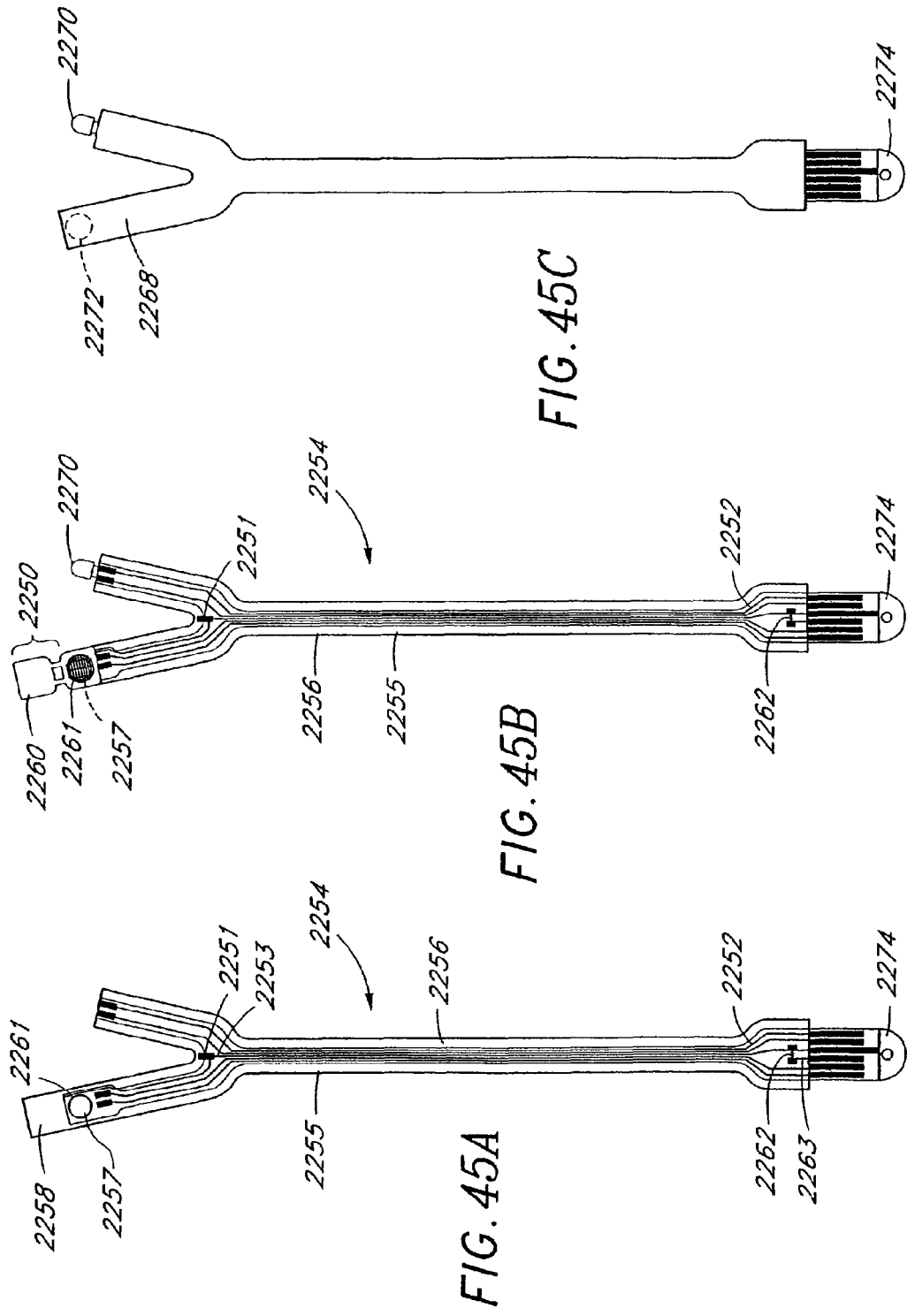

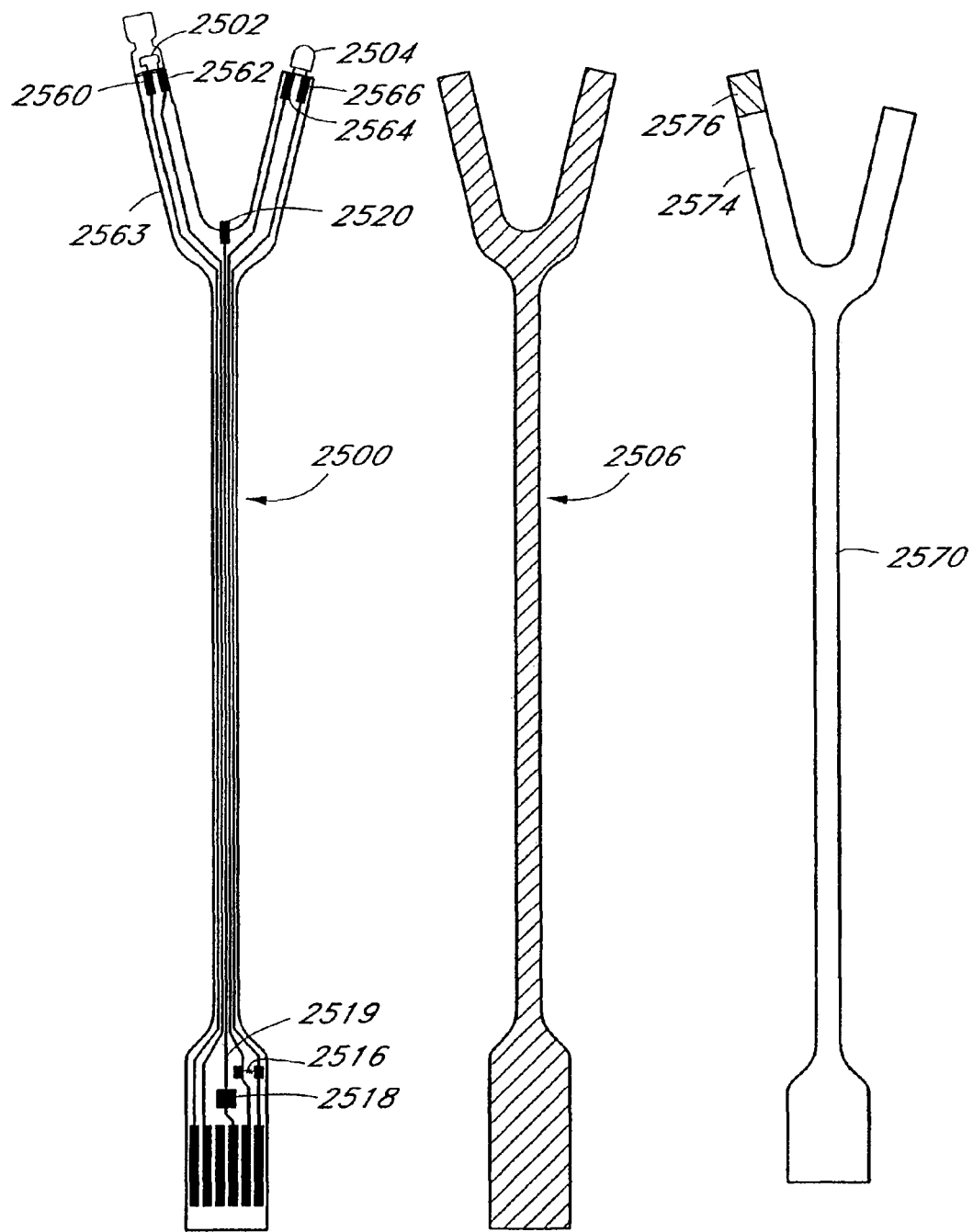

LOW-NOISE OPTICAL PROBES FOR REDUCING AMBIENT NOISE

REFERENCE TO RELATED APPLICATIONS

The present application claims priority benefit under 35 U.S.C. §120 to, and is a continuation U.S. patent application Ser. No. 10/957,843, filed Oct. 4, 2004 entitled "Low-Noise Optical Probes for Reducing Ambient Noise," now U.S. Pat. No. 7,483,730, which is a continuation of U.S. patent application Ser. No. 10/260,049, filed Sep. 27, 2002 entitled "Low-Noise Optical Probes for Reducing Ambient Noise," now U.S. Pat. No. 6,813,511, which is a continuation of U.S. patent application Ser. No. 09/898,990, filed Jul. 3, 2001 entitled "Low-Noise Optical Probes for Reducing Light Piping," now U.S. Pat. No. 6,792,300, which is a continuation of U.S. patent application Ser. No. 09/094,202, filed Jun. 9, 1998 entitled "Low-Noise Optical Probes," now U.S. Pat. No. 6,256,523, which is a continuation of U.S. patent application Ser. No. 08/543,789, filed Oct. 16, 1995 entitled "Low Noise Optical Probes," now U.S. Pat. No. 5,782,757. The present application incorporates the foregoing disclosures herein by reference.

FIELD OF THE INVENTION

The present invention relates to low-noise, disposable and reusable optical probes which may be used to sense optical energy passed through a medium to determine the characteristics of the medium.

BACKGROUND OF THE INVENTION

Energy is often transmitted through or reflected from a medium to determine characteristics of the medium. For example, in the medical field, instead of extracting material from a patient's body for testing, light or sound energy may be caused to be incident on the patient's body and transmitted (or reflected) energy may be measured to determine information about the material through which the energy has passed. This type of non-invasive measurement is more comfortable for the patient and can be performed more quickly.

Non-invasive physiological monitoring of bodily function is often required. For example, during surgery, blood pressure and the body's available supply of oxygen, or the blood oxygen saturation, are often monitored. Measurements such as these are often performed with non-invasive techniques where assessments are made by measuring the ratio of incident to transmitted (or reflected) light through a portion of the body, for example a digit such as a finger, or an earlobe, or a forehead.

Transmission of optical energy as it passes through the body is strongly dependent on the thickness of the material through which the light passes, or the optical path length. Many portions of a patient's body are typically soft and compressible. For example, a finger comprises skin, muscle, tissue, bone, blood, etc. Although the bone is relatively incompressible, the tissue, muscle, etc. are easily compressible with pressure applied to the finger, as often occurs when the finger moves. Thus, if optical energy is made incident on a finger and the patient moves in a manner which distorts or compresses the finger, the optical path length changes. Since a patient generally moves in an erratic fashion, the compression of the finger is erratic. This causes the change in optical path length to be erratic, making the absorption erratic, resulting in a difficult to interpret measured signal.

Many types of non-invasive monitoring devices have been developed to try to produce a clear and discernable signal as energy is transmitted through a medium, such as a finger or other part of the body. In typical optical probes a light emitting diode (LED) is placed on one side of the medium while a photodetector is placed on an opposite side of the medium. Many prior art optical probes are designed for use only when a patient is relatively motionless since, as discussed above, motion induced noise can grossly corrupt the measured signal. Typically, probes are designed to maximize contact between the LED and the medium and the photodetector and the medium to promote strong optical coupling between the LED, the medium, and the photodetector, thereby generating a strong output signal intensity. In this way, a strong, clear signal can be transmitted through the medium when the patient is generally motionless.

For example, U.S. Pat. No. 4,880,304 to Jaeb, et al. discloses an optical probe for a pulse oximeter, or blood oxygen saturation monitor, comprising a housing with a flat lower face containing a central protrusion in which a plurality of light emitting diodes (LEDs) and an optical detector are mounted. When the probe is placed on the patient's tissue, the protrusion causes the LEDs and the detector to press against the tissue to provide improved optical coupling of the sensor to the skin. In another embodiment (FIGS. 4a and 4b in the Jaeb patent), the LEDs and the detector are arranged within a central chamber, generally horizontal with respect to the tissue on which the probe is placed. A set of mirrors or prisms causes light to be directed from the LEDs onto the tissue through a polymer sealant within the chamber, the sealant providing a contact with the tissue for good optical coupling with the tissue.

U.S. Pat. No. 4,825,879 to Tan, et al. discloses an optical probe wherein a T-shaped wrap, having a vertical stem and a horizontal cross bar, is utilized to secure a light source and an optical sensor in optical contact with a finger. The light source is located in a window on one side of the vertical stem while the sensor is located in a window on the other side of the vertical stem. The finger is aligned with the stem and the stem is bent such that the light source and the sensor lie on opposite sides of the finger. Then, the cross bar is wrapped around the finger to secure the wrap, thereby ensuring that the light source and the sensor remain in contact with the finger to produce good optical coupling.

U.S. Pat. No. 4,380,240 to Jobsis, et al. discloses an optical probe wherein a light source and a light detector are incorporated into channels within a slightly deformable mounting structure which is adhered to a strap. Annular adhesive tapes are placed over the source and the detector. The light source and detector are firmly engaged with a bodily surface by the adhesive tapes and pressure induced by closing the strap around a portion of the body. An alternative embodiment provides a pressurized seal and a pumping mechanism to cause the body to be sucked into contact with the light source and detector.

U.S. Pat. No. 4,865,038 to Rich, et al. discloses an optical probe having an extremely thin cross section such that it is flexible. A die LED and a die photodetector are located on a flexible printed circuit board and encapsulated by an epoxy bead. A spacer, having circular apertures positioned in alignment with the LED and photodetector, is placed over the exposed circuit board. A transparent top cover is placed over the spacer and is sealed with a bottom cover placed under the circuit board, thereby sealing the probe from contaminants. A spine may be added to strengthen the device. The flexibility of the device allows it to be pinched onto the body causing the epoxy beads over the LED and the photodetector to protrude through the apertures in the spacer and press against the top cover such that good optical contact is made with the body.

U.S. Pat. No. 4,907,594 to Muz discloses an optical probe wherein a dual wall rubberized sheath is fit over a finger. A pump is located at the tip of the finger such that a pressurized chamber may be formed between the two walls, thereby causing an LED and a photodetector located in the inner wall to be in contact with the finger.

Each of the above described optical probes is designed to cause a strong measured signal at the photodetector by optimizing contact between the LED, the patient, and the probe. However, this optimization forces compressible portions of the patient's body to be in contact with surfaces which compress these portions of the patient's body when the patient moves. This can cause extreme changes in the thickness of material through which optical energy passes, i.e., changes in the optical path length and changes due to scattering as a result of venous blood movement during motion. Changes in the optical path length can produce enough distortion in the measured signal to make it difficult or impossible to determine desired information.

Furthermore, demand has increased for disposable and reusable optical probes which are suitably constructed to provide low-noise signals to be output to a signal processor in order to determine the characteristics of the medium. Many difficulties relating to motion-induced noise have been encountered in providing such an optical probe inexpensively. Furthermore, such probes tend to be difficult to use in certain applications, such as, applications where a patient's finger may move or shift during measurement, or, in a more extreme case, when the optical probe is employed on small children who typically do not sit still during the measurement process.

Thus, a need exists for a low-cost, low-noise optical probe which is easy to use under adverse conditions, and for a method of manufacturing such a probe. More specifically, a need exists for a probe which reduces motion induced noise, or motion artifacts, during measurement of a signal while still generating a transmitted or reflected signal of sufficient intensity to be measured by a detector.

SUMMARY OF THE INVENTION

The present invention involves a probe for use in non-invasive energy absorption (or reflection) measurements. One aspect of the present embodiment involves an optical probe for non-invasive measurement of characteristics of a medium, wherein the prove has an emitter which transmits optical radiation and a detector configured to detect the optical radiation transmitted by the emitter. The probe also has a flexible circuit assembly having circuit paths for connection with the emitter and the detector. A substrate forms a surface of the flex circuit assembly between the detector and the emitter. The substrate is constructed to minimize light piping from the emitter to the detector.

In one embodiment, the probe further has a flexible backing supporting the flex circuit, the flexible backing being configured to attach the optical probe to the medium. Advantageously, a an optical cavity is provided for the detector.

In one advantageous embodiment, the flexible circuit assembly is sufficiently flexible to provide spring action to minimize optical decoupling between the emitter and the detector due to perturbations of the medium. Advantageously, a flexible backing supporting the flex circuit is configured to affix the optical probe to the medium. Also, in one preferred embodiment, the flex circuit has an optical obstruction between the emitter and the detector.

In one preferred embodiment, the optical obstruction comprising an aperture through the flex circuit configured to receive a fingertip when the optical probe is affixed to a finger. The aperture stabilizes the finger within the probe so as to reduce optical decoupling between the emitter and the detector.

Preferably, the probe has an optical cavity containing the detector. In one advantageous embodiment, the optical cavity containing the detector is coated with a material which absorbs ambient light or the cavity is made from an ambient light absorptive material.

A further aspect of the present invention involves an probe for the non-invasive measurement of characteristics of a medium. According to this aspect, the optical probe has an emitter which transmits optical radiation and a detector configured to detect the optical radiation after attenuation through the medium. Again, a flexible circuit assembly extending between the emitter and the detector has electrical circuit paths for the detector and the emitter. A cushion positioned between the detector and the emitter along the flexible circuit is also provided. The cushion is preferably formed in the flexible circuit between the emitter and the detector so that the cushion abuts a patient's fingertip when the optical probe is attached to the fingertip.

Another aspect of the present invention involves an optical probe for the non-invasive measurement of characteristics of a medium, wherein the probe has a substrate which forms a surface for the probe such that the substrate is constructed to have a V-configuration with the emitter and detector positioned on opposite branches of the V-configuration. This configuration is advantageous for use with a newborn baby.

BRIEF DESCRIPTION OF THE DRAWINGS

FIG. 13 is a perspective view of a probe of the present invention having a three segment chamber.

FIG. 14 is a cross-sectional view of the probe of FIG. 13 incorporating a three segment chamber having a detector within it.

FIG. 15 is a cross-sectional view of another embodiment of the probe of FIG. 13 incorporating a light collimating lens.

FIG. 16 is a perspective view of a probe of the present invention specifically designed to be used with a digit.

FIG. 17 illustrates a schematic finger comprising fingernail, skin, bone, tissue, muscle, blood, etc.

FIG. 18 is a cross-section view of the probe of FIG. 16.

FIG. 19 is a longitudinal cross-sectional view of the probe of FIG. 16.

FIG. 20 is a cross-sectional view of another embodiment of the probe of FIG. 16 incorporating a light collecting lens.

FIG. 21 is a cross-sectional view of a probe of the present invention designed to be utilized for reflectance measurements.

FIG. 22 is a cross-sectional view of a probe which is advantageously used for non-invasive measurements when a material is compressible on more than one side. The probe has two bases, each with a chamber to house a detector or an energy source and thereby reduce motion artifacts.

FIG. 23 is a cross-sectional view of a probe having a generally cone-shaped chamber with a reflective surface which advantageously causes energy to be concentrated, or "funneled," onto the surface of a detector within the chamber, improving the measured signal.

FIGS. 32A and 32B illustrate a third step in the manufacturing process, wherein the flex circuits are placed onto a strip of flex circuit shield material.

FIG. 34 illustrates a fifth step of the manufacturing process, wherein a connector tab and a detector cavity are placed onto a sheet of base material.

FIG. 35 depicts a sixth stage of the manufacturing process, wherein the flex circuit assembly is positioned on the base material.

FIG. 36 illustrates a seventh step in the manufacturing process, wherein a cover is placed over the detector cavity.

FIG. 37 illustrates an eighth step of the manufacturing process, wherein face stock is placed over the flex circuit assembly on the base material.

FIG. 38 illustrates a ninth step of the manufacturing process, wherein the optical probe is die cut to the final shape shown in FIG. 29a.

FIGS. 40A and 40B illustrate the application of the a neonatal probe made in accordance with the present invention.

FIG. 42 illustrates a first step of the manufacturing process for a neonatal embodiment of the low-noise optical probe, wherein a first layer of tape is laid out.

FIG. 43 illustrates a second step in the manufacturing process for the neonatal probe, wherein a second elongated layer of tape is laid out over the first layer of FIG. 41.

FIGS. 45A-45C illustrate the manufacture of the neonate flex circuit assembly.

FIGS. 51-54 illustrate an alternative method of manufacturing the neonate probe.

DETAILED DESCRIPTION OF THE PREFERRED EMBODIMENT

Examination of a material is often advantageous, especially when it is difficult or expensive to procure and test a sample of the material. For example, in physiological measurements, it is often desirable to monitor a patient without drawing of blood or tissue from the patient. The known properties of energy absorption as energy propagates through a material may be used to determine information about the material through which the energy has passed. Energy is made incident on a material, and a measurement is made of energy either transmitted by or reflected from the material.

The amplitude of the measured signal is highly dependent on the thickness of the material through which the energy passes, or the optical path length, as well as other properties such as the erratic movement of venous blood during motion.

Figure 1:
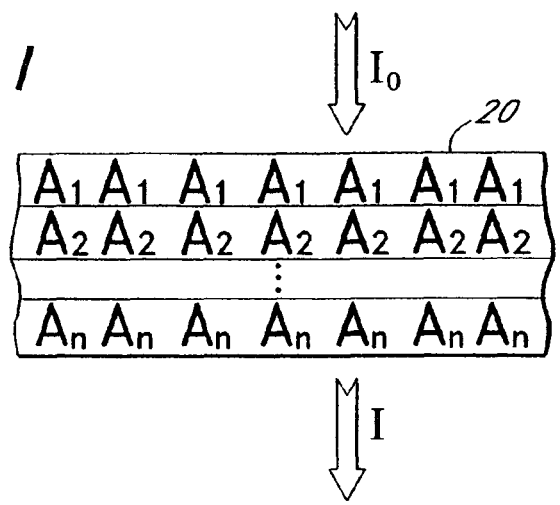
FIG. 1 illustrates a schematic medium comprising N different constituents.

A schematic medium 20 comprising N different constituents $A_1$ through $A_N$ is shown in FIG. 1. Energy transmitted through the medium 20 is approximately attenuated according to the equation:

$$I \approx I_0 e^{-\sum_{i=1}^{N} \epsilon_i c_i x_i} \tag{1}$$

where $\epsilon_1$ is the absorption coefficient of the $i^{th}$ constituent; $x_i$ is the thickness of the $i^{th}$ constituent through which light energy passes, or the optical path length of the $i^{th}$; and $c_i$ is the concentration of the $i^{th}$ constituent in thickness $x_i$.

Since energy absorption is strongly dependent on the thicknesses of the constituents $A_1$ through $A_N$ which make up the medium 20 through which the energy passes, when the thickness of the medium 20 changes, due to motion for example, the thicknesses of the individual constituents $A_1$ through $A_N$ change. This causes the absorption characteristics of the medium 20 to change.

Often a medium 20 is under random or erratic motion. For example, if the medium 20 is an easily compressible portion of a patient's body, such as a digit, and the patient moves, the medium 20 compresses erratically causing the individual thicknesses $X_1$ through $X_N$ of the constituents $A_1$ through $A_N$ to vary erratically. This erratic variation may cause large excursions in the measured signal and can make it extremely difficult to discern a desired signal, as would be present without motion induced noise, or motion artifacts.

Figure 2A:
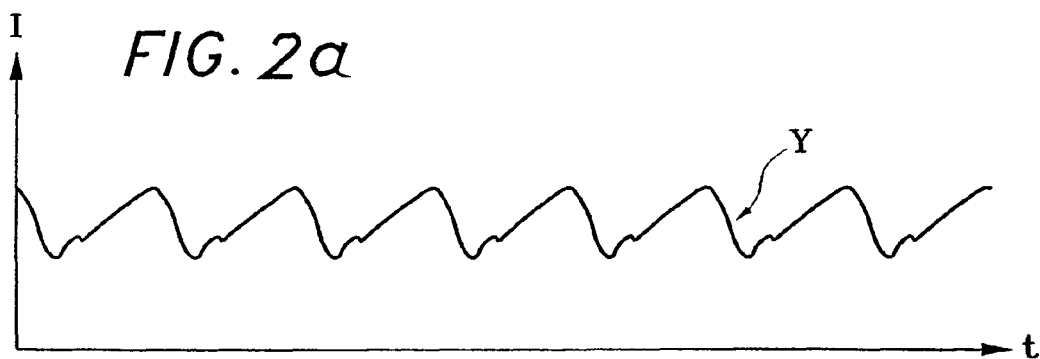
FIG. 2a illustrates an ideal plethysmographic signal that would be measured by the optical probe of the present invention when utilized for pulse oximetry.
Figure 2B:
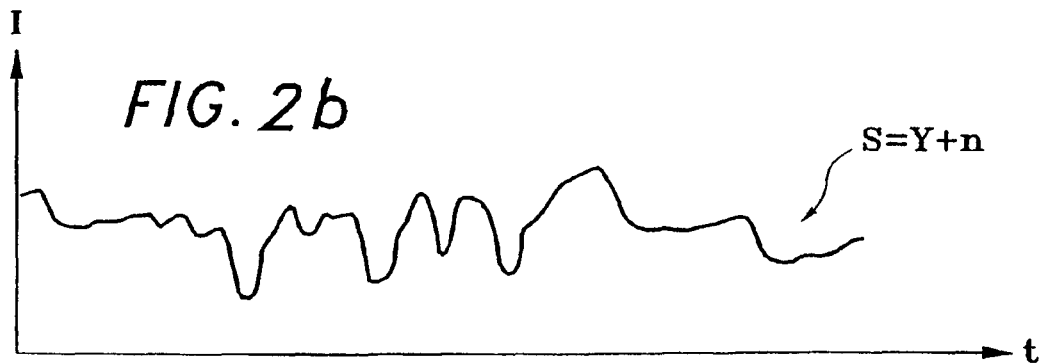
FIG. 2b illustrates a realistic signal measured by the optical probe of the present invention when utilized for pulse oximetry.

For example, FIG. 2a illustrates an ideal desired signal waveform, labeled Y, measured in one application of the present invention, namely pulse oximetry. FIG. 2b illustrates a more realistic measured waveform S, also measured in a pulse oximetry application, comprising the ideal desired signal waveform Y plus motion induced noise, n, i.e. S=Y+n. It is easily seen how motion artifacts obscure the desired signal portion Y.

Figure 3:
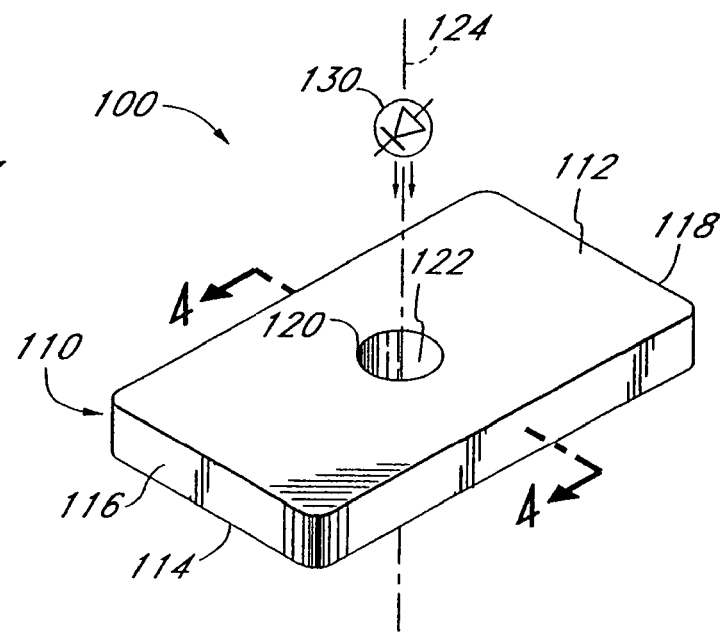
FIG. 3 is a perspective view of a probe of the present invention having a single segment chamber.
Figure 4:
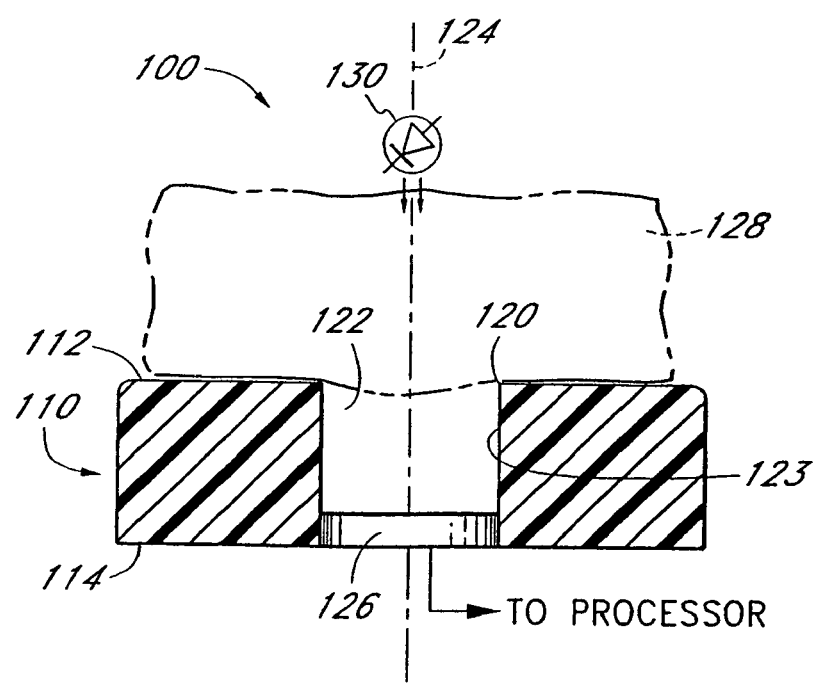
FIG. 4 is a cross-sectional view of an optical probe of the present invention illustrating a single segment chamber having a detector within it.

FIG. 3 is a perspective view of one embodiment of an optical probe 100 of the present invention which greatly diminishes the effects of motion artifacts on the measured signal. FIG. 4 shows a cross-sectional view of the optical probe 100 of the present invention taken along line 4-4 in FIG. 3. For clarity in the perspective view of FIG. 3, a material 128 on which measurements are to be taken is not shown placed adjacent the probe 100. However, the material 128 on which measurements are to be made is shown in FIG. 4. As illustrated in FIGS. 3 and 4, a base 110, having a top 112, a bottom 114, a forward end 116, and a rear end 118, is made of a material which is preferably rigid and opaque. It will be understood, however, that the probe 100 may be made of materials which may be rigid, resilient, opaque, or transparent, for example.

An aperture 120 is formed in the top 112 of the base 110. Typically, the aperture 120 is located at a point between one-quarter and one-half of the length of the base 100. The aperture 120 may be of any shape, including but not limited to circular, square, or triangular. The aperture 120 forms the opening to a chamber 122 which may also be of any shape. In one embodiment, a lateral cross-section (not shown) of the chamber 122 is the same shape as the aperture. A central axis 124 of the chamber 122 is defined by a line aligned perpendicular to the aperture 120 and extending generally through a central portion of the aperture 120.

In the embodiment of FIG. 4, a light source 130, typically a light emitting diode (LED), is affixed adjacent the material 128, aligned along the central axis 124 of the chamber 122 opposite the chamber 122. Typically, an adhesive such as medical tape is used to affix the LED 130 to the material 128. A detector 126, such as a photodetector, is placed within the chamber 122. A central portion of the photodetector 126 is generally aligned with the central axis 124 of the chamber 122, typically at the bottom 114 of the chamber 122. The photodetector 126 may be fixed within the chamber 122 according to a number of different methods, including but not limited to adhesive, a press fit, or clear epoxy resin which transmits light over a range of wavelengths of interest. Typically, no matter how the photodetector 126 is held within the chamber 122, the bottom surface 114 of the chamber 122 is made opaque either via the press fit or via paint or tape, for example.

It is often the case that materials 128 on which absorption measurements are performed are, at least in part, easily compressible. Easily compressible portions of the material 128 are placed directly adjacent (i.e., above) the chamber 122. The area surrounding the aperture 120 supports the material covering the chamber 122. The chamber 122 is wide enough that any compressible portion of the material 128 located above the aperture 120 may intrude into the chamber 122. Thus, the material 122 may rest above or penetrate slightly into the chamber 122 and is thereby shielded from perturbations which compress the material 128, such as pressure caused when the material 128 is touched.

In the present embodiment, the depth of the chamber 122 may range from 0.5 mm to 10 mm in depth, with 2-4 mm preferred, and 3-4 mm more preferred. Similarly, the diameter of the aperture 120 may, in the present embodiment, range from 3 mm to 20 mm, as required by the specific application. For instance, the aperture would be smaller for neonates than for adults. These sizes have been found to be effective in reducing perturbations and compression of the material 128, when the material is human skin.

The chamber 122 is deep enough that the photodetector 126 and the bottom 114 of the chamber 122 do not come into contact with the easily compressible portion of the material 128, even when the material 128 is caused to move. Thus, along the central axis 124 of the chamber 122 nothing comes into physical contact with the easily compressible portion of the material 128 and causes it to compress. With little or no compression of the material 128 in this region, the thickness of the material 128, or the optical path length of light energy propagating through the material 128, is substantially stabilized in the field of view of the photodetector. The movement of venous blood due to compression is also minimized in the field of view of the photodetector.

The LED 130 emits light at a known wavelength. The light propagates through the material 128 and an attenuated signal is transmitted into the chamber 122 to be received by the photodetector 126. As light from the LED 130 propagates through the material 128, it is scattered by the material 128 and is thus transmitted into the chamber 122 over a broad range of angles in a very complex manner. Thus, some of the light is caused to be incident on the opaque walls 123 of the chamber 122 and is absorbed. Although the signal travels through a greater optical distance to reach the photodetector 126 at the bottom 114 of the chamber 122 than if the photodetector 126 were immediately adjacent the material 128, thus eliminating direct coupling between the photodetector 126 and the material 128, the resulting degradation to signal intensity is compensated for by the stabilization of the optical path length and the resultant reduction of noise in the measured signal. The photodetector 126 produces an electrical signal indicative of the intensity of light energy incident on the photodetector 126. The electrical signal is input to a processor which analyzes the signal to determine characteristics of the media 128 through which the light energy has passed.

The opaque quality of the base 110 absorbs ambient light which can interfere with the signal measured at the photodetector 126. This further improves signal quality. Further, the opaque bottom 114 of the chamber 122 protects the photodetector 126 from ambient light which can obscure the desired signal measured at the photodetector 126. Thus, an accurate measurement of the intensity of the attenuated signal may be made at the photodetector 126.

Figure 5:
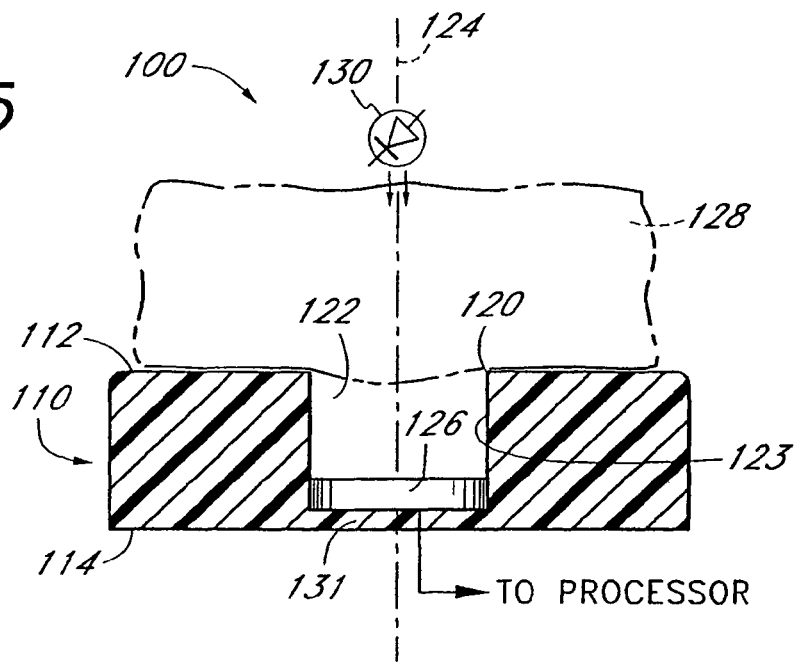
FIG. 5 is a cross-sectional view of a probe of the present invention having a detector resting on a shell of base material.

An alternative embodiment of the chamber 122 is shown in frontal cross-section in FIG. 5. A shell 131 of base 110 material covers the bottom 114 of the chamber 122. The photodetector 126 is mounted on the shell 131, within the chamber 122, generally aligned with the LED 130. The photodetector 126 is electrically connected to a processor through a small hole (not shown) in the shell 131. The shell 131 shields the photodetector 126 from ambient light which can seriously degrade the signal-to-noise ratio of the signal measured at the photodetector 126. It will be understood that the bottom 114 of the chamber 122 may be formed with or without the shell in any embodiment of the probe of the present invention.

Figure 6:
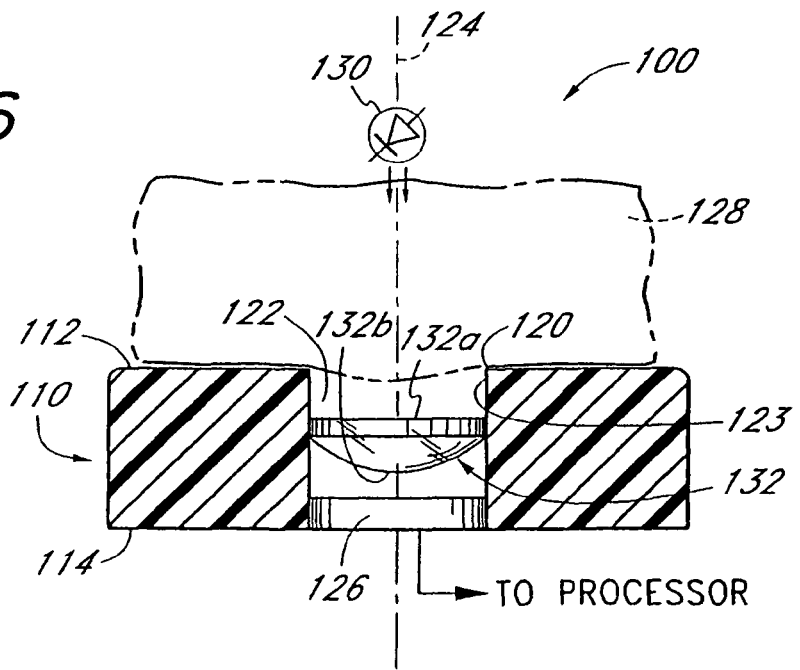
FIG. 6 is a cross-sectional view of a probe of the present invention incorporating a light collecting lens.

FIG. 6 shows a frontal cross sectional view of another embodiment of the probe 100 of the present invention wherein a light collecting lens 132 is placed within the chamber 122, between the material 128 which rests above or enters into the chamber 122 and the photodetector 126. The lens 132 has one generally planar surface 132a aligned parallel to the aperture 120 in the top 112 of the base 110, located deep enough within the chamber 122 that any material 128 which intrudes into the chamber 122 does not contact the planar surface 132a of the lens 132. Another surface 132b of the lens 132 is generally convex having its apex directed toward the photodetector 126 in the bottom 114 of the chamber 122. The lens 132 may be held in the chamber 122 by a number of means, including but not limited to optical adhesive, a lens retaining ring, or a press fit. The chamber 122 functions in the same manner as described above to stabilize the optical path length and reduce motion artifacts. The light collecting lens 132 gathers much of the light which was scattered as it was transmitted through the material 128 and causes it to be incident on the photodetector 126. This produces a stronger measured signal.

Figure 7:
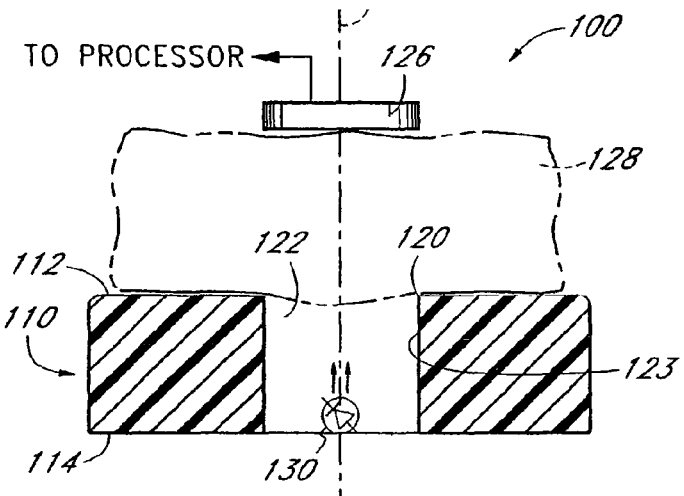
FIG. 7 is a cross-sectional view of a probe of the present invention illustrating a single segment chamber having an LED within it.

FIG. 7 shows another embodiment of the probe 100 of the present invention wherein the positions of the photodetector 126 and the LED 130 are interchanged. The LED 130 is placed within the chamber 122, typically at the bottom 114 of the chamber 122, generally aligned with the central axis 124 of the chamber 122. The LED 130 may be fixed within the chamber 122 according to a number of different methods, including but not limited to a press fit, adhesive, or clear epoxy resin which transmits light over a range of wavelengths of interest, such as around the wavelength which the LED emits. Again, a material 128 is placed on the base 110 having a compressible portion of the material 128 located directly above the chamber 122. The photodetector 126 is attached to the material 128, opposite the LED 130, such that the LED 130, the photodetector 126, and the chamber 122 are aligned along the central axis 124 of the chamber 122. The photodetector 126 is typically attached by an opaque material. For example, the photodetector 126 may be attached to the material 128 with opaque tape, thereby limiting signal degradation caused by ambient light. The photodetector 126 is, again, electrically connected to a processor.

The probe 100 of this embodiment functions substantially identically to the embodiment of the probe 100 having the photodetector 126 housed in the chamber 122. The chamber 122 stabilizes the optical path length by allowing easily compressible portions of the material 128 to rest above or intrude into the chamber 122, thereby stabilizing the optical path length and substantially reducing motion artifacts. This is true regardless of whether the photodetector 126 or the LED 130 is housed within the chamber 122.

Figure 8:
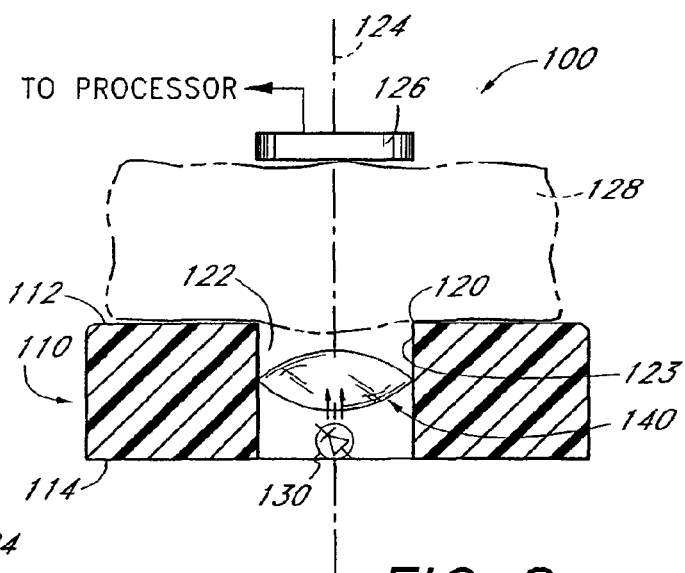
FIG. 8 is a cross-sectional view of a probe of the present invention incorporating a collimating lens assembly.

FIG. 8 shows a cross-sectional view of another embodiment of the probe 100 of the present invention wherein the LED 130 is located within the chamber 122. A collimating lens assembly 140 is placed within the chamber 122, between the material 128 which rests above or enters into the chamber 122 and the LED 130. Collimating lens assemblies 140 are well known in the art and, thus, the lens assembly 140 is represented schematically in the FIG. 8. The collimating lens assembly 140 is located deep enough within the chamber 122 that any material 128 which intrudes into the chamber 122 does not contact the lens assembly 140. The lens assembly 140 may be held in the chamber 122 by a number of means, including but not limited to optical adhesive, a lens retaining ring, or a press fit. The chamber 122 functions in the same manner as described above to stabilize the optical path length and reduce motion artifacts. The collimating lens assembly 140 causes light from the LED 130 to be focused on the material 128 above the chamber 122, thus providing a less scattered signal transmitted onto the photodetector 126 surface, thereby utilizing the photodetector 126 more effectively.

Figure 9:
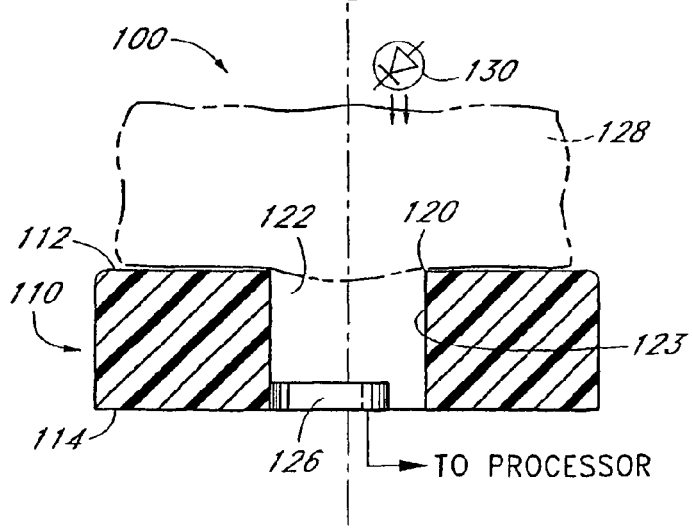
FIG. 9 is a cross-section view of a probe of the present invention wherein the LED and the detector are not aligned along the central axis of the chamber.

FIG. 9 shows another embodiment of the probe 100 of the present invention wherein the LED 130 and the photodetector 126 are not aligned along the central axis 124 of the chamber 122. Light is scattered within the material 128, causing at least a portion of the light emitted by the LED 130 to reach the photodetector 126 for measurement. As long as light emitted by the LED 130 and scattered by the material 128 reaches the photodetector 126 with great enough intensity to be measured, the LED 130 and the photodetector 126 need not be aligned. While alignment of the LED 130 and the photodetector 126 along the same axis causes the light emitted by the LED 130 to reach the photodetector 126 more directly, it is not necessary for operation of the probe of the present invention. In some applications, misalignment may even be advantageous. It will be understood that this is true for any embodiment of the probe of the present invention. Additionally, it will be understood that a photodetector 126 which fills the width of the chamber 122 is advantageous in that more of the light directed into the chamber 122 will be incident on the surface of the photodetector 126, resulting in a stronger measured signal. However, any size photodetector 126 which acquires enough energy to produce an adequately strong measured signal is acceptable. It will be understood that this is true for any embodiment of the probe of the present invention.

Figure 10:
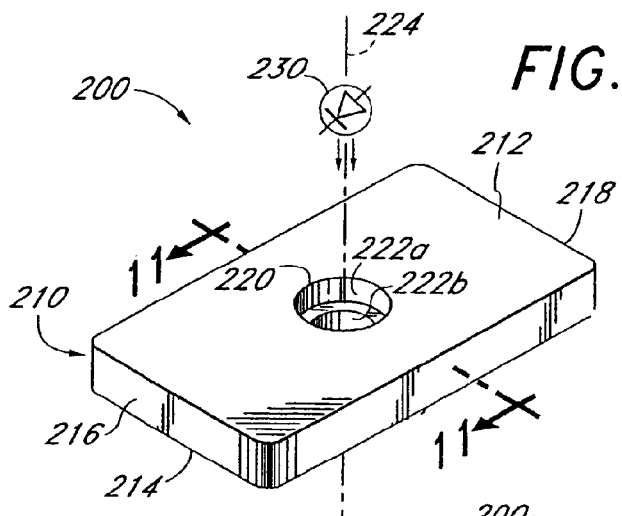
FIG. 10 is a perspective view of another embodiment of a probe of the present invention having a two segment chamber.
Figure 11:
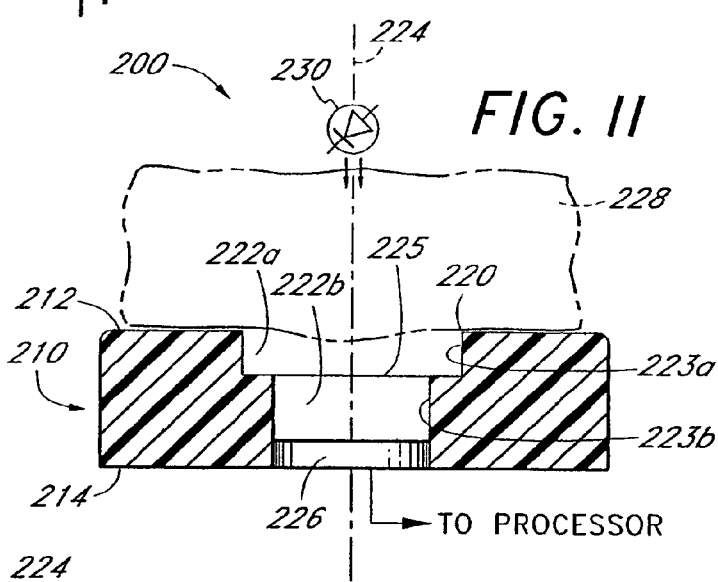
FIG. 11 is a cross-sectional view of another embodiment of the probe of FIG. 10 incorporating a two segment chamber having a detector within it.

A perspective view of another embodiment of a probe 200 of the present invention comprising a multi-segment chamber 222 is shown is FIG. 10. FIG. 11 shows a cross-sectional view of the probe 200 of the present invention taken along line 11-11 in FIG. 10. For clarity in the perspective view of FIG. 10, a material 228 on which measurements are to be taken is not shown placed adjacent the probe 200. However, the material 228 is shown adjacent the probe 200 in FIG. 11.

As illustrated in FIGS. 10 and 11, a base 210, having a top 212, a bottom 214, a forward end 216, and a rear end 218, is made of a material which is preferably rigid and opaque. It will be understood, however, that the probe 200 may be made of materials which may be rigid, resilient, opaque, or transparent, for example. An aperture 220 of any shape is formed in the base 210, similar to the aperture 120 described above in conjunction with the probe 100 of FIGS. 3 through 9. The aperture 220 forms the opening to a stabilizing segment 222a of the multiple segment chamber 222. A lateral cross-section (not shown) of the stabilizing segment 222a of the chamber 222 is typically the same shape as the aperture 220. Walls 223a of the stabilizing segment 222a are generally perpendicular to the aperture 220. A central axis 224 of the chamber 222 is defined by a line aligned generally perpendicular to the aperture 220 and extending generally through a central portion of the aperture 220 and the chamber 222.

A mounting segment 222b is located directly adjacent and below the stabilizing segment 222b, connected to the stabilizing segment 222b by a border 225. The mounting segment 222b shares the central axis 224 of the stabilizing segment 222a and is typically of smaller width. Walls 223b of the mounting segment 222b are generally parallel to the central axis 224. The mounting segment 222b may extend through the bottom 214 of the base 210, as shown in FIG. 11, or the mounting segment 222b may extend to just above the bottom 214 of the base 210, leaving a shell (not shown) of base 210 material at the bottom 214 of the chamber 222.

A photodetector 226 is placed in the mounting segment 222b of the chamber 222, typically at the bottom 214 of the mounting segment 222b, having a central portion of the photodetector 226 generally aligned with the central axis 224 of the chamber 222. The mounting segment 222b of the chamber 222 is deep enough that the photodetector 226 does not penetrate into the stabilizing segment 222 of the chamber 222. The photodetector 226 may be fixed within the chamber 222 according to a number of different methods, including but not limited to adhesive, a press fit, or a clear epoxy resin which transmits light over a range of wavelengths of interest. In this embodiment, the bottom 214 of the chamber 222 is made opaque via paint or tape, for example, or by leaving a shell (not shown) of base 210 material at the bottom 214 of the chamber 222 when the chamber 222 is formed. The photodetector 226 is electrically connected to a processor, similarly to the photodetector 126 in the previous embodiment of the probe 100 of the present invention.

An energy absorbing material 228 (the material under test) is placed over the base 210 as shown in the cross section of FIG. 11. A portion of the material 228 may rest above the chamber 222. Additionally, the stabilizing segment 222a of the chamber 222 is wide enough that any easily compressible portion of the material 228 may intrude into the stabilizing segment 222a of the chamber 222. The stabilizing segment 222a of the chamber 222 is deep enough that the portion of the material 228 which enters into the stabilizing segment 222a does not contact matter within the stabilizing segment 222a which might cause compression, even when the material 228 is caused to move.

A light emitting diode (LED) 230 is affixed adjacent to the material 228, opposite the aperture 220. The LED 230 is advantageously aligned along the central axis 224 to optimize the amount of light incident directly through the material 228 onto the photodetector 226. However, it will be understood that the positions of the photodetector 226 and the LED 230 could be interchanged as discussed in conjunction with FIG. 7. Additionally, a collimating lens assembly (not shown) could be added to the chamber 222 as discussed in conjunction with FIG. 8. The collimating lens assembly may be held in the chamber 222 similarly to a light collecting lens 232 discussed below. Further, it will be understood that the LED 230 and the photodetector 226 could be unaligned, as discussed in conjunction with FIG. 9.

As light from the LED 230 propagates through the material 228, it is scattered by the material 228 and is thus transmitted into the chamber 222 over a broad range of angles. Thus, some of the light is caused to be incident on the opaque walls 223a and 223b of the chamber 222 and is absorbed. However, the advantageous alignment of the photodetector 226 and the LED 230 along the central axis 224 causes a large percentage of the light to be incident on the surface of the photodetector 226. Since the material 228 remains substantially uncompressed above and within the stabilizing segment 222a, the thickness through which the light travels, or the optical path length, is substantially stabilized. Thus, the signal-to-noise ratio of the measured signal is improved by the suppression of motion artifacts due to the chamber 222.

Figure 12:
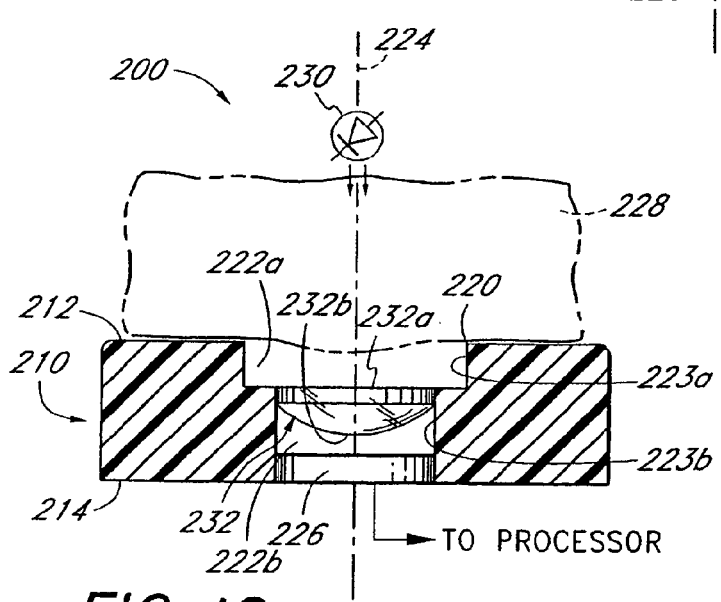
FIG. 12 is a cross-sectional view of another embodiment of the probe of FIG. 10 incorporating a light collecting lens in a two segment chamber.

In another embodiment of the probe 200, a light collecting lens 232 is inserted within the chamber 222, as shown in cross-section in FIG. 12. The lens 232 is advantageously supported at the border 225 between the stabilizing segment 222a and the mounting segment 222b. The lens may be held in place by a number of means, including but not limited to an optical adhesive, a lens retaining ring, or a press fit. The lens 232 has a generally planar surface 232a aligned with the border 225 between the stabilizing segment 222a and the mounting segment 222b and a generally convex surface 223b extending into the mounting segment 222b of the chamber 222. The stabilizing segment 222a of the chamber 222 is deep enough that the lens 232 does not contact any of the compressible material 228 which may have intruded into the chamber 222.

The lens 232 collects light which is incident on the planar surface 232a. Much of the light which is incident on this surface 232a at angles which would be absorbed by the walls 223a and 223b of the chamber 222 if the lens were not present is now directed toward the photodetector 226. Thus, a greater percentage of the light transmitted through the material 228 is caused to be incident on the photodetector 226, resulting in a stronger measured signal.

A perspective view of another embodiment of the probe 300 of the present invention which incorporates a chamber 322 having three segments 322a, 322b, and 322c is shown in FIG. 13. The probe 300 has a base 310 with a top 312, a bottom 314, a forward end 316, and a rear end 318. The base 310 is typically made of rigid opaque material. However, it will be understood that the base 310 may be made of other materials which may be rigid, resilient, opaque, or transparent, for example. A cross-sectional view of the chamber 322 of this embodiment is shown in FIG. 14. For clarity in the perspective view of FIG. 13, a material 328 on which measurements are to be taken is not shown placed adjacent the probe 300. However, the material 328 is shown in the cross section of FIG. 13. An aperture 320 of any shape is formed in the base 310, similar to the apertures 120 and 220 described above. The aperture 320 forms the opening to a stabilizing segment 322a of a three segment chamber 322. A lateral cross-section (not shown) of the stabilizing segment 322a of the chamber 322 is typically the same shape as the aperture 320. Walls 323a of the stabilizing segment 322a are generally perpendicular to the aperture 320. A central axis 324 of the chamber 322 is defined by a line aligned perpendicular to the aperture 320 and extending generally through a central portion of the aperture 320 and the chamber 322.

A second, transitional segment 322b of the chamber 322 is adjacent the stabilizing segment 322a of the chamber 322. A top border 325a is formed between the transitional segment 322b and the stabilizing segment 322a of the chamber 322. The transitional segment 322b shares the same central axis 324 as the stabilizing segment 322a. Walls 323b of the transitional segment 322b are angled inwardly such that a bottom border 325b of the transitional segment 322b is of smaller dimension than the top border 325a of the transitional segment 322b.

The bottom border 325b of the transitional segment 322b leads into a mounting segment 322c of the chamber 322. The mounting segment 322c shares the same central axis 324 of the stabilizing and transitional segments 322a and 322b and is typically of smaller width than the stabilizing and transitional segments 322a and 322b. Walls 323c of the mounting segment 322c are generally parallel to the central axis 324. Thus, any cross-section of the mounting segment 322c cut perpendicular to the central axis 324 of the chamber 322 is typically of approximately the same shape as the bottom border 325b of the transitional segment 322b of the chamber 322. The mounting segment 322c may extend through the bottom 314 of the base 310, as shown. Alternatively, the mounting segment 322c may extend to just above the bottom 314 of the base 310, leaving a shell (not shown) of base 310 material at the bottom 314 of the three segment chamber 322.

A photodetector 326 is placed within the mounting segment 322c of the chamber 322, at the bottom 314 of the chamber 322 in the present embodiment. A central portion of the photodetector 326 is aligned with the central axis 324 of the chamber 322. The mounting segment 322c of the chamber 322 is deep enough that the photodetector 326 does not penetrate into the stabilizing segment 322 of the chamber 322. The photodetector 326 may be fixed within the chamber 322 according to a number of different methods, including but not limited to adhesive, a press fit, or a clear epoxy resin which transmits light over a range of wavelengths of interest. In this embodiment, the bottom 314 of the chamber 322 is made opaque via the press fit, paint, or tape, for example. The photodetector 326 is electrically connected to a processor, similarly to the photodetectors 126 and 226 in the previous embodiments of the probe of the present invention.

When a portion of an energy absorbing material 328 is placed over the probe 300, as shown in the cross-section of FIG. 14, it may rest above the chamber 322. Additionally, the stabilizing segment 322a of the chamber 322 is wide enough that easily compressible portions of the material 328 may enter into the stabilizing segment 322a of the chamber 322. The stabilizing segment 322a of the chamber 322 is deep enough that the easily compressible portion of the material 328 which intrudes into the stabilizing segment 322a does not contact matter within the stabilizing segment 322a which might cause compression of the material 328, even when the material 328 is caused to move. The chamber 322 shields the compressible material 328 from contact which might cause compression of the material 328 and thereby change the optical path length through the material 328.

An LED 330 is affixed to the material 328, opposite the aperture 320. The LED 330 is advantageously aligned along the central axis 324 to optimize the amount of light incident directly through the material 328 onto the photodetector 326. It will be understood that the positions of the photodetector 326 and the LED 330 could be interchanged as discussed in conjunction with FIG. 7. Additionally, a collimating lens assembly (not shown) could be added to the chamber 322 as discussed in conjunction with FIG. 8. The collimating lens assembly may be held in the chamber 322 similarly to a light collecting lens 332 discussed below. Further, it will be understood that the LED 330 and the photodetector 326 could be unaligned, as discussed in conjunction with FIG. 9.

As light from the LED 330 propagates through the material 328, it is scattered by the material 328 and is thus transmitted into the chamber 322 over a broad range of angles. Thus, some of the light is caused to be incident on the opaque walls 323a, 323b, and 323c of the chamber 322 and is absorbed. However, the advantageous alignment of the photodetector 326 and the LED 330 along the central axis 324 of the chamber 322 causes a large percentage of the light to be incident on the surface of the photodetector 326. Since the material 328 remains substantially uncompressed above and within the stabilizing segment 322a, the thickness through which the light travels, or the optical path length, is substantially stabilized. Thus, the signal-to-noise ratio of the measured signal is improved by the suppression of motion artifacts. Additionally helping to improve the signal to noise ratio of the measured signal is the opaque bottom 314 of the mounting segment 322c which shelters the photodetector 326 from ambient light.

In another embodiment of the probe 300 of the present invention, a light collecting lens 332 is added to the transitional segment 322b of the chamber 322, as shown in a cross sectional view in FIG. 15. The lens 332 is supported in the transitional segment 322b and may be held in the transitional segment 322b by a number of means, including but not limited to optical adhesive, a lens retaining ring, or a press fit. The lens has a generally planar surface 332a aligned with the top border 325a of the transitional segment 322b of the chamber 322 and a generally convex surface 325b extending into the transitional segment 322b of the chamber 322. The stabilizing segment 322a of the chamber 322 is deep enough that the lens 332 does not contact the easily compressible material 328 which rests above or has intruded into the chamber 322.

The lens 332 collects light which is incident on the planar surface 332a. Much of the light which is incident on this surface 332a at angles which would have been absorbed by the walls 323a, 323b and 323c of the chamber 322 if the lens 332 were not present is now directed toward the photodetector 326. Thus, a greater percentage of the light transmitted through the material 328 is caused to be incident on the photodetector 326, resulting in a stronger measured signal.

It will be understood that the walls 323b of the transitional segment 322b in each of the above described embodiments need not be sloped to achieve transition from larger width in the stabilizing segment 322a to smaller width in the mounting segment 322c. The walls 323b of the transitional segment 322b could be aligned generally parallel to the central axis 324, arranged at a distance which would cause the width of the transitional segment 322b to be less than the width of the stabilizing segment 322a and greater than the width of the mounting segment 322c.

FIG. 16 shows a perspective view of another probe 400 of the present invention specifically designed for use with a digit, such as a finger or a toe. For ease of illustration, the present example will pertain to a finger, though it will be understood that the present example could equally well pertain to any digit. FIG. 17 illustrates a schematic finger 428 comprising nail, skin, bone, tissue, muscle, blood, etc. Constituents in the finger's pad 404, such as fat and tissue, are easily compressible with motion of a patient. Even slight motion of the finger 428 can cause the thickness of constituents within the finger 428 to change greatly, thereby causing large motion induced excursions to occur in a measured signal, often obscuring a desired portion of the measured signal from which information about the patient can be determined.

As depicted in FIG. 16, base 410 of the finger probe 400, called a saddle 410 in this embodiment, is generally semi-cylindrical and preferably is made of a rigid or semi-rigid, opaque material such as black plastic. It will be understood, however, that the saddle 410 may be made of other materials, including those which are rigid, resilient, opaque, and transparent, for example. The saddle 410 has a top 412, a bottom 414, a forward end 416, a rear end 418, a ridge 440, and sidewalls 450 which curve upwardly from the ridge 440 to form a U-shape in cross-section, as shown in FIG. 18.

As illustrated in FIGS. 16 and 18, an aperture 420 forms the entrance to a chamber 422, located between one-quarter to one-half of the length of the saddle 410 from the forward end 416 of the saddle 410, as shown in the longitudinal cross-section of FIG. 19. The aperture 420 can be of any shape, including but not limited to circular, square, or triangular. The aperture 420 is the entrance to a chamber 422, as described previously in conjunction with other embodiments 100, 200, and 300 of the probe of the present invention. The chamber 422 may also be of any shape, including but not limited to circular, square, or triangular in cross-section.

The chamber 422 may have one or more segments, as described previously. Although the chamber 422 shown in this embodiment is a three segment chamber 422, having a stabilizing segment 422a, a sloped-wall transitional segment 422b, and a mounting segment 422c aligned on a common central axis 424, it will be understood that any chamber 422 which protects from compression, a compressible portion of the finger 428 through which light energy passes during absorption measurements, is a viable alternative. It will further be understood that a shell (not shown) of saddle 410 material could cover the bottom 414 of the chamber 422, as described previously with respect to the embodiment of the probe shown in FIG. 5.

A photodetector 426 is placed within the chamber 422, typically at the bottom 414 of the mounting segment 422c of the chamber 422. The photodetector 426 may be in place by adhesive, a press fit, or a clear epoxy resin which transmits light over a range of wavelengths of interest, for example. Typically, the bottom 414 of the chamber 422 is made opaque via tape or paint, for example, such that ambient light does not affect the photodetector 426.

The finger 428 is placed on the saddle 410, the finger pad 404 directly adjacent the aperture 420 and chamber 422. Additionally, the finger pad 404 may rest above the chamber 422. The aperture 420 and stabilizing segment 422a of the chamber 422 are wide enough that any easily compressible portion of the finger 428, such as a portion of the finger pad 404, may intrude into the chamber 422. The stabilizing segment 422a of the chamber 422 is deep enough that any portion of the finger 428 which does penetrate into the stabilizing segment 422a does not contact any matter within the stabilizing segment 422a which might cause compression of the finger 428, even when the finger 428 is caused to move.

An LED 430 is affixed to the finger 428, generally opposite the aperture 420. The LED 430 is typically attached to the finger 428 via adhesive, such as medical tape. The LED 430 is advantageously aligned along the central axis 424 to optimize the amount of light transmitted directly through the finger 428 onto the photodetector 426. However, it will be understood that the positions of the photodetector 426 and the LED 430 could be interchanged as discussed in conjunction with FIG. 7. Additionally, a collimating lens assembly (not shown) could be added to the chamber 422 as discussed in conjunction with FIG. 8. The collimating lens assembly may be held in the chamber 422 similarly to a light collecting lens 432 discussed below. Further, it will be understood that the LED 430 and the photodetector 426 could be unaligned, as discussed in conjunction with FIG. 9.

The LED 430 emits a light energy signal which propagates through the finger 428 and is transmitted into the chamber 422. The chamber 422 shields from compression the portion of the finger 428 through which light energy passes. Thus, the optical path length of the light through the finger 428 is substantially stabilized and motion artifacts are substantially reduced in the measured signal. It will be understood that a single segment chamber as described in conjunction with FIGS. 3 through 9 or a two segment chamber as described in conjunction with FIGS. 10 through 12 could equally well be used in the finger probe 400 of the present invention to shield the compressible portion of the finger 428 from compression and thereby reduce motion artifacts.

FIGS. 16, 18, and 19 illustrate a perspective view, a frontal cross-sectional view, and a longitudinal cross-sectional view, respectively, of one embodiment of the finger probe 400. The curvature of the saddle 410 is correlated to the average curvature of the finger 428 such that the sidewalls 450 form a semi-circular splint-type support for the finger 428. The saddle 410 is approximately 25 mm long between the forward end 416 and the rear end 418, such that a portion of the finger 428 between its tip 406 and approximately its first knuckle 408 (shown in FIG. 17) fits between the front 416 and the rear 418 ends of the probe 400. The curvature of the saddle 410 is generally defined by a line 460 (shown in FIG. 18) which is tangent to a sidewall 450 at an angle between 30□ and 5□ from horizontal.

The placement of the aperture 420 at a point between one-third and one-half of the length of the saddle 410, causes the thickest section of the compressible portion of the finger 428, or the finger pad 404, to rest above and within the chamber 422. Thus, the portion of the finger 428 with the greatest amount of compressible material is safeguarded from compression by the chamber 422.

In the embodiment of the finger probe 400 shown in FIGS. 16, 18, 19, and 20, the aperture 420 is generally circular and the chamber 422 has three segments 422a, 422b, and 422c, as shown in the cross-sectional view of FIG. 18. Advantageously employed dimensions for the finger probe 400 illustrated in FIGS. 16, 18, 19, and 20 include the stabilizing segment 422a of the chamber 422 being generally cylindrical and having a diameter of approximately seven millimeters. Additionally, the stabilizing segment 422a of the chamber 422 is deep enough that any portion of the finger 428 which penetrates into the chamber remains substantially free of perturbation, even when the finger 428 moves. An advantageous depth for the stabilizing segment 422a is thus approximately two millimeters deep. The mounting segment 422c of the chamber 422 is also cylindrical, having a diameter of approximately five millimeters. The transitional segment 422b of the chamber 422 is of varying diameter, having sloped walls 423b, such that a top border 425a is approximately seven millimeters in diameter and a bottom border 425b is approximately five millimeters in diameter. A detector 426 having up to a 5 millimeter diameter is positioned in the bottom 416 of the mounting segment 422c of the chamber 422.

In another embodiment of the finger probe 400, a light collecting lens 432 may be added to the finger probe 400 of the present invention, as shown in FIG. 20. The saddle 410 and the chamber 422 function as discussed above. The lens 432 functions as described above in conjunction with FIGS. 6, 12, and 15 to collect light incident on the lens 432 which would be absorbed by the walls 423a, 423b and 423c of the chamber 422 if the lens 432 were not present. Thus, a greater percentage of the light transmitted through the finger 428 is directed onto the photodetector 426, resulting in a stronger measured signal.

Other embodiments of the probe of the present invention may be specifically designed and manufactured for use with an earlobe or other thin section of the body, such as a nostril or a lip, using the principles described herein. Also, embodiments of the probe of the present invention utilizing the properties of attenuation as energy is reflected from a medium, rather than transmitted through a medium, may be made using similar principles.

A probe 700 specifically designed to measure reflected energy is shown in cross-section in FIG. 21. A base 710 is placed adjacent a material 728 on which reflectance measurements are to be made. A photodetector 726 and an LED 730 are located within the base 710. In the embodiment shown in FIG. 21, the photodetector 726 is positioned within a chamber 722x and the LED 730 is positioned within a chamber 722y. Although single segment chambers 722x and 722y are illustrated, the chambers 722x and 722y may be of any suitable shape and size. The chambers 722x and 722y function to stabilize the optical path length, as discussed previously, by shielding from compression any compressible portion of a material which rests above or intrudes into the chambers 722x and 722y.

A light collecting lens (not shown) may be added to the chamber 722x having the photodetector 726 within it, as discussed previously in conjunction with FIGS. 6, 12 and 15. Additionally, a collimating lens assembly (not shown) may be added to the chamber 722y having the LED 730 in it, as discussed previously in conjunction with FIG. 8. The chambers 722x and 722y may be formed with or without a shell (not shown) of base 710 material, as discussed previously in conjunction with FIG. 5.

It will be understood that in other embodiments (not shown) of the reflectance probe 700, the photodetector 726 could protrude from the base 710 and the LED 730 be located within a chamber 722y or the LED 730 could be protrude from the base 710 and the photodetector 726 could be located within a chamber 722x. Additionally, the photodetector 726 and the LED 730 could be located within a single chamber 722. In any embodiment the chamber(s) 722 may have any number of segments of any suitable shape.

The type of probe 700 which relies on reflection may be advantageously utilized on materials where a photodetector 726 and an LED 730 cannot be placed on opposite sides of the material 728, such as with the forehead. However, a reflectance probe 700 can be used anywhere a non-invasive measurement needs to be taken, such as a lip, an earlobe, or a finger, for example.

FIG. 22 shows a cross-sectional view of another probe 800 of the present invention wherein two bases 810x and 810y are placed adjacent to a material 828 on which measurements are to be made. The bases 810x and 810y are located on opposite sides of the material 828. A photodetector 826 is placed in a chamber 822x in the base 810x. An LED 830 is placed in a chamber 822y in the base 810y. The photodetector 826 and the LED 830 are aligned substantially along a central axis 824. Although two segment chambers 822x and 822y are illustrated, the chambers 822x and 822y may be of any suitable shape and size. Independent of which shape of chamber is utilized, the chambers 822x and 822y function to stabilize the optical path length and thereby reduce the effects of motion artifacts on the measured signals.

As discussed previously, the probe 800 may be modified slightly with a light collecting lens (not shown) added to the chamber 822x with the photodetector 826 in it. A collimating lens assembly (not shown) may be added to the chamber 822y with the LED 830 in it. Additionally, the chambers 822x and 822y may be formed with or without a shell (not shown) of base 810x and 810y material. The probe 800 is particularly advantageous when a material 828 is compressible on more than one side since each chamber 822x and 822y supports and shields from compression any compressible portion of a material 828 which rests above or intrudes into the chambers 822x and 822y, respectively.

FIG. 23 shows a cross-sectional view of another probe 900 of the present invention wherein a chamber 922 having walls 923 is formed to concentrate, or "funnel," energy onto the surface of a photodetector 926. An aperture 920 is formed in a base 910, the aperture 920 leading to a generally cone-shaped chamber 922. The base 910 is placed adjacent a material 928 on which measurements are to be made, the chamber 922 being placed directly adjacent any easily compressible portion of the material 928. The photodetector 926 is placed within the chamber 922, typically at the bottom of the chamber 928. A light emitting diode 930 is placed on the material 928, generally opposite and aligned with the photodetector 926.

As discussed previously, a portion of the material 928 is supported by the area surrounding the aperture 920. Additionally, the aperture 920 and chamber 922 are wide enough that any easily compressible portion of the material 928 may intrude into the chamber 922 without being compressed, thereby shielding this portion of the material 928 from compression, even during motion of the material 928. This substantially stabilizes the optical path length and improves the signal to noise ratio of the signal measured at the photodetector 926.

Further improving the signal to noise ratio of measurements made with the probe 900, reflective material, such as a highly reflective metal, covers the walls 923 of the chamber 922. This causes light scattered by the material 928 and made incident on the walls of the chamber 922 to be reflected. The cone shape causes the light to be concentrated generally on the photodetector 926.

Depending upon the shape of the photodetector 926, the chamber 922 may be advantageously contoured to maximize the funneling of light onto the photodetector 926. If the photodetector 926 is flat, the chamber is most advantageously shaped having a generally hyperbolic cross-section. However, if the photodetector 926 is spherical or slightly curved, as is often the case due to manufacturing processes, the chamber is most advantageously shaped having a cone-shaped cross-section with uncurved walls 923.

As discussed previously in conjunction with other embodiments of the probe of the present invention, the probe 900 may be modified to include a light collecting lens (not shown). Alternatively, an LED 930 could be placed within the chamber 922 instead of the photodetector 926. With the LED in the chamber 922, a collimating lens assembly (not shown) could be placed within the chamber 922. Two bases 910 with two generally cone-shaped chambers could be utilized on one or either side of a material 928. A single base 910 with two generally cone-shaped chambers 922 located side by side could also be used for reflective measurements. Additionally, the photodetector 926 and the LED 930 need not be aligned along the central axis 924.

Figure 24:
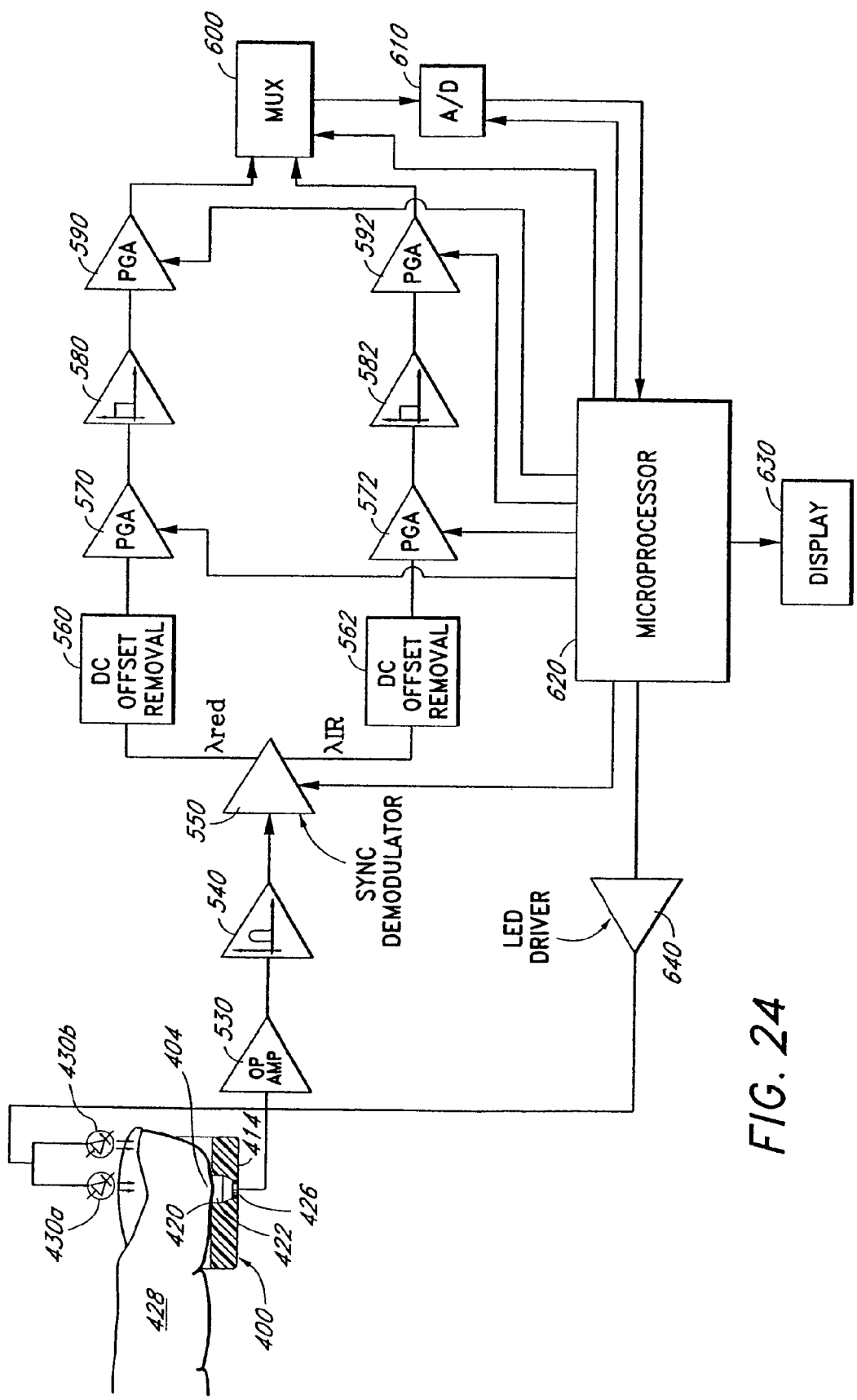
FIG. 24 is a schematic of one system which may advantageously employ a probe of the present invention.

FIG. 24 depicts one embodiment of a probe constructed in accordance with the present invention coupled to an oximeter. The oximeter could be any oximeter known in the art which utilizes light attenuation measurements. A block diagram of one possible oximeter is depicted in FIG. 24. The oximeter shown in FIG. 24 is a pulse oximeter wherein the finger probe 400 is employed and two measured signals at different wavelengths, one of which is typically red and the other of which is typically infrared, are alternately passed through the finger 428. Signals measured at the photodetector 426 are then processed to determine the amount of oxygen available to the body. This is evaluated by finding the saturation of oxygenated hemoglobin in blood comprising both oxygenated and deoxygenated hemoglobin.

Two LEDs 430a and 430b, one LED 430a emitting red wavelengths and another LED 430b emitting infrared wavelengths, are placed adjacent the finger 428. The finger probe 400 is placed underneath the finger 428, the aperture 420 and chamber 422 located directly adjacent the finger pad 404. The photodetector 426 in the bottom 414 of the chamber 422 is connected to a single channel of common processing circuitry including an amplifier 530 which is in turn connected to a band pass filter 540. The band pass filter 540 passes signal into a synchronized demodulator 550 which has a plurality of output channels. One output channel is for signals corresponding to visible wavelengths and another output channel is for signals corresponding to infrared wavelengths.

The output channels of the synchronized demodulator 550 for signals corresponding to both the visible and infrared wavelengths are each connected to separate paths, each path comprising further processing circuitry. Each path includes a DC offset removal element 560 and 562, such as a differential amplifier, a programmable gain amplifier 570 and 572 and a low pass filter 580 and 582. The output of each low pass filter 580 and 582 is amplified in a second programmable gain amplifier 590 and 592 and then input to a multiplexer 600.

The multiplexer 600 is connected to an analog-to-digital converter 610 which is in turn connected to a microprocessor 620. Control lines between the microprocessor 620 and the multiplexer 600, the microprocessor 620 and the analog-to-digital converter 610, and the microprocessor 620 and each programmable gain amplifier 570, 572, 590, and 592 are formed. The microprocessor 620 has additional control lines, one of which leads to a display 630 and the other of which leads to an LED driver 640 situated in a feedback loop with the two LEDs 430a and 430b.

Each of the LEDs 430a and 430b alternately emits energy which is absorbed by the finger 428 and received by the photodetector 426. The photodetector 426 produces an electrical signal which corresponds to the intensity of the light energy striking the photodetector 426 surface. The amplifier 530 amplifies this electrical signal for ease of processing. The band pass filter 540 then removes unwanted high and low frequencies. The synchronized demodulator 550 separates the electrical signal into electrical signals corresponding to the red and infrared light energy components. A predetermined reference voltage, $V_{ref}$, is subtracted by the DC offset removal element 560 and 562 from each of the separate signals to remove substantially constant absorption which corresponds to absorption when there are no motion artifacts. Then the first programmable gain amplifiers 570 and 572 amplify each signal for ease of manipulation. The low pass filters 580 and 582 integrate each signal to remove unwanted high frequency components and the second programmable gain amplifiers 590 and 592 amplify each signal for further ease of processing.

The multiplexer 600 acts as an analog switch between the electrical signals corresponding to the red and the infrared light energy, allowing first a signal corresponding to the red light to enter the analog-to-digital convertor 610 and then a signal corresponding to the infrared light to enter the analog-to-digital convertor 610. This eliminates the need for multiple analog-to-digital convertors 610. The analog-to-digital convertor 610 inputs the data into the microprocessor 620 for calculation of the saturation of oxygen according to known methods, such as those described in U.S. patent application Ser. No. 07/666,060 filed Mar. 7, 1991, and abandoned in favor of continuation U.S. patent application Ser. No. 08/249,690, entitled "SIGNAL PROCESSING APPARATUS AND METHOD," filed May 26, 1994, both assigned to MASIMO CORPORATION, the same assignee as the present patent, and incorporated herein by reference. U.S. patent application Ser. No. 08/320,154, entitled Signal Processing Apparatus, filed on Oct. 7, 1994 is also incorporated by reference herein. The microprocessor 620 centrally controls the multiplexer 600, the analog-to-digital convertor 610, and the first and second programmable gain amplifiers 570, 590, 572, and 592 for both the red and the infrared channels. Additionally, the microprocessor 620 controls the intensity of the LEDs 430a and 430b through the LED driver 640 in a servo loop to keep the average intensity received at the photodetector 426 within an appropriate range.

As explained above, the probe of the present invention could be used with a variety of oximeter systems. A recent embodiment of an oximeter by the assignee of the present application is described in detail in U.S. patent application Ser. No. 08/320,154, entitled "Signal Processing Apparatus," and filed Oct. 7, 1994, which patent application is also incorporated herein by reference.

Figure 25:
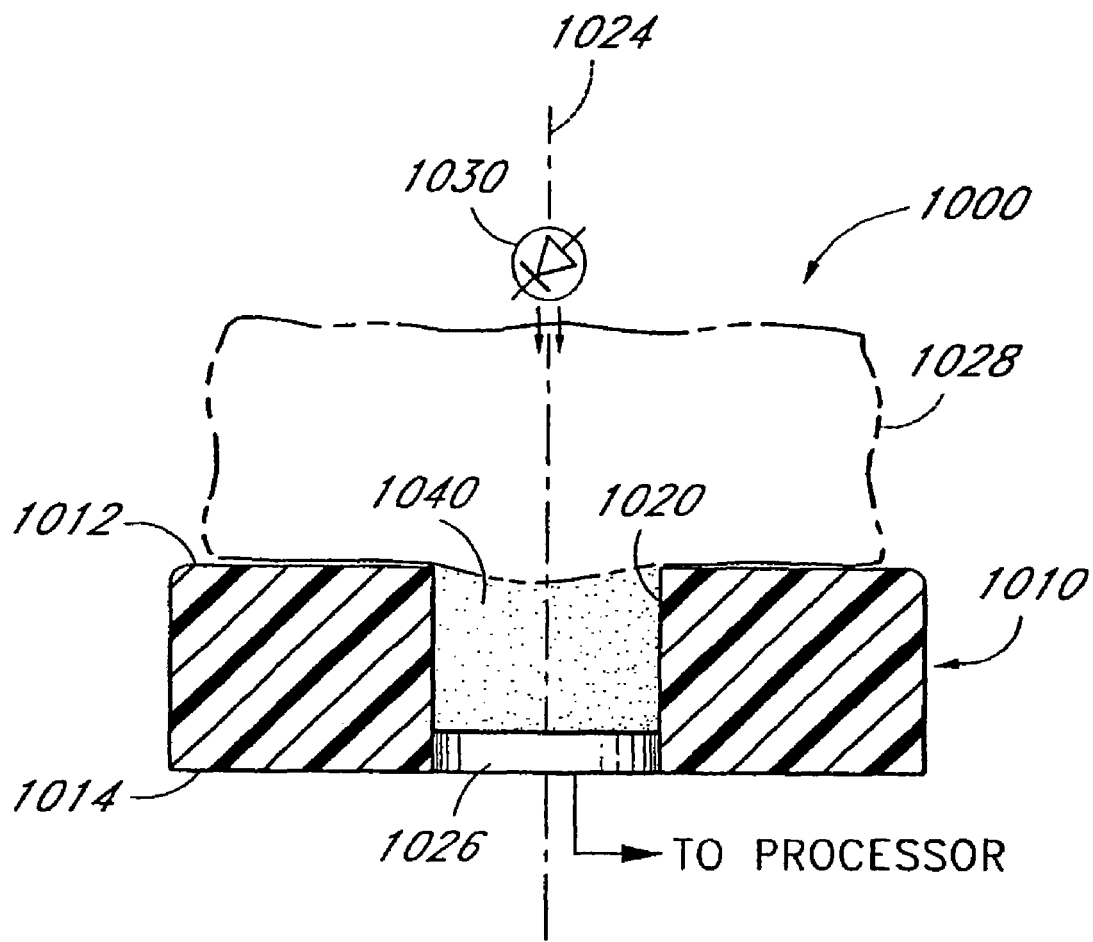
FIG. 25 is a cross-sectional view of a probe wherein the aperture is filled with a compressible scattering medium.

FIGS. 25-28 depict alternative embodiments of the present invention wherein an improved signal to noise ratio is observed in the received signal due to optical scattering effects. A probe 1000, shown in cross-section in FIG. 25, includes a base 1010, having a top 1012, a bottom 1014, and a forward and a rear end (not shown in FIG. 25). The base 1010 is preferably rigid and opaque to the wavelengths used in the probe 1000. An aperture 1020 is formed in the top 1012 of the base 1010. The aperture 1020 may be cylindrical (as shown in FIG. 25), conical, rectangular, or other shapes as called for by the specific application. The depth of the aperture 1020 may, for example, range from 0.5 mm to 10 mm, and is preferably in the range of 2-4 mm in depth in one embodiment, and more preferably in the range of 3-4 mm. Furthermore, the diameter of the aperture 1020 may range from 3 mm to 20 mm, as called for by the specific application. It has been found by the inventors that an aperture less than 0.5 mm in diameter does not obtain the benefits of the present invention.

A light source 1030 (e.g., one or more light emitting diodes) is affixed adjacent to material 1028 (e.g., an earlobe, finger, or other fleshy material), aligned along a central axis 1024 which passes substantially through the center of a photodetector 1026. The aperture 1020 is filled wholly, or in part, by a scattering medium 1040, which may, for example, comprise 2.2 pound polyurethane reticulated foam (although conformable plastic or scattering gels may also be employed). In general, the scattering medium may comprise one of a number of fixotropic materials (i.e., materials having two or more mixed materials which are conducive to scattering). Ideally, the scattering medium 1040 scatters but does not significantly absorb optical radiation at the operational red (e.g., 660 nm) and infrared (e.g., 940 nm) wavelengths for the oximeter. In other words, the material is clear to optical absorption, but still scatters light.

In operation, the light source 1030 (e.g., two LEDs in the present embodiment) emits optical radiation (e.g., in the red or infra-red spectrum range) which passes through the material under test 1028. The optical radiation is received by the photodetector 1026 after passing through the scattering medium 1040. The received optical radiation is scattered by the scattering medium 1040.

The scattering of the optical radiation within the scattering medium 1040 has been found to increase the signal-to-noise ratio of the received signal. It is believed that the signal-to-noise ratio is improved because there appears to be a reduced effect on the signal from any particular local region of the material 1028 (e.g., flesh). That is, by scattering the signal either prior to or posterior to the material interface, the signal is effectively spread over a larger area of the material 1028. Thus, perturbations of a locality within the area of exposure will have less effect with a scattered beam over a large area than with a more concentrated signal passing through that same locality. In this way, the effect of perturbations on the average signal is reduced. Also, the foam and plastic cover reduce optical decoupling and geometric variation in the optical light path during motion.

The scattering medium 1040 or plastic cover should be soft (i.e., highly compressible) so that the material 1028 does not significantly compress when the material 1028 presses against the scattering medium 1040. Compression of the scattering medium 1040 does not significantly alter the amplitude of the measured signal since the scattering medium is not highly absorptive of the optical radiation. Although conformable plastic covers may be used, reticulated foams provide improved optical coupling with flesh. This is because the reticulated foam provides contact in spots rather than across large areas of the flesh. If contact is made across large areas of flesh, microscopic droplets of perspiration or oil can form a layer between the flesh and the scattering medium 1040. This layer creates an impedance mismatch interface which is absorptive of the optical radiation. Of course, gels may also be used in accordance with the present invention. Such gels should not contain significant amounts of metal salts or silica because these materials absorb light.

The teachings of the present invention depart from conventional methods of improving optical signal-to-noise ratios. Commonly, lens assemblies which focus optical radiation are used to improve the signal-to-noise ratios of optical signals. However, oximetry by means of transmission or reflection is a non-imaging method of optical detection. Thus, the form of the image is not important for detection purposes. For this reason, scattering may be used as a method of improving optical signal quality; whereas, since scattering was thought to degrade signal-to-noise ratios of optical signals, previous methods have not employed optical scattering techniques.

Figure 26:
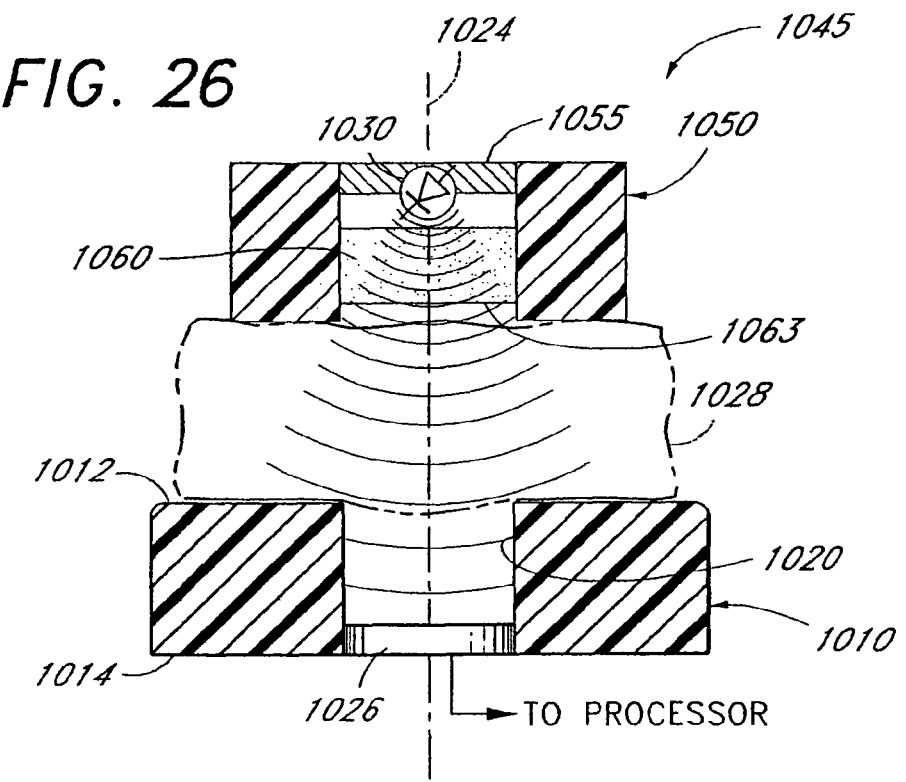
FIG. 26 is a cross-sectional view of a probe wherein the LED is spaced from the material to be measured by a transmission assembly having a scattering medium interposed between the LED and the material.
Figure 27:
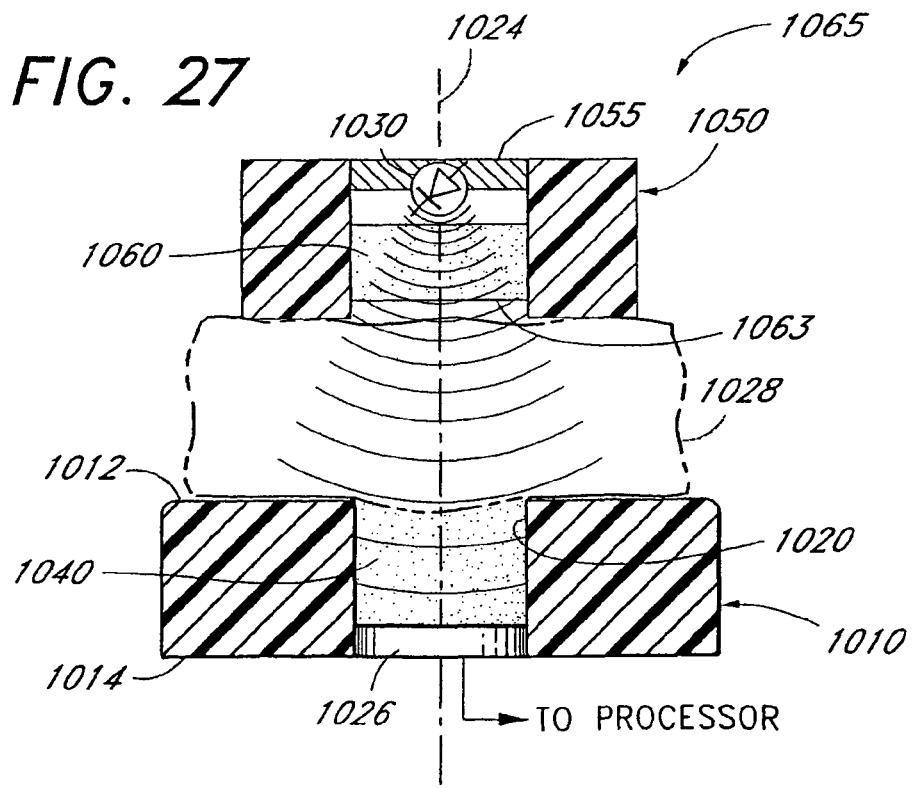
FIG. 27 is a cross-sectional view of a probe wherein a scattering medium is interposed between the LED and the material as well as between the material and the photodetector.

FIGS. 26 and 27 depict further alternative embodiments of the present invention wherein optical scattering is provided prior to the flesh interface, and both prior and posterior to the flesh interface, respectively. In FIG. 26, an oximetry probe 1045 further has a transmission assembly 1050 which secures the LED 1030 in place within a backing 1055. A scattering medium 1060, having a face 1063, is interposed between the LED 1030 and the material 1028. In the embodiment depicted in FIG. 26, the scattering medium 1060 does not contact the LED 1030; however, it should be understood that the scattering medium 1060 may contact one or both of the LED 1030 and the material 1028.

The scattering medium 1060 diffuses the optical radiation emitted by the LED 1030 over a wider area. Thus, the LED 1030, which is essentially a point source, is transformed into an evenly distributed source of light over the entire area of the face 1063 of the scattering medium 1060. The diffusion of the light over a wider area provides an improved signal-to-noise ratio.

Figure 28:
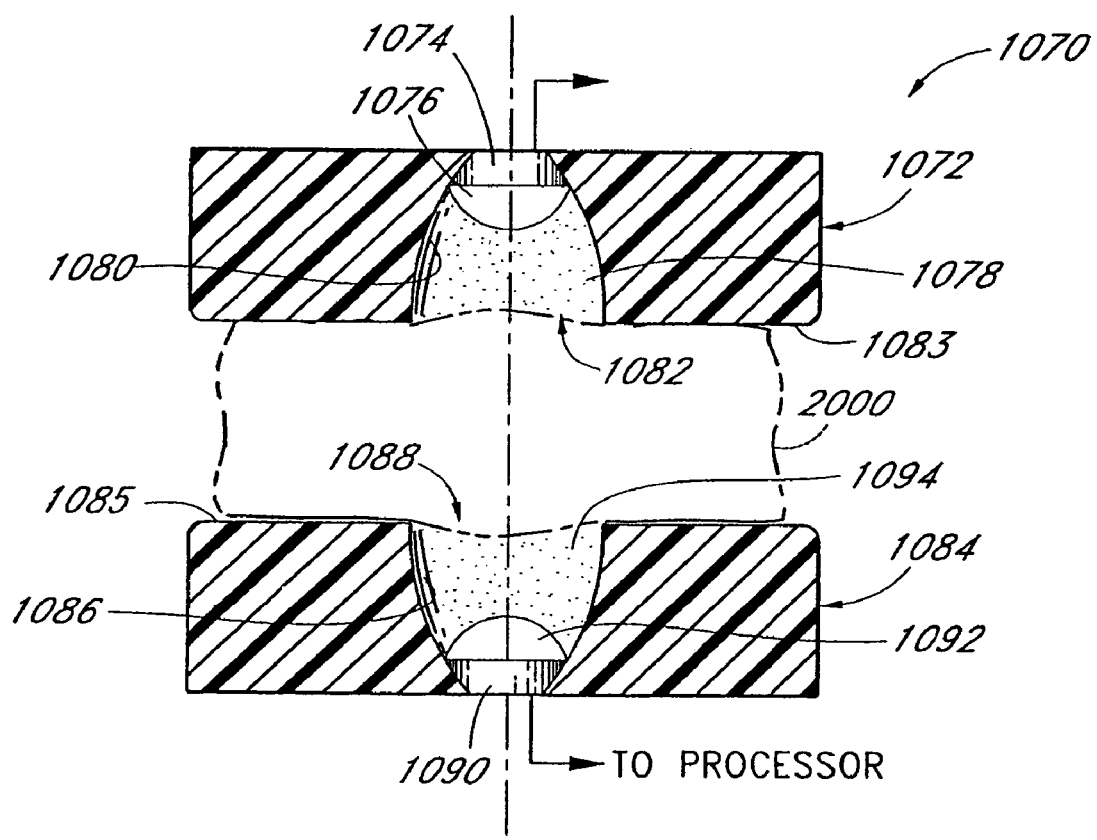
FIG. 28 is a cross-sectional view of a preferred embodiment of a probe in accordance with the present invention having an immersion lens for the photodetector and for the LED and having scattering medium interposed between the LED and the test material as well as between the test material and the photodetector.

As seen in FIGS. 26-28, the light is scattered. This is represented by the energy intensity contours rather than light path indicators. As recognized by the present inventors, the particular light path is not significant. The important aspect is the intensity of the light and the field of view of the photodetector and the light source. This will be explained further in connection with the embodiment of FIG. 28 utilizing an immersion lens.

The operation of a probe 1065 shown in FIG. 27 is essentially the same as that of the probe 1045, with the exception that the scattering medium 1040 is provided within the aperture 1020. It has been found that by providing a scattering medium on both sides of the material 1028, an improved signal-to-noise ratio is observed over the probes having a scattering medium on only one side of the material 1028.

FIG. 28 depicts a preferred embodiment of a probe 1070 in accordance with the present invention. As depicted in FIG. 28, the probe 1070 comprises a transmission assembly 1072, having a light source 1074, an immersion lens 1076, scattering medium 1078, a chamber 1080 defining an aperture 1082 along a support surface 1083 of the transmission assembly. A detector assembly 1084 is similarly configured with a support surface 1085, a chamber 1086 defining an aperture 1088 along the support surface 1085, a photodetector 1090, an immersion lens 1092 and scattering medium 1094. FIG. 28 further depicts a test material 2000 such a human tissue (e.g., a finger or earlobe) interposed between the light source assembly 1072 and the detector assembly 1084.

Several advantages are obtained from the particular configuration shown in FIG. 28. First, it should be understood that an economical way to fabricate the light source in the photodetector is to utilize small semiconductor LEDs and photodetectors. Such devices are very small, and therefore, have a very small field of view. The inventors have recognized that it is advantageous to improve the field of view of the photodetector and the LED because the surface of the tissue material 2000 at the aperture of the support surfaces is large compared to the surface of the semiconductor photodetector and LED. Thus, without enlarging the field of view of the photodetector and/or LED, much of the tissue material interface at the apertures is not utilized. As explained above, scattering of the light improves the received signal quality. An immersion lens for the photodetector and/or LED increases the field of view of the semiconductor photodetector and LEDs such that a substantial portion of the tissue material covering the apertures is within the field of view of the photodetector and/or LED.

Because imaging optics are not required due to the advantages of scattering, a significantly advantageous configuration is to utilize epoxy placed directly over the photodetector and/or over the LED in the form of a partial sphere which performs suitably as an immersion lens in the present embodiment. In one embodiment, the index of refraction of the epoxy is advantageously 1.56 in the present embodiment. The epoxy also acts to protect the photodetector and/or LED. The immersion lens can be formed by placing a bump of epoxy over the photodetector and the LED.

The immersion lens formed by a bump of epoxy over the photodetector and/or LED expands the field of view for the photodetector and LED in order to disperse the transmitted light energy over the tissue surface area at the apertures which is large relative to the surface of the optical elements. This assists in minimizing the effects of the relatively small optical details of the test materials (e.g., pores, fingerprint lines, sweat glands).

In the advantageous embodiment of FIG. 28, the scattering material 1080, 1086 is also placed in the chambers 1080, 1086 in order to enhance scattering of the light as explained above.

The cone shaped chambers 1080, 1086 depicted in FIG. 28 are also advantageous when the walls of the chambers are coated with a highly reflective material which does not absorb the light from the LED. The cone shape assists in reflecting the light energy away from the LED and toward the photodetector. All of these elements in combination form a particularly advantageous probe which can maximize the signal-tonoise ratio of the probe and minimize the effects of motion artifact on the received signal.

It should be understood that in alternative embodiments of the probe 1070 depicted in FIG. 28, elements could be removed and still obtain significant benefit. For instance, the detector assembly 1084 could remain the same with the light source assembly 1072 simply becoming an LED with no support surface and no chamber. Alternatively, the scattering media 1078, 1086 could be removed from either the chamber 1080 in the light source assembly 1072 or the chamber 1086 in the detector assembly 1082.

The light collecting lens, or other optical elements, could also be added to the chamber in any optical probe of the present invention to direct light onto the photodetector. However, the immersion lens provides better performance. The location of the photodetector and the LED may be interchanged in any of the above described probes. The bottom of any chamber formed in a base of an optical probe of the present invention can remain exposed, be covered by a material such as opaque tape, or be covered by a shell of base material without affecting the reduction of motion artifacts brought about by the chamber. Additionally, reflective measurements could be made with the probes of the present invention by mounting both the photodetector and LED on the base of the probe. Also, a plurality of LEDs or photodetectors could be mounted in the chamber or affixed to the material such that more than one signal may be measured at a time. Furthermore, any material having a chamber, with a detector or an LED mounted within the chamber, will reduce the effects of motion artifacts in non-invasive absorption (or reflection) measurements, according to the present invention.

Figure 29A:
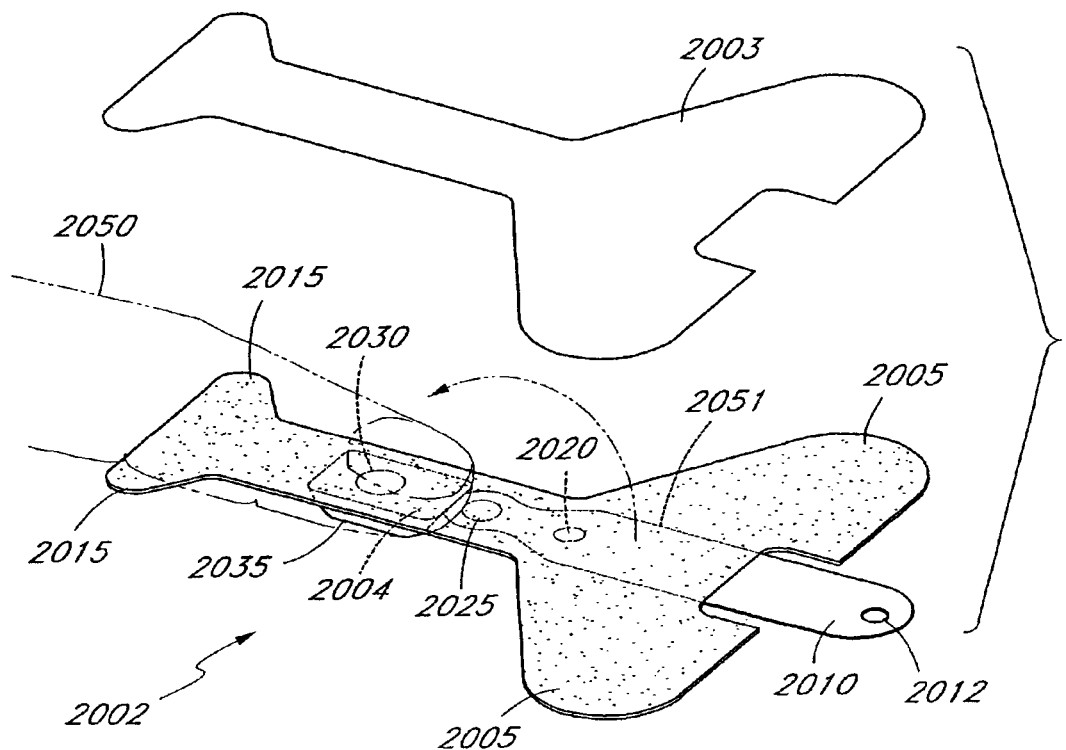
FIGS. 29A-29B are perspective views illustrating the use of one embodiment of the disposable optical probe of the present invention to measure the characteristics of a human fingertip.
Figure 29B:
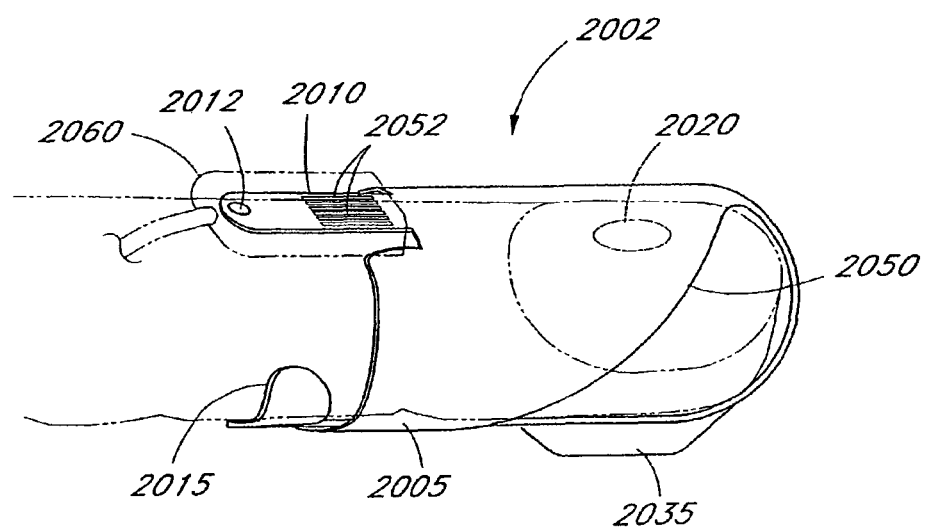

FIGS. 29A-29B depict one embodiment of a disposable, optical probe 2002, and the attachment of the optical probe 2002 on the fingertip 2050 of an adult patient. As shown in FIGS. 29A-B, the disposable optical probe 2002 is designed to fit comfortably onto a patient's fingertip. Advantageously, the optical probe 2002 is also configured to provide one or more of the following features: (i) minimization of undesirable movement with respect to the tissue under test (e.g., due to motion by the patient or contact of the probe 2002 with an object or surface); (ii) minimization or prevention of "light piping" (transmission) directly from the light source (e.g., light emitting diode) to the detector (e.g., photodetector), (iii) minimization of the detector and LED decoupling from the test site during motion, and (iv) the low noise chamber configuration described above.

As illustrated in FIG. 29A, the probe 2002 includes a central portion 2004, a pair of adhesive flanges 2005 extending from the central portion 2004, a connector portion 2010 situated between the flanges 2005, and a pair of smaller adhesive flaps 2015 extending from the central portion 2004 on the end of the optical probe 2002 opposite from the connector 2010. The probe 2002 further includes a connection aperture 2012 formed in the connector tab 2010, an emitter aperture 2020 with an emitter (e.g., a light-emitting diode) positioned within the central portion 2004 close to the connector portion 2010. A flex pocket 2025 is located within the central portion between the emitter aperture 2020 and a detector aperture 2030 which allows light to pass through the detector aperture 2030 to a detector assembly 2035. An adult fingertip 2050 is shown in phantom in FIG. 29A to illustrate the position at which the fingertip 2050 would be placed when the probe 2002 is to be fastened onto the fingertip 2050 for use.

Although not depicted specifically in FIGS. 29A-29B, the probe 2002 is fabricated from multiple layers, including a flex circuit layer, a MYLAR™ layer, a face stock tape layer, and other tape layers, depicted further in FIGS. 31-39.

FIG. 29B illustrates the probe 2002 fastened onto the fingertip 2050. As shown in FIG. 29B, the probe 2002 folds at the location of the flex pocket 2025 over the fingertip 2050 such that the flex pocket 2025 aligns with the very end of the fingertip and such that adhesive flaps 2005 fold downward (in the illustration of FIG. 29B) to wrap around the fingertip 2050 while the adhesive flaps 2015 fold upward (in the illustration of FIG. 29B) about a portion of the circumference of the fingertip 2050 to provide support. As shown in FIG. 29B, when the probe 2002 is folded about the fingertip 2050, the emitter located within the probe is spaced opposite the detector assembly 2035 such that light from the emitter passes through the emitter aperture 2020, through the finger 2050 and is incident upon the detector assembly 2035 through the detector aperture 2030.

Advantageously, when the probe 2002 is attached to the finger, the flex pocket 2025 is aligned at the tip of the finger 2050 so as to provide alignment of the probe 2002 on the fingertip 2050. The flex pocket 2025 also provides a highly flexible portion, thus providing for reduced movement of the detector and LED assembly with respect to the finger 2050 if the fingertip comes into contact with another object. This provides a more stable probe with increased motion resistance. In other words, the flex pocket also assists in minimizing perturbations in the detected signal due to movement of the detector and emitter with respect to the test tissue (e.g., the finger). Furthermore, the flex pocket 2025 reduces light piping since light is diverted around the circumference of the pocket.

In one embodiment, the flex pocket 2025 is formed to include an air cushion or other cushion material to further absorb contact of the probe 2002 with objects. In this manner, jarring of the probe 2002 in the event the fingertip 2050 moves slightly or in the event of contact of the probe to another surface is minimized.

The probe 2002 includes an internal flex circuit 2051 which acts as a spring-like shock absorber for the disposable probe. The flex circuit 2051 also assists in reducing shifting between the emitter 2021 and the detector assembly 2035 due to contact or motion by the patient. Thus, the internal flex circuit 2051, together with the flex pocket 2025 act to minimize the decoupling of the detector assembly.

FIG. 29B depicts a receiving connector portion 2060 which engages with contacts 2052 on the connector 2010 to provide an electrical connection between the optical probe 2002 and digital signal processing circuitry (not shown in FIG. 29C). The digital signal processing circuitry may be used to analyze the output of the detector within the assembly 2035. In one advantageous embodiment, the aperture 2012 catches onto a tab (not shown) within the connector 2060 to firmly secure the connector 2060 with the optical probe 2002. Once the optical probe 2002 is securely fastened to the fingertip 2050 and the connector provides an electrical connection between the optical probe 2002 and digital signal processing circuitry, signals are detected from the detector 2035 and transmitted to the processing circuitry via the connector 2060. Further details of the receiving connector portion 2060 are described in a patent application entitled "Patient Cable Connector" filed on the same date as the present application and assigned to the assignee of the present application, which application is incorporated herein by reference as if fully set forth.

Figure 30:
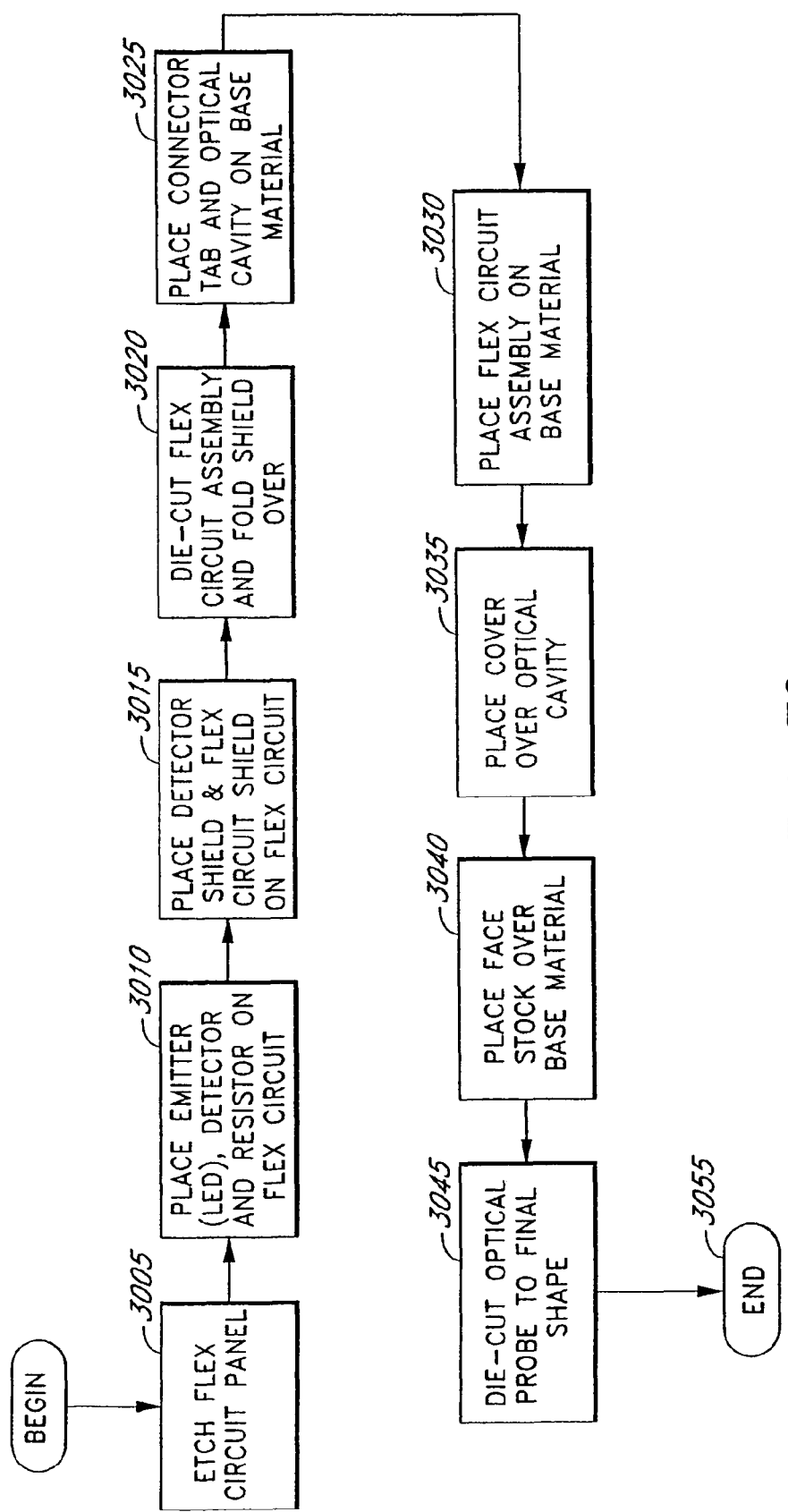
FIG. 30 is a flow chart which details a method of manufacturing the low-noise optical probe shown in FIGS. 29A-29B.
Figure 31A:
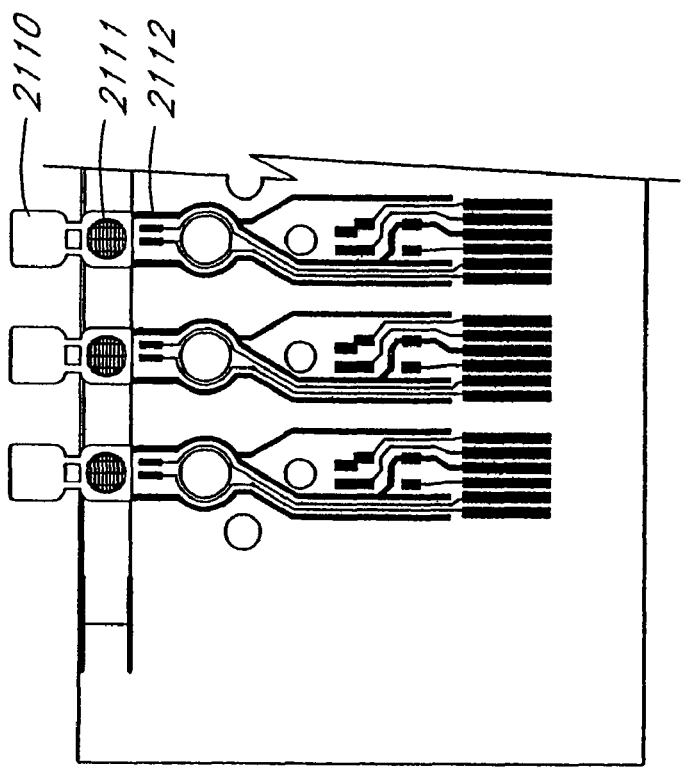
FIG. 31A depicts the placement of detector shields on pressure sensitive adhesive at detector end of the flex circuit.
Figure 31:
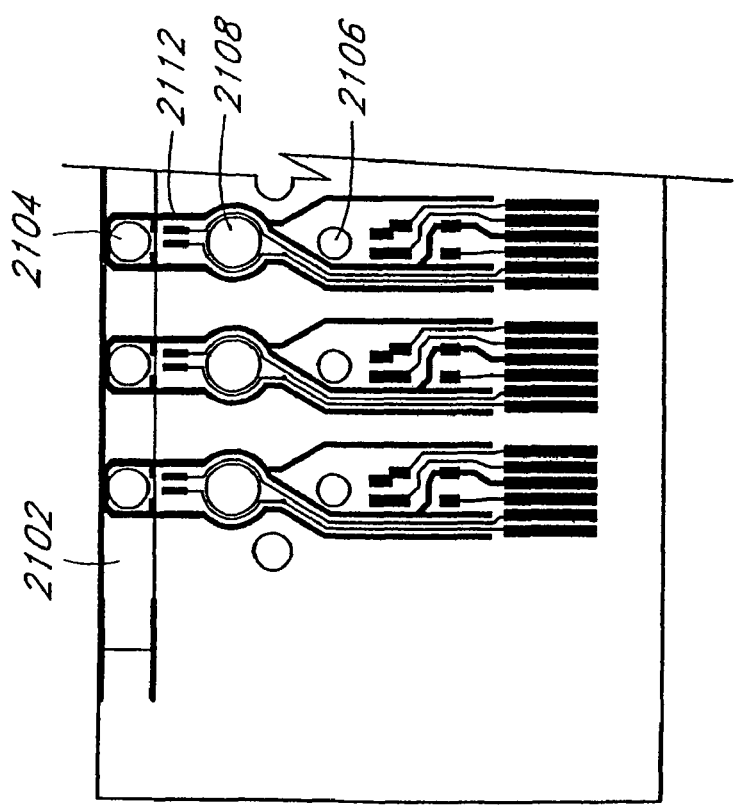
FIG. 31 depicts a first step of the manufacturing process, wherein multiple rows of flex circuit panels are etched onto a flex circuit panel comprising, for example, copper/MYLAR™, copper/CAPTON™, or conductive ink/MYLAR™.

FIG. 30 is a flow chart which illustrates the general steps in accordance with the present invention to manufacture a first embodiment of the disposable, optical probe 2002 depicted in FIGS. 29A-29C. A flex circuit is formed on a flex circuit panel as represented by an activity block 3005. In one advantageous embodiment, the flex circuit panel comprises a copper/MYLAR™ or copper/CAPTON™ laminant, or, alternatively, is formed by depositing a conductive ink on MYLAR™. For example, FIG. 31 depicts three etched flex circuits on a flexible circuit panel material. The flex circuits have been formed by etching in one preferred embodiment, and are comprised of one-ounce copper (approximately 1.3 mils) over 1 mil of MYLAR™ or CAPTON™.

After the flex circuit has been etched in an appropriate copper coated MYLAR™ substrate material, conductive pressure sensitive adhesive (PSA) 2102 is applied to the end of the flex circuits where the detector will be placed (hereinafter, the "detector end"), as depicted in FIG. 31. After the conductive PSA (made by 3M in the present embodiment, part No. 9703) is applied, a detector component window 2104 is cut through the conductive PSA 2102 and the flex circuit MYLAR™ base. An emitter component window 2106 is also cut through the flex circuit MYLAR™ base. A flex pocket hole 2108 is also cut through the flexible circuit MYLAR™ base. Next, detector shields 2110 are placed on the PSA at the end of the detector end of the flex circuit, as depicted in FIG. 31A.

In one embodiment, the detector shields are etched copper shields made of copper sheet. A grating 2111, which is about 80% open, is etched through the shields to allow light from the light source (e.g., LED) to transmit through the shield to a detector. The resultant shield has a frame of approximately 4 mils thickness and a grating of approximately 2 mils thickness. The shields provide a Faraday Shield for the detector.

The diffraction grating aligns with the detector component window 2104 in the flex circuit and, when the probe is assembled, with the detector aperture 2030 (FIG. 29A). The conductive PSA 2102 makes electrical connection between a flex circuit ground trace 2112 and the detector shield 2110 to connect the detector shield 2110 to ground.

Figure 31B:
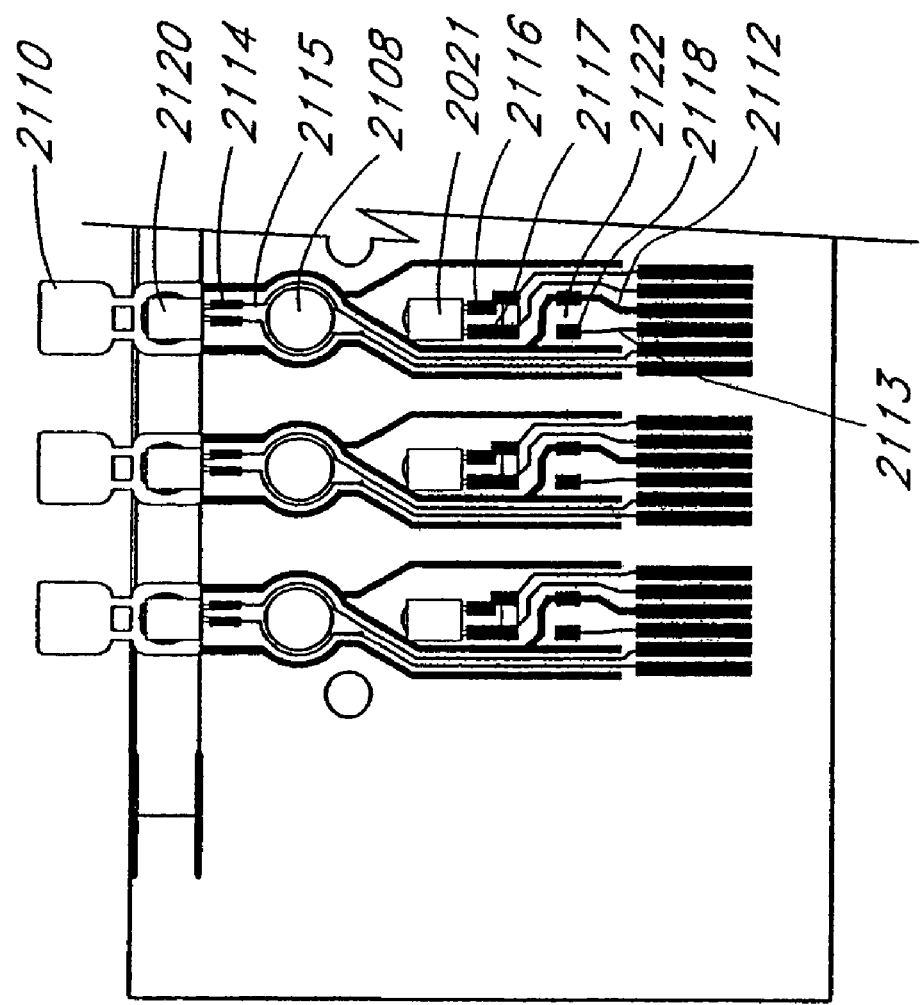
FIG. 31B illustrates a second step in the manufacturing process, wherein components are placed and soldered onto the flex circuits of FIG. 31.

In one preferred embodiment, low temperature solder paste is dispensed on contacts 2114, 2115, for the detector connections (FIG. 31B), on contacts 2116, 2117 for the emitter connections and on resistor pad 2118 for an identifying resistor. The emitter (LED) 2021, a detector 2120 and a resistor 2122 are placed and soldered in the appropriate positions on the flex circuits as depicted in FIG. 31B, and represented in an activity block 3010 (FIG. 30). The solder operation is preferably performed through a direct heat reflow of the low temperature solder. The emitter 2021 and detector 2120 are placed such that the transmission and detection field of view are through the detector and emitter windows 2104 and 2106 (FIG. 31).

In one embodiment, the resistor 2122 advantageously is connected to the ground trace on one end and a resistor signal trace 2113 at the other end. In another embodiment, the resistor 2122 is connected in parallel with the emitter 2021. The advantages of this parallel connection are explained in detail in copending application Ser. No. 08/478,493 entitled Manual and Automatic Probe Calibration, which is incorporated herein by reference as if fully set forth.

In one embodiment, the resistor 2122 provides a company identifier. In other words, the resistor 2122 can provide a value that specifically identifies that the probe is made by or for a particular patient monitoring company. As explained in copending application Ser. No. 08/478,493 the resistor can be read by lowering the voltage across the LED to a point where the LED is effectively off, thereby removing the LED from the circuit as a current draw.

As mentioned above, and as seen in FIG. 31B, the flex circuit has the aperture 2108 which is the aperture in the flex circuit forming a portion of the flex pocket 2025 of the probe 2002. In addition to the advantages of the high flexibility, this aperture 2108 through the flex circuit prevents a direct line of transmission between the emitter 2021 and the detector 2120. In other words, in use, light from the emitter 2021 which reaches the detector 2130 should pass through the medium under test (e.g., the finger or other tissue). Direct transmission of stray light from the emitter directly to the detector 2120 along a light conductive surface can cause erroneous readings, especially during motion. This direct transmission of light between the transmitter and detector is referred to herein as "light piping." That is, if the probe between the emitter 2021 and the detector 2120 has optical transmission properties, due to the construction or the material of the probe, stray light from the emitter may channel along the probe directly to the detector, without passing through the tissue material under test. Light piping is a heretofore unrecognized cause of noise and invalid signals from such optical probes. The aperture 2108 minimizes or prevents this "light piping" by preventing or minimizing a direct line of transmission from the emitter 2021 to the detector 2120 along the flexible circuit. Thus, the aperture 2108 provides benefits in the present invention of providing a highly flexible portion of the flex circuit, which reduces decoupling of the LED 2021 and the detector 2120 during motion (due, for example, to tapping on the finger tip), and preventing light piping between the emitter and the detector.

Once the appropriate circuit elements are placed and soldered onto the flex circuit, a flex circuit shield 2130, as depicted in FIG. 32A, is attached to the flex circuit panel as represented in an activity block 3015. The placement of the flex circuit shield 2130 with the flex circuit is depicted in FIGS. 32A and 32B. The flex circuit shield 2130 is advantageously constructed from MYLAR™ laminated with a thin conductive layer such as copper. In the present embodiment, the laminated MYLAR™ is made by ACUTEK.

In the present embodiment, the flex circuit shield 2130 has an insulator film 2132 depicted in double-cross hatching (made by Coating Sciences, part number P-341 in the present embodiment), a flex circuit shield conductive PSA strip 2133 (made by 3M, part no. 9703 in the present embodiment) and two non-conductive PSA strips 2134, 2135. As seen in FIG. 32A, the flex circuit shield 2130 has an emitter aperture 2136, two flex pocket apertures 2137, and a detector aperture 2138.

When the flex circuit shield 2130 is applied to the flex circuit, the insulator strip 2132 insulates the signal traces of the flex circuit from the metallization of the flex circuit shield 2130 to prevent short circuits. As further depicted in FIGS. 32A and 32B, when the flex circuit shield 2130 is positioned such that the apertures align with corresponding apertures on the flex circuit, the PSA strip 2135 provides bonding with the back of the flex circuit, the conductive PSA strip 2133 provides for bonding of one tab of the detector shield 2110 with the flex circuit shield 2130. The conductive PSA strip 2133 also provides connection of the flex circuit shield with the ground via the detector shield tab.

Figure 33B:
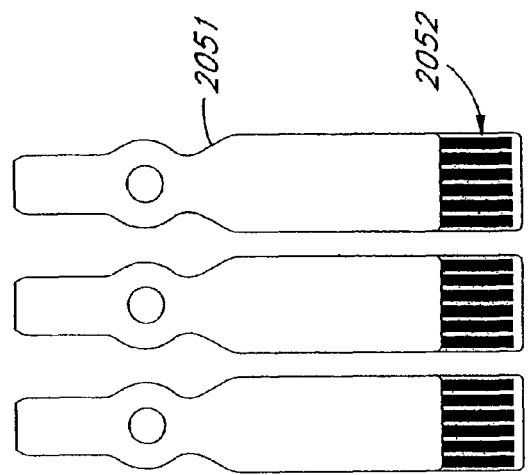
FIGS. 33A and 33B depict a fourth step of the manufacturing process, wherein the flex circuit assemblies are die cut and the shields are folded over the flex circuits to provide the completed flex circuit assemblies.
Figure 33A:
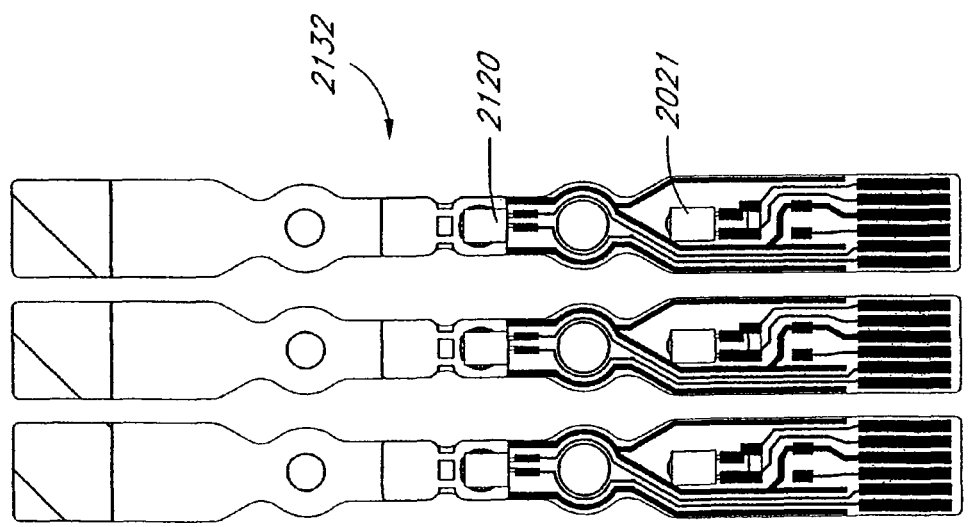

With the flex circuit shield in position, the flex circuit assembly 2132 (including the flex circuit, the emitter 2021, the detector 2120, the resistor 2122, and the shields 2110, 2130), are die-cut, as depicted in FIG. 33A. The flex circuit shield 2130, along with the detector shield 2110, is folded over the flex circuit as represented in an activity block 3020. The final flex circuit assembly 2051 is depicted in FIG. 33B.

Once folded, the insulator film 2132 prevents contact from the flex circuit traces to the metallization in the flex circuit shield 2130. The PSA strip 2135 bonds the flex circuit shield to the signal circuit side of the flex circuit. As depicted in FIG. 33B, the contact fingers 2052 remain exposed.

As illustrated in FIG. 34, a base material 2140 also forms a layer of the probe 2002. In one embodiment, the base material comprises Avery 3044 base material. Each side of the base material is coated with PSA adhesive (Coating Sciences, Inc., P-341 in the present embodiment). The back side (in reference to the illustration of FIG. 34) of the base material 214 is provided with the thin release liner 2003 (see FIG. 29A, not shown in FIG. 34), preferably made from a paper release liner or the like, as is well understood in the art.

In the present embodiment, the base material is transparent to the wavelength of the emitter 2021. The connector tab 2010 and an optical cavity 2150, are placed onto a first adhesive side of the base material 2140, as represented within an activity block 3025, and depicted in FIG. 34. The connector tab 2010 is advantageously formed of ABS styrene, and has the aperture 2012. The optical cavity 2150 may, for example, have the configuration for its walls in the shape of any of the above-disclosed bases (e.g., the bases 110, 1010, etc.) having a chamber formed therein. As depicted in FIG. 34, the optical cavity has a rectangular receiving receptacle 2152 adapted to receive the detector end of the completed flex circuit assemblies.

Figure 39A:
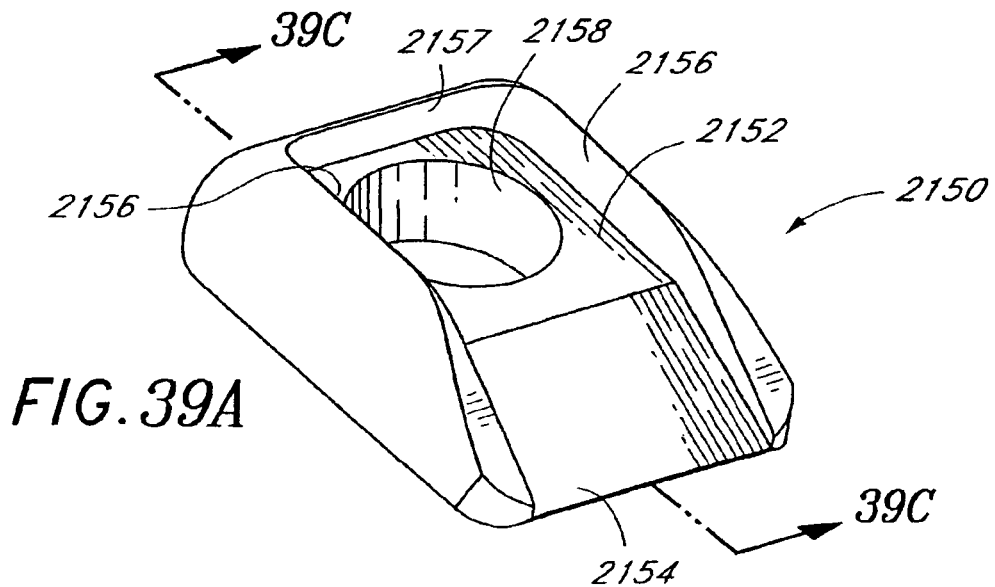
FIGS. 39A-39C illustrate an optical cavity in detail.
Figure 39B:
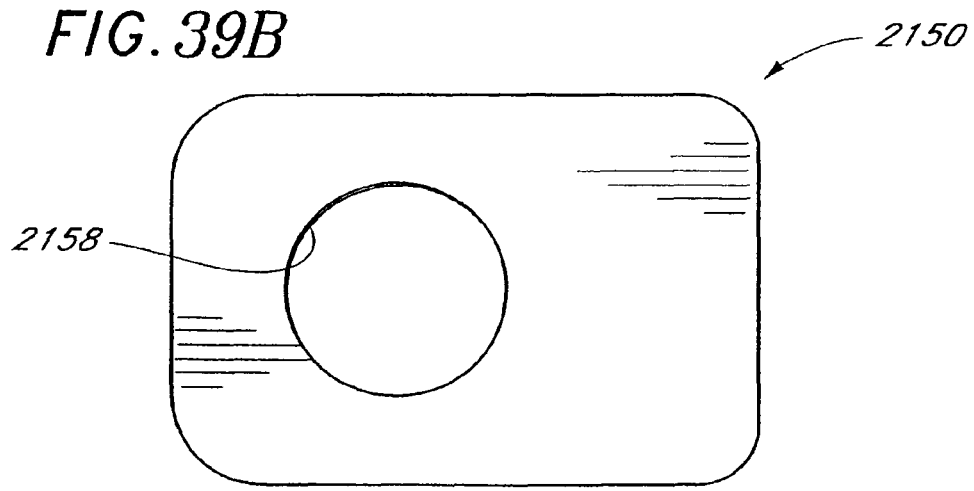
Figure 39C:
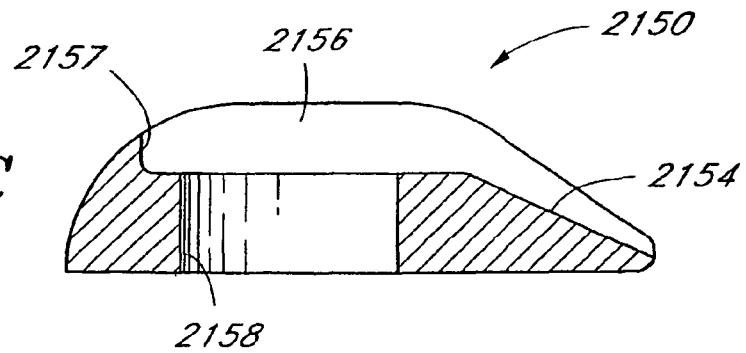

Additional detail of the optical cavity of the present embodiment of the probe 2002 is depicted in FIG. 39A-39C. FIG. 39A depicts a perspective view of the optical cavity 2150 for the probe 2002. FIG. 39B depicts a bottom view of the optical cavity 2150 and FIG. 39C depicts a cross sectional view along 39C-39C of FIG. 39A. The optical cavity 2150 is made from styrene in one embodiment. In one preferred embodiment, the optical cavity is coated with an optical coating that is opaque to ambient light. This can be on the inside walls of the optical cavity or over the exterior walls of the optical cavity, or the entire optical cavity can be coated. The opaque coating advantageously prevents or minimizes the transmission of ambient light from the surrounding environment which could be incident on the detector if the optical cavity is not opaque to ambient light. As an alternative to an opaque coating, the optical cavity can be made from a material that is opaque to ambient light.

Advantageously, the optical cavity 2150 has a wedge shape ramp 2154 as part of the rectangular receptacle 2152. As briefly mentioned above, the rectangular receptacle 2152 is adapted to receive the detector end of the flex circuit 2051. The wedge shaped ramp 2154 of the optical cavity 2150 provides a ramp for a smooth transition for the flex circuit 2051 between the surface of the base material to the rectangular receptacle table 2152.

Further illustrated in FIG. 40A are two side walls 2156 that runs along the side border of the rectangular receptacle 2152 and an end wall 2157 that runs between the two side walls 2156. These walls hold the flex circuit 2051 in position such that the detector 2120 aligns properly with an aperture 2158 in the optical cavity. Preferably, the flex circuit fits snugly between the side walls 2156 and against the end wall 2157.

In a preferred embodiment, the aperture 2158 has the configuration of the cavities describe above (e.g., cone-shaped, cylindrical in shape, or conical in shape, etc.).

Preferably, the PSA on the first adhesive side (FIG. 34) of the base material 2140 allows simple attachment of the optical cavity 2150 and the connector tab 2010 through the application of pressure.

After the connector tab 2010 and the optical cavity 2150 have been placed on the base material 2140, the flex circuit assembly 2051 is placed on top of the base material 2140, the connector tab 2010 and the optical cavity 2150 as depicted in FIG. 35 on one end. The detector end 2141 of the completed flex circuit assembly 2051 seats within the rectangular receptacle 2152 of the optical cavity 2150, as depicted in FIG. 35. Mounting of the completed flex circuit assemblies 2051 is represented in an activity block 3030 (FIG. 30).

With the detector end 2141 of the flex circuit assembly 2051 seated in the receptacle 2152 of the optical cavity 2150, the photodetector mounted to the flex circuit assembly 2151 is positioned to aligned with the aperture 2158 of the optical cavity 2150. In one embodiment, a hole, corresponding to the emitter aperture 2020 and the detector aperture 2030, is cut in the base material to correspond to the emitter 2021 and the detector 2120. However, in the present embodiment, the base material is transparent to the wavelength of the emitter 2021; therefore, holes are not provided through the base material 2140 for the detector and emitters.

As explained above in general, one of the advantages of the optical cavity 2150 is that fleshy tissue can enter the cavity without significant perturbation in the area of the field of view of the detector. Even if no hole is cut in the base material, if the base material chosen is very flexible, perturbation of the fleshy tissue in the field of view of the detector 2100 will be minimal due to the optical cavity aperture 2158, with the added benefit of not creating optical geometrical changes if the base material is not removed over the cavity.

A cover 2160 is placed over the optical cavity 2150 as represented in an activity block 3035, and shown in FIG. 36. The cover is advantageously a vacuum formed, cup-shaped cover. In the present embodiment, the cover is made from polypropylene. In one advantageous embodiment, the cover is opaque to ambient light. The opaque characteristic can be obtained from a coating or from the material of construction. The cover has flange 2162 which serves as a bonding surface with the base material. Advantageously, PSA on the base material provides the appropriate bond between the flange 2162 of the cover and the base material 2140.

A face stock 2170, advantageously constructed from a non-woven, flexible material, is placed over the base material 2140. In an alternative embodiment, a woven, flexible material is acceptable. In the present embodiment, the face stock 2170 comprises 3M part no. 9908. The face stock preferably has an aperture 2171 to allow the cup portion of the cover 2160 to protrude through the face stock. The face stock 2170 covers the flange portion 2162 (shown in dotted lines in FIG. 37) of the cover 2160. This assists in holding the cover 2160 firmly in place. Because the base material has PSA on the side to which the face stock is applied, pressure applied to the face stock bonds the face stock with the base material. In the present embodiment, the face stock 2170 also has PSA on one side (side down in FIG. 37). The face stock is cut such that the connector tab 2010 and the connector traces 2052 of the flex circuit remain exposed. This manufacturing step is represented in an activity block 3040 and is depicted in FIG. 37.

In addition, to a cutout 2172 in the face stock 2170 and the base material 2140 provide a slot on each side of the connector tab 2010 and the connection traces end of the flex circuit assembly 2051. These slots are adapted to receive walls of the connector receptacle 2060 (see FIG. 29B) for stability.

Finally, the optical probe is die-cut to a final shape as depicted in FIG. 38 and represented in an activity block 3045 (FIG. 30). The manufacturing method is complete, as represented within an activity block 3055. Removal of the release liner 2003 on the base material 2140 allows for placement on the digit of a pediatric or adult patient as depicted in FIGS. 29A-29B.

Figure 41:
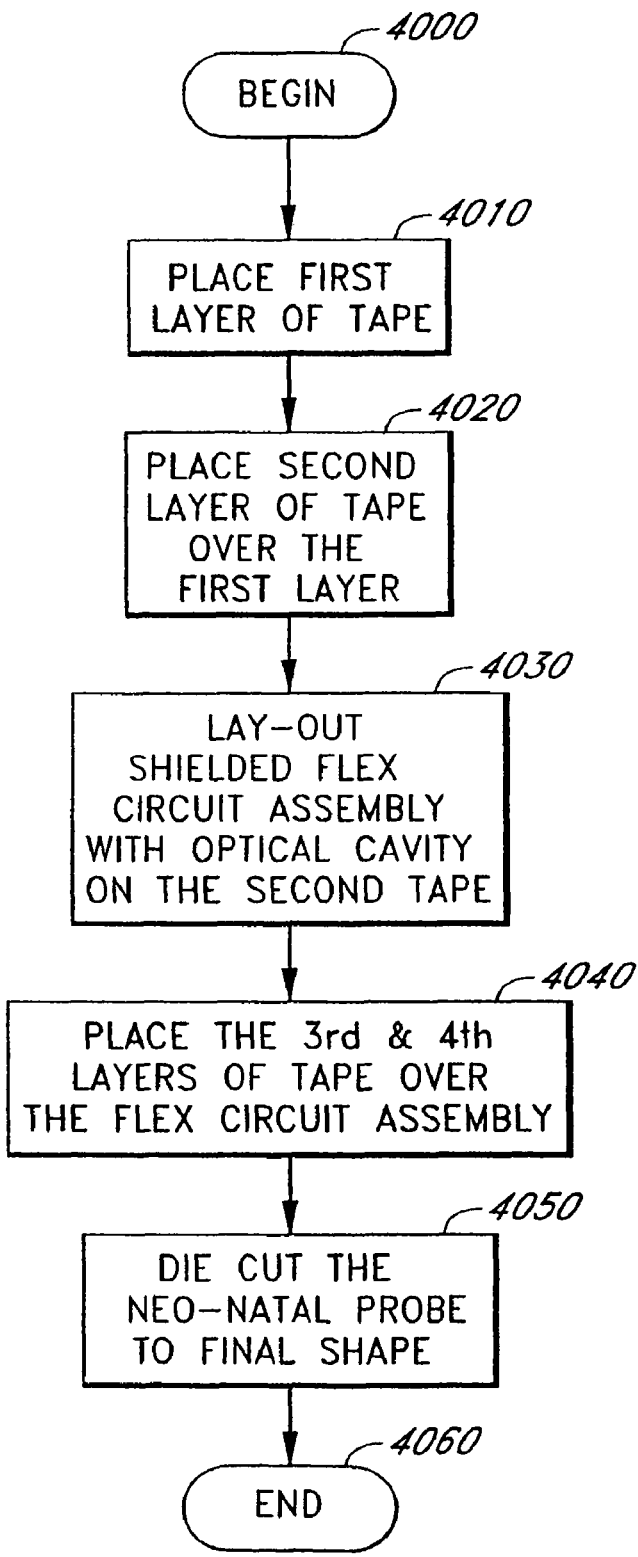
FIG. 41 is a flow chart which details the general method used for manufacturing a neonatal disposable optical probe in accordance with a second embodiment of the present invention.

Another embodiment of a low noise optical probe 2200 is depicted in FIG. 40A. This embodiment is advantageous for use with neonates, as will be further described below. FIG. 41 is a flow chart which details the general method used for manufacturing a neonatal disposable optical probe 2200 in accordance with this second embodiment of the present invention.

As with the previous embodiment, the neonatal probe 2200 is constructed of several layers. A first tape layer 2210 is laid out as represented in an activity block 4010, and depicted in FIG. 42. Advantageously, the first tape layer 2210 is constructed from release liner material. The first tape layer 2210 has adhesive portions on one side for adhesion to the tissue material under test, as will be further understood below. In the present embodiment, the release liner is a conventional paper type release liner for the medical industry.

In a preferred embodiment, the first tape layer 2210 has a first portion of adhesive 2212 and a second portion of adhesive 2213 which provide adhesion in the area of the detector and emitters. In the present embodiment, the adhesive portions 2212, 2213 are made from 3M part number MED 3044, which is a medical quality two-sided PSA material. This material is transparent to the wavelength of the emitter in the probe 2200, and therefore, a thru hole is not required. However, a thru hole, such as the thru hole 2211 could be provided in one embodiment.

A second tape layer 2220 is placed over the first tape layer as represented in an activity block 4020, and depicted in FIG. 43. The second tape layer 2220 includes an emitter aperture (thru hole) 2222 and a detector aperture 2224, which provide windows for the detector and emitters. In the present embodiment, the second tape layer is made from a non-woven face stock material, with PSA on one side. In the present embodiment, the second tape layer 2220 comprises part number 9908, made by 3M. In the illustration of FIG. 43, the adhesive side is up.

Figure 44A:
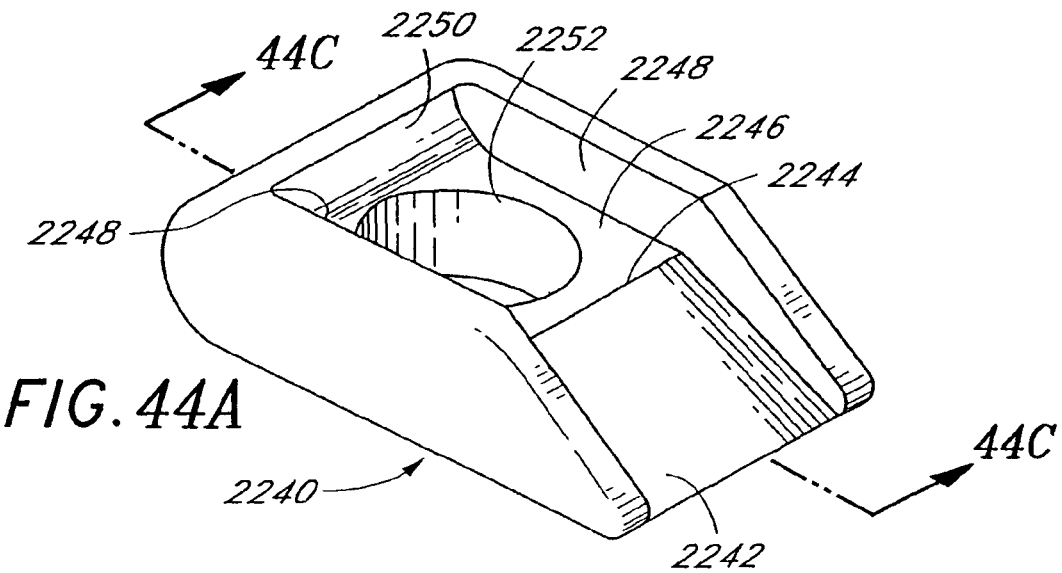
FIGS. 44A-44C illustrate an optical cavity in detail.
Figure 44B:
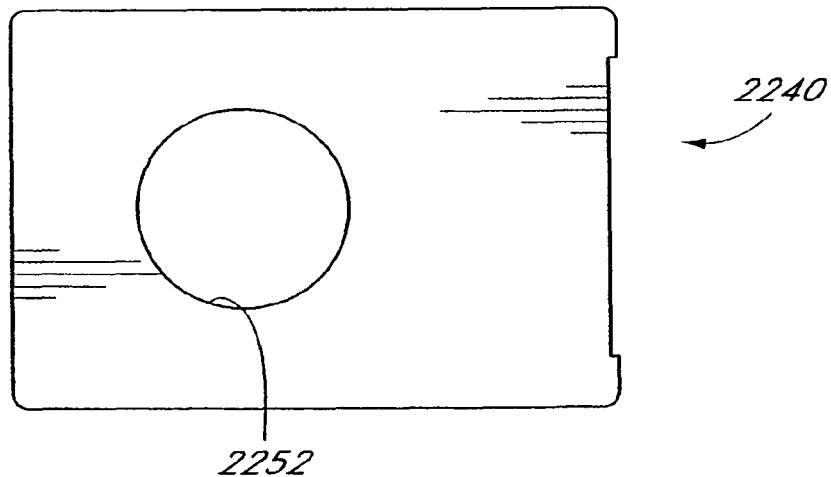
Figure 44C:
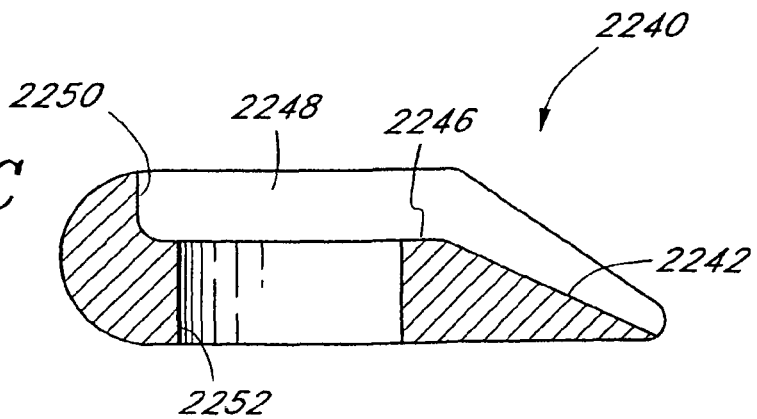

An optical cavity 2240 is placed onto the second tape as shown in FIG. 43 and represented in an activity block 4030. One preferred embodiment of the optical cavity 2240 is illustrated in additional detail in FIGS. 44A-C. FIG. 44A depicts a perspective view of the optical cavity 2240. FIG. 44B depicts a bottom plan view of the optical cavity 2240, and FIG. 44C depicts a side cross-sectional view through 44C-44C of FIG. 44A. As with the embodiment of FIG. 39A-C, the optical cavity 2240 is made from styrene or ABS or the like in one embodiment. In one preferred embodiment, the optical cavity 2140 is coated with an optical coating that is opaque to ambient light. This can be on the inside walls of the optical cavity or over the exterior walls of the optical cavity, or the entire optical cavity can be coated. The opaque coating advantageously prevents or minimizes the transmission of ambient light from the surrounding environment which could be incident on the detector if the optical cavity is not opaque to ambient light. As an alternative to an opaque coating, the optical cavity can be made from a material that is opaque to ambient light.

Advantageously, the optical cavity 2240 has a wedge-shaped ramp 2242 as part of a rectangular receptacle 2244. The rectangular receptacle 2244 is adapted to receive the detector end of a flex circuit, as further explained below. The wedge-shaped ramp 2242 of the optical cavity 2240 provides a ramp for a smooth transition for the flex circuit between the surface of the second tape layer 2220 to a rectangular receptacle table 2246.

Further illustrated in FIG. 44A are two side walls 2248 that extend along the side border of the rectangular receptacle 2244 and an arcuate end wall 2250 that extends between the two side walls 2248. These walls hold the flex circuit in position such that the detector aligns properly with a aperture 2252 in the optical cavity 2240. Preferably, the flex circuit fits snugly between the side walls 2248.

In a preferred embodiment, the aperture 2252 has the configuration of the cavities describe above in general (e.g., cone-shaped, cylindrical in shape, conical in shape, etc.)

A flex circuit 2254 is depicted in detail in FIGS. 45A-B. As depicted in FIG. 45A, a flex circuit is formed on a flexible substrate 2255. In the present embodiment, the flexible substrate advantageously comprises 3 Mil polyester (e.g., MYLAR™) with copper coating on 1 side. In the present embodiment, the copper coating is ½ OZ. copper coating. The circuit pattern is etched such that the circuit traces of copper remain on a signal side of the flex circuit 2254 after etching. From this etching standpoint, the flex circuit 2254 is made in the same fashion as the flex circuit assembly 2051 of the adult probe 2002.

Once the circuit is etched, it is placed on a bottom shielding layer 2256, depicted in FIG. 45A. In one embodiment, the shielding comprises a metallized MYLAR™ shield, with one side metallized. The metallic side is positioned against the back side of the flex circuit substrate 2255. Conductive PSA bonds the flex circuit substrate 2252 with the bottom shielding layer 2256 through connection 2251 connects the bottom shield metallization to ground from the ground trace 2253. The bottom shielding layer 2256 has an emitter aperture corresponding to the emitter aperture 2252 in the optical cavity 2240 and the emitter aperture 2257 in the flex circuit 2254. The bottom shielding layer 2256 extends (extension labeled 2258 in FIG. 45A) beyond the detector end of the flex circuit 2250. In an alternative embodiment, the back side of the flex circuit 2254 has a metal coating, such as copper. This provides appropriate shielding. Thus, the first shielding layer could be eliminated in an alternative embodiment.

A detector shield 2260, such as the detector shield 2110 of the probe 2002 (FIG. 32), is bonded to the signal trace side of flex circuit 2254, as depicted in FIG. 45B. Next, a detector 2272 is placed using low temperature solder, as with the previous embodiment, such that the detector field of view is through the grating 2261 in the detector shield 2260. The detector shield 2260 is then folded over the detector in order to provide a Faraday shield, as with the previous embodiment.

The extension 2258 of the first shielding layer 2256 is then folded over and conductive PSA is used to bond the metallized side of the bottom shielding layer 2256 to the detector shield 2260. This connects the detector shield to ground. The emitter 2270 is also placed using the low temperature solder.

In one advantageous embodiment, a resistor 2262 is also placed either in parallel with the emitter or is provided with its own connection trace. The embodiment of FIG. 45A depicts an embodiment with a separate connection trace 2263 for the resistor 2262.

A top shielding layer 2268 is placed to shield the signal side of the flex circuit, as depicted in FIG. 45C. In the present embodiment, this second shielding layer 2268 comprises the same material as the first shielding layer 2256. The second shielding layer 2268 is bonded to the detector shield 2260 using conductive PSA which couples the second shielding layer 2268 to ground. The second shielding layer 2268 covers the entire flex circuit and is bonded to the flex circuit 2254 using PSA.

The flex circuit assembly 2254 of FIG. 45 used in the neonatal probe 2200 is constructed with a unique V-configuration. The emitter 2270 is at the tip of one branch, a detector 2272 is at the tip of the other branch, and a connector tab 2274 (substantially the same as the connector tab 2010) is attached at the base of the "V."

The optical cavity 2240 is substantially the same as the optical cavity 2150. In addition, the detector 2272 and the emitter 2270 are substantially the same as the detector 2120 and the emitter 2021.

Figure 46:
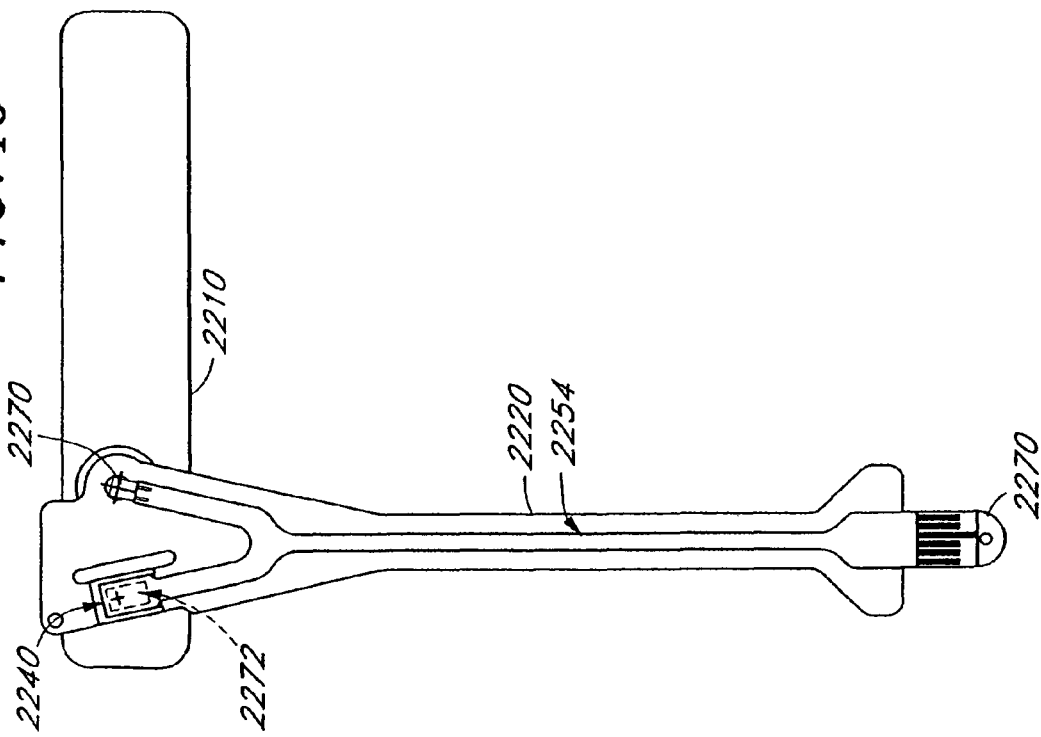
FIG. 46 illustrates a third step in the manufacturing process for the neonatal probe, wherein the flex circuit is laid out with a connector as well as an optical probe onto the second layer of tape.

Once the shielded flex circuit assembly 2254 is completed, the completed flex circuit assembly is placed onto the second tape 2220, as depicted in if FIG. 46. The flex circuit 2250 is positioned such that the emitter 2270 and the detector 2272 have a field of view through the respective apertures 2222, 2224 in the second tape layer 2220.

Figure 47:
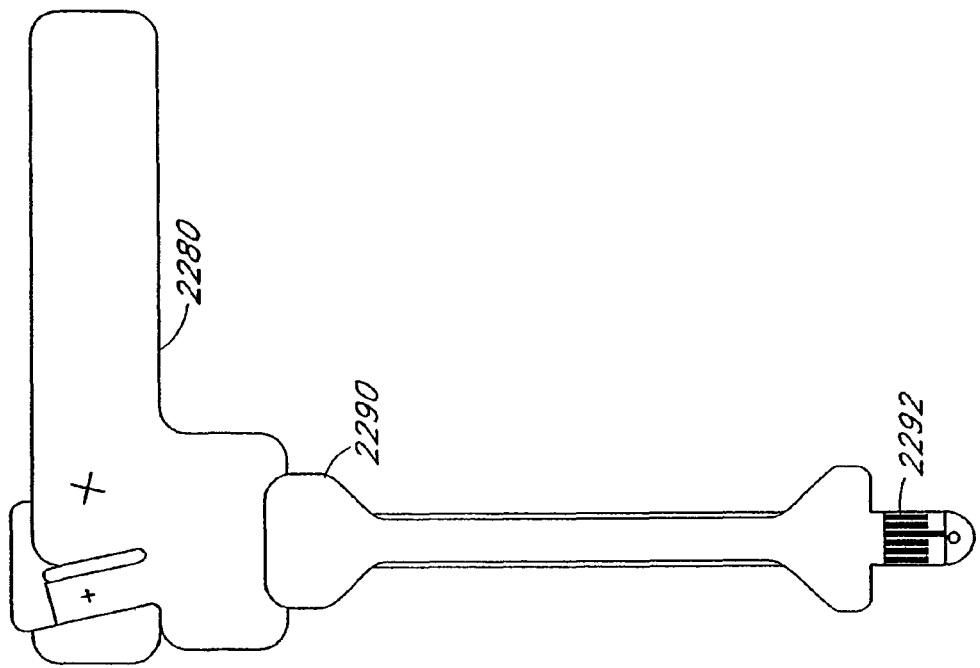
FIG. 47 illustrates a fourth step in the manufacturing process of the neonatal probe, wherein the third and fourth layers of tape are laid over the flex circuit.

Once the flex circuit assembly is placed, third and fourth layers of tape 2280, 2290 are placed over the flex circuit assembly 2254 as represented within an activity block 4040 and depicted in FIG. 47. The third and fourth tape layers 2280, 2290 are made from the non-woven face material such as that made by 3M as part number 9908. The third and fourth tape layers 2280, 2290 have PSA on the side which bonds to the assembly made up of the first tape layer 2210, the second tape layer 2220 and the flex circuit assembly 2254. As depicted in FIG. 47, the fourth tape layer 2290 is configured to allow connection traces 2292 of the flex circuit to remain exposed.

Figure 48:
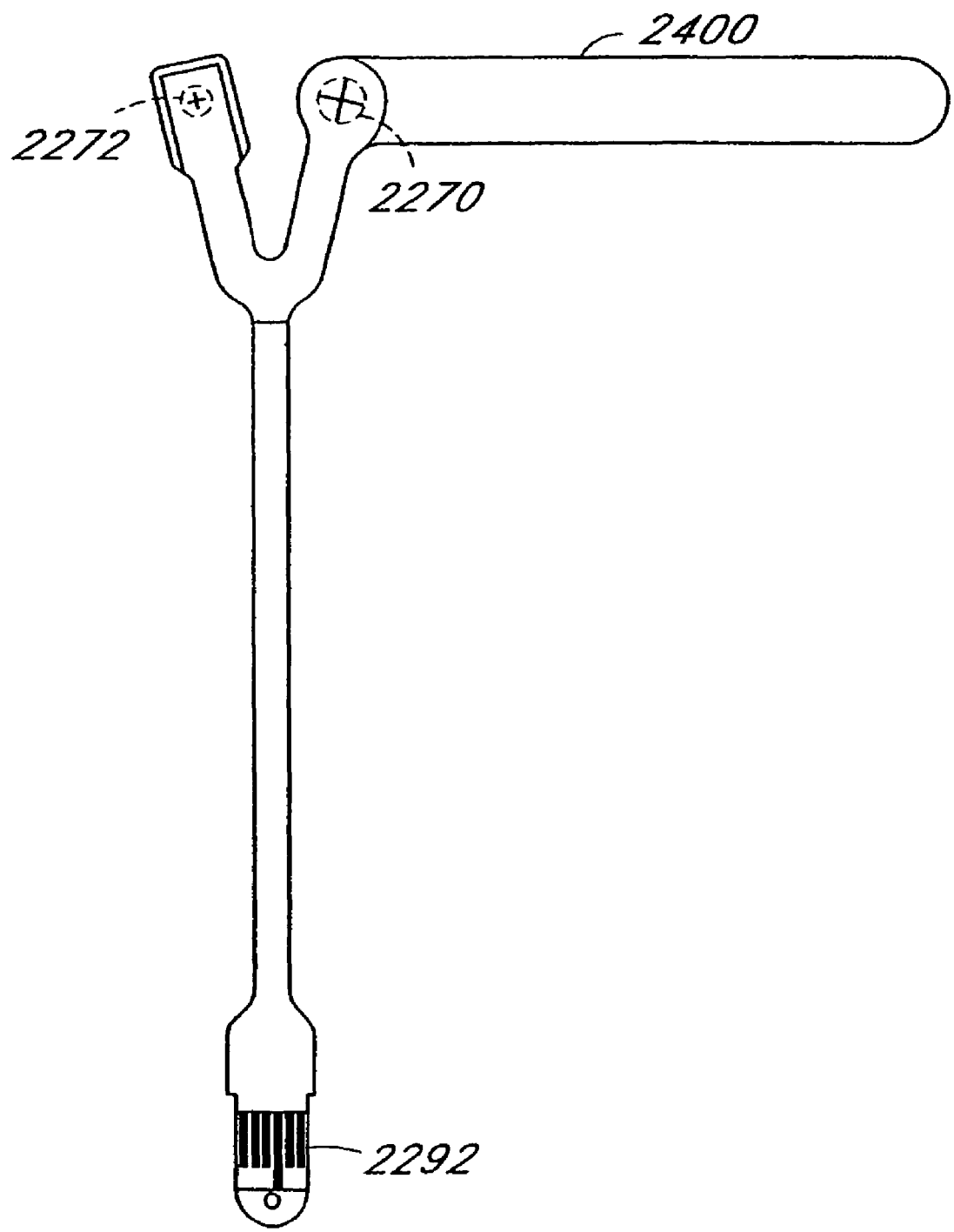
FIG. 48 illustrates a fifth step in the manufacturing process wherein the neonatal probe is die-cut to the final shape.

Finally, the neonatal disposable probe 2200 is die-cut to a final shape as represented within activity block 4050 and depicted in FIG. 48. The manufacturing method is then complete as represented within an activity block 4060.

FIGS. 40A and 40B illustrate the neonatal probe being attached to a baby's foot (shown in phantom). The finger is placed on the detector branch of the probe 2200. The emitter branch is then positioned so that the emitter 2270 is directly above the detector 2272 with the foot in-between. An adhesive strap 2400 (which was die-cut from the first tape layer 2210 and the third tape layer 2280) is then wrapped around the foot to secure the relative position of the emitter 2270 and detector 2272. It should be appreciated that the adhesive material selected to coat the adhesive strap should not be so strong as to tear or bruise the skin of a newborn baby. The connector 2060 subsequently establishes electrical connection between the probe 2200 and digital signal processing circuitry via the connector tab 2294.

The unique V-configuration of the neonatal probe embodiment of the present invention (e.g., as displayed in FIG. 49) is particularly advantageous for use in applications where the optical probe is used on neonates. The V-configuration allows the probe to be used on many different sizes of monitoring sites (e.g., feet, hands, etc.) for a neonate. With conventional wrap-around embodiments, the spacing of the detector and emitter is fixed, thus making the use of the probe for different sized monitoring sites more difficult. In addition, the V-shaped design allows for the use of the probe on various body parts. For instance, the probe 2200 could be attached to the nose or ear of the neonate. The probe 2200 could also be used as a reflectance probe with the probe attached to the forehead of the neonate, or other relatively flat skin surface. Thus, the V-design provides for the adaptation of the probe for many different places on the neonate body.

Figures 49, 50:
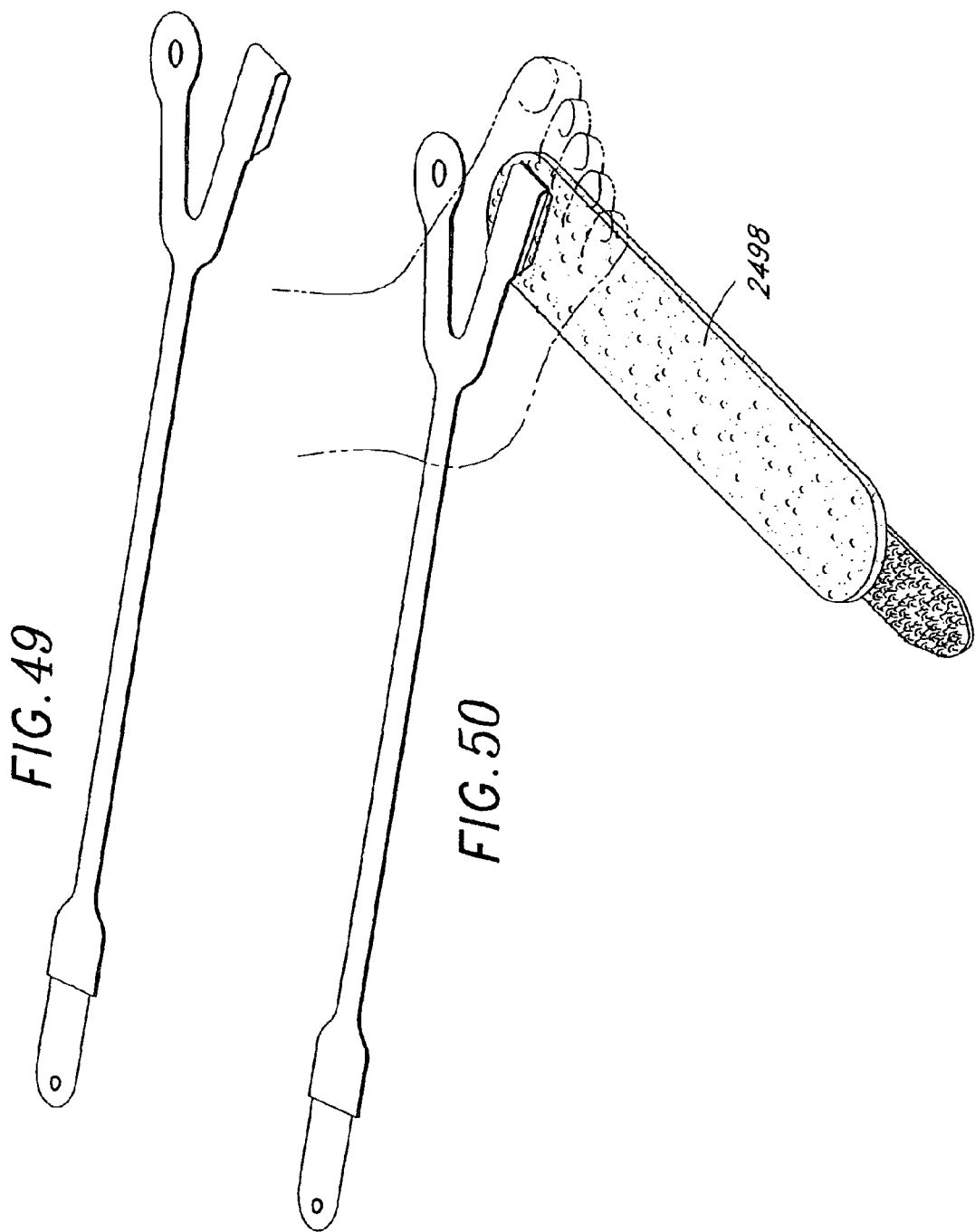
FIGS. 49 and 50 depict an alternative embodiment of the neonatal probe wherein a soft, hospital wrap is used to affix the probe to a newborn's foot.

An alternative embodiment of the V-configuration is depicted in FIG. 49. In the embodiment depicted in FIG. 49, the adhesive extension 2400 (FIG. 48) is not provided. In this embodiment, the probe can be used with conventional medical tape or the like, or can be provided such that the adhesive 2212, 2213 (FIG. 42) in the area of the detector and emitter hold the probe in place. Alternatively, a soft, spongy, hospital wrap (e.g., a POSEY wrap) 2498 can be configured to firmly hold the probe to a digit as depicted in FIG. 50.

Figure 51:
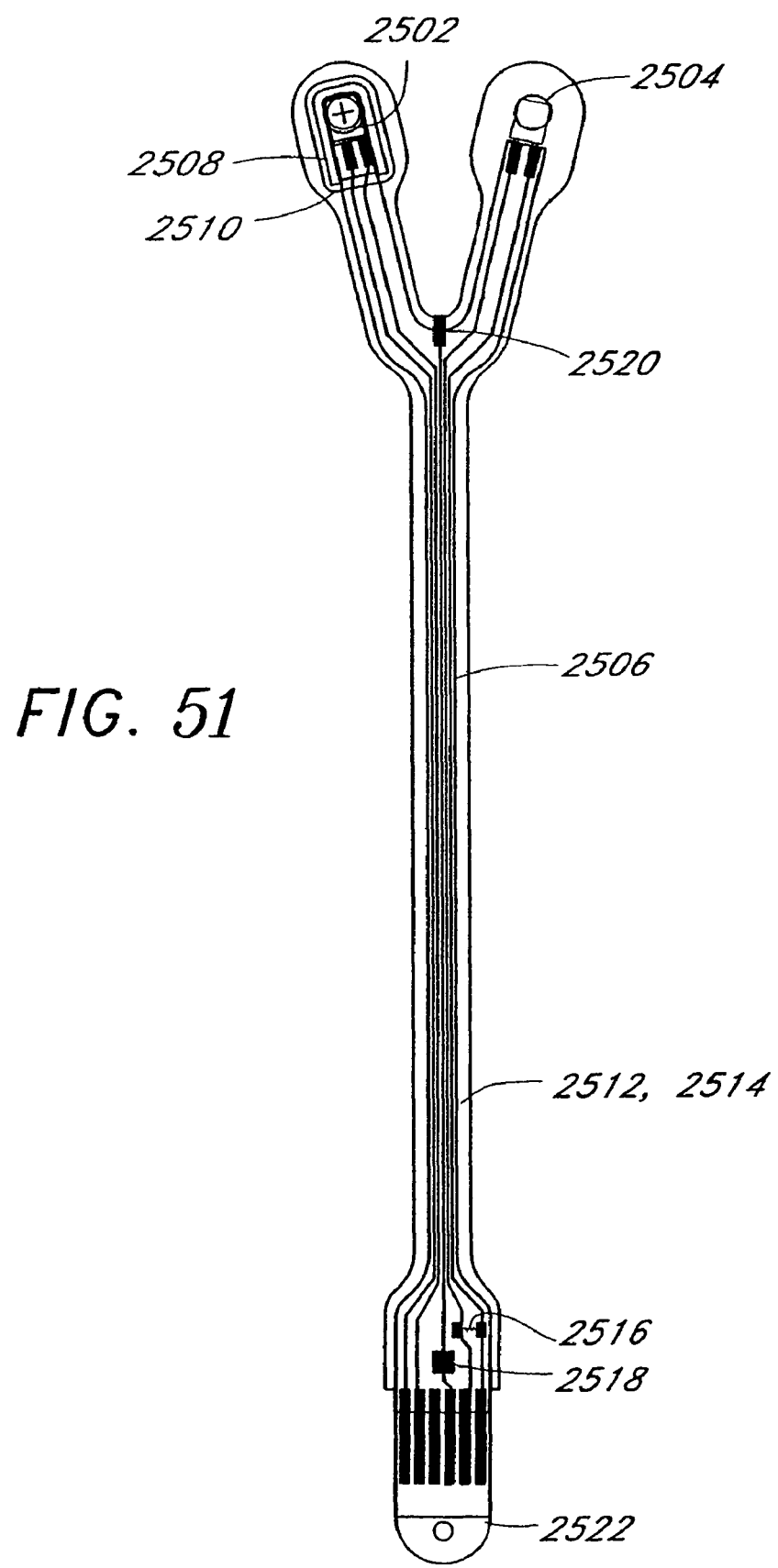

Another embodiment of the method of making the neonatal probe is illustrated in FIGS. 51-55. An X-ray type view of the alternative embodiment 2500 is depicted in FIG. 51. As illustrated in FIG. 51, the probe 2500 has a detector 2502, an emitter 2504, a flex circuit 2506, a low noise cavity 2508 and a cover 2510 for the optical cavity 2508, top and base tapes 2512, 2514, an identification resistor 2516, thru connections 2518, 2520, and a connection tab 2522. This embodiment of the probe is depicted without the tape extension, such as the extension 2400 (FIG. 48), but could include a tape extension in one embodiment. The overall configuration of the finished probe 2500 is nearly identical to the probe of FIG. 49. However, the shielding is different, the optical cavity has a cover, and the probe 2500 is constructed using two tapes instead of four. The construction of this embodiment of the probe 2500 is similar to the adult probe from the standpoint of the tape-up.

Figure 52A:
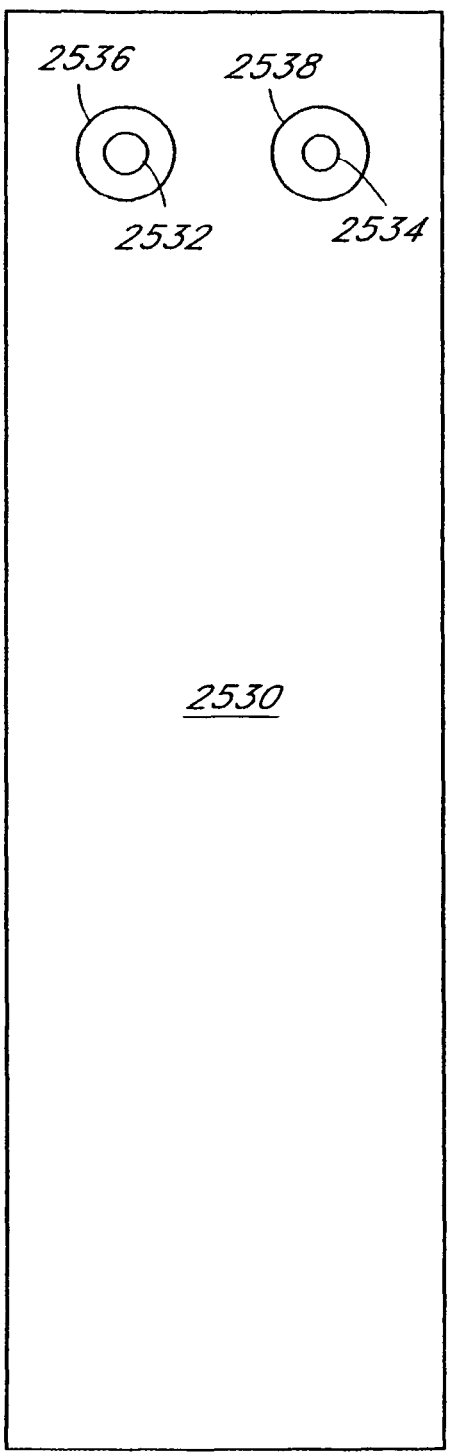
Figure 52B:
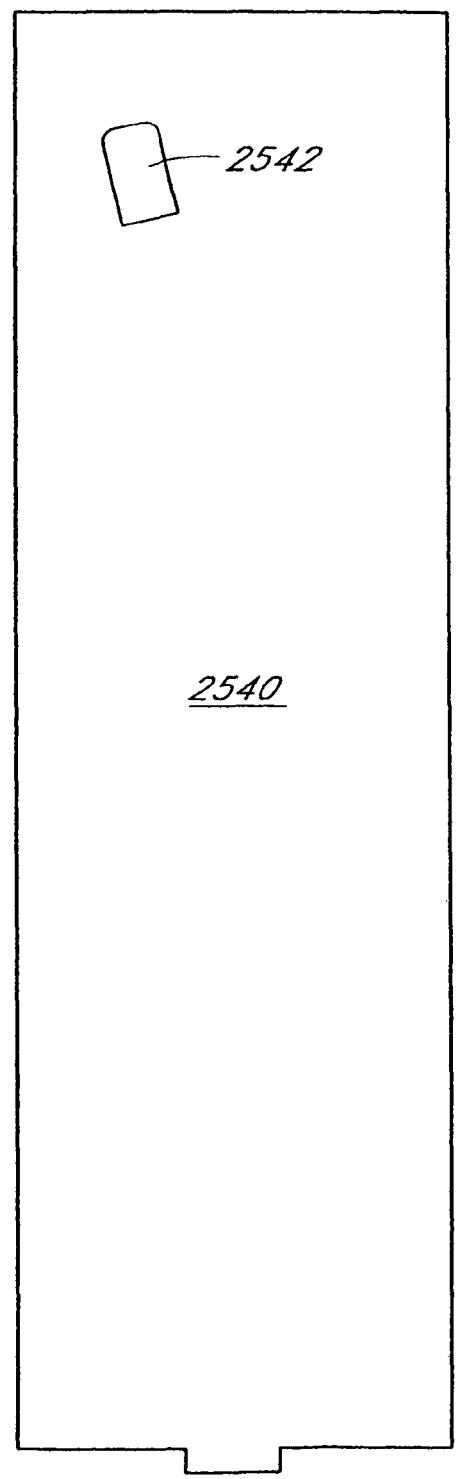

FIGS. 52A and 52B illustrate a base tape 2530 and the top tape 2540. The base tape 2530 has a detector component window 2532 and an emitter component window 2534. Advantageously, the component windows form apertures through the base tape 2530. Therefore, in one preferred embodiment, clear (i.e., transparent to the emitter wavelengths) window material portions 2536, 2538 are provided as a cover to the component windows 2532, 2534. In one embodiment, the clear window material is made from the 3M, Med 3044 described above. The MED 3044 is attached to the back-side (with reference to the illustration in FIG. 52A) of the base tape 2530 in order to provide adhesion to the tissue material under test. Alternatively, the window material 2536, 2538 is non-adhesive, and can be mounted to the up-side (with reference to the illustration in FIG. 53A) of the base tape.

In the present embodiment, the base tape 2530 is formed of a laminate formed of a first layer of non-woven face stock, such as that made by 3M as part number 9908, and a second film, such as single-sided PSA film sold by Coating Sciences, Inc. as P-341. The face stock has PSA on one side. In the illustration of FIG. 52A, the PSA for the face stock is up. The second film of material is laminated to the first layer of non-woven face stock. In the present embodiment, the second layer also has one side with PSA. In the illustration of FIG. 52A, the PSA side of the second film is up. Accordingly, the side of the base tape 2530 depicted in FIG. 52A has PSA from the second film. In the present embodiment, the second film comprises a 1 Mil layer of Coating Sciences part number P-341. The use of two layers provides improved isolation to the flex circuit.

FIG. 52B illustrates the top tape 2540, which is also formed of the two layers of material as with the base tape. In the illustration of FIG. 52B, the adhesive side of the top tape is down and the face stock side of the top tape 2540 is up. For the present embodiment, the top tape has a cutout 2542 for the cover 2510 to the optical cavity 2508. The optical cavity 2508 has the same configuration as the optical cavity 2240 FIG. 44.

Figure 55C:
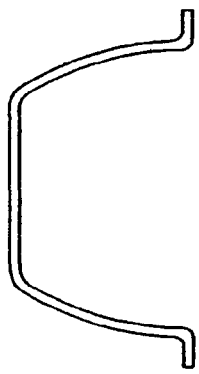
FIGS. 55A-55C depict a cover which is affixed over the optical cavity.
Figure 55A:
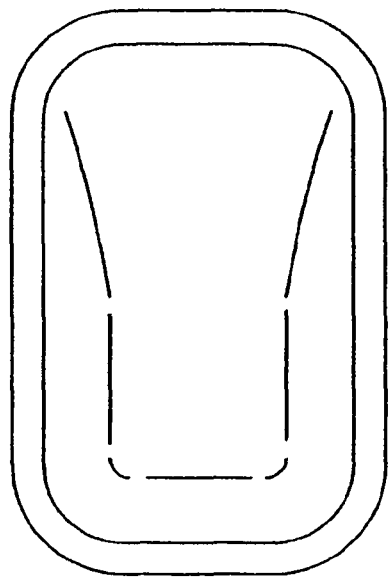
Figure 55B:
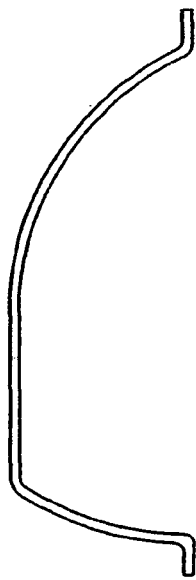

An appropriate cover 2510 is depicted in detail in FIG. 55A-C. The cover is cup-shaped to fit snugly about the optical cavity 2508. FIG. 55A depicts a top view of the optical cover 2510. FIG. 55B depicts a side cross sectional view through B-B in FIG. 55A. FIG. 55C depicts an end cross-sectional view through 55C-55C in FIG. 55A. In the present embodiment, the cover 2510 is vacuum formed from styrene, and is coated with a light absorbing paint, such as black paint to reduce the effects of ambient light.

FIG. 53A illustrates the signal side of an appropriate flex circuit 2506 and FIG. 53B illustrates the back side (i.e., shield side in the this embodiment) of the flex circuit 2506. As depicted in FIG. 54B, the signal side of the flex circuit 2506 has signal traces, the identification resistor 2516, and the two through connections 2518, 2520. The flex circuit also has connection pads 2560, 2562 for the detector 2502 and connection pads 2564, 2556 for the emitter 2504. As with the previous embodiments, the signal side of the flex circuit 2506 has traces formed by etching away the metallic coating. The flex circuit is formed of the same materials as described for the previous embodiments of flex circuits.

FIG. 53B depicts the shield side of the flex circuit 2506. In this embodiment, the flex circuit 2506 is a two-sided circuit, with the shield side coated, substantially in its entirety, with metal, such as copper. By providing a metallic shield side, a separate shielding layer is not needed for the back of the flex circuit 2506. The through connections 2518, 2520 connect the shield side metal to the ground trace 2510.

FIG. 54 illustrates a top shield 2570 for the flex circuit 2506. In the present embodiment, the top shield 2570 is formed from a metallized MYLAR™ as with the shields for the previous embodiment. Prior to application of the top shield 2570, the detector 2502 and the emitter 2504 are soldered to the connection pads 2560, 2562, 2564, 2566. Then one end of a detector shield 2572, having the same configuration as the detector shield 2260 (FIG. 45B) is connected to the shield side of the flex circuit 2506. In one embodiment, the connection is made with solder or conductive PSA.

The top shield 2570 is applied to the signal side of the flex circuit 2506 (with the non-metallized side against the signal side of the flex circuit) with PSA. The detector branch 2574 of the top shield 2570 is longer than a detector branch 2563 of the flex circuit 2506. Thus, the detector branch 2574 is positioned such that the end of the detector branch 2574 covers the detector 2502. Conductive PSA 2576 is applied to the end of the metallized side of the detector branch 2574. The detector shield 2272 is folded over the top shield 2570 and connection is made via the conductive PSA 2576. In this manner, top shield 2570 is coupled to ground via the connection detector shield 2572 which is connected to ground via its connection to the shield side of the flex circuit 2506.

Once the flex circuit assembly 2506 is completed, it is placed on the base tape 2530, with the detector 2502 and the emitter 2504 aligned with the detector window 2532 and the emitter window 2534, respectively. The detector 2502 also is positioned in the rectangular receptacle table of the optical cavity 2508. The optical cavity cover 2510 is then placed over the optical cavity 2508. Finally, the top tape 2540 is placed over the entire assembly with the cut-out for the optical cavity cover aligned with the cover 2510. The entire assembly is pressed to set the PSA adhesive on the base tape 2530 and the top tape 2540. The assembly is then die cut to the shape depicted in FIG. 51.

This embodiment of the probe 2506 has the advantage of fewer assembly steps, and therefore reduced cost. The use of the cover 2510 also allows for further isolation of the detector from ambient light. As discussed above, the cover, as well as the optical cavity, can be made opaque to ambient light, either through coatings or pigmented or otherwise impregnated materials.

Figure 56:
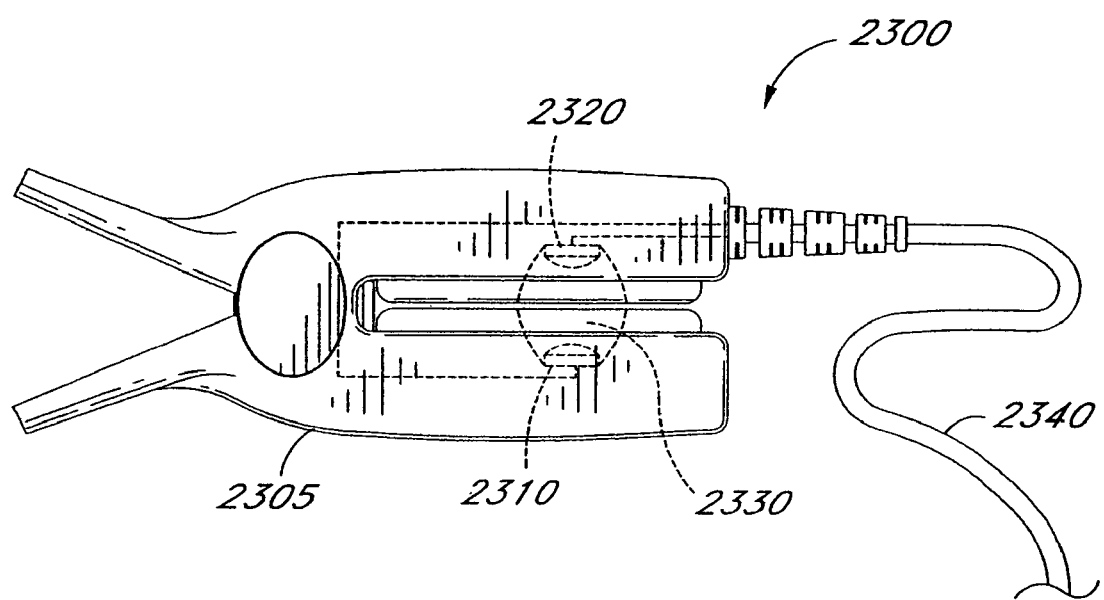
FIG. 56 depicts a clip-on version of the optical probe.

In accordance with another embodiment of the invention, a reusable, low-noise, optical probe 2300 is constructed as depicted in FIG. 56. The probe 2300 comprises a padded, clip-on bracket 2305 which comfortably secures the probe 2300 onto a patient's fingertip (not shown in FIG. 56). The probe further includes a detector 2310 (shown in phantom) which detects optical radiation emitted by an emitter 2320 (also shown in phantom). An aperture 2330, which is substantially similar to the aperture 1020, is formed in the probe 2300 to provide the advantages enumerated above with respect to the aperture 1020. Power to activate the LED 2320, is provided via a connector cable 2340. The cable 2340 also provides a return path for signals output by the detector 2310. Advantageously, the reusable probe 2300 can have a connector with a similar configuration as the connector for the disposable probes, such that the instrument connector can be the same for use with disposable and reusable probes.

The probe of the present invention may be employed in any circumstance where a measurement of transmitted or reflected energy is to be made, including but not limited to measurements taken on a finger, an earlobe, a lip, or a forehead. Thus, there are numerous other embodiments including, but not limited to, changes in the shape of the probe, changes in the materials out of which the probe is made including rigid and resilient materials, and changes in the shape, dimensions, and location of the chamber. Moreover, the chamber(s) may be coated, in whole or in part, with reflective material to help direct energy onto the detector. Furthermore, the probe of the present invention may be employed in measurements of other types of energy. Depending upon the type of energy which is most advantageously utilized in a measurement, the type of transmitter or receiver of energy may be changed. The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A disposable optical probe comprising:
a flex circuit housing a plurality of conductors, at least one emitter and a detector, wherein at least some of the conductors electrically communicate with the at least one emitter and others of the conductors electrically communicate with the detector, wherein the detector is capable of detecting light attenuated by body tissue at a measurement site, and wherein the flex circuit assembly also includes,
first and second branches
a cable connector portion, and
an elongated neck portion electrically and mechanically connecting the first and second branches to the cable connector portion where each of the first and second branches diverges from one end of the elongated neck portion in a generally V-shaped configuration and the cable connector portion terminates the other end, the elongated neck portion being substantially longer than either of the first and second branches, the first branch positioning the at least one emitter and the second branch positioning the detector, the branches cooperating to provide variability in a distance from the at least one emitter to the detector; and
a disposable flexible wrap extending from an end of one of said branches and configured for positioning said assembly with respect to the body tissue and further configured for stabilizing said variability in said distance and materially reducing the effect of light noise on the detector, wherein the disposable flexible wrap is capable of removably attaching said optical probe to the measurement site.

2. The probe according to claim 1, wherein said disposable flexible wrap comprises a soft wrap.

3. The probe according to claim 2, wherein the soft wrap is affixed using a hook-and-loop material.

4. The probe according to claim 2, wherein said soft wrap comprises a POSEY wrap.

5. The probe according to claim 2, wherein the soft wrap includes at least one aperture positioning at least one of the first and second branches.

6. The probe according to claim 1, wherein said measurement site comprises body tissue of one of an adult patient, a pediatric patient, an infant patient, and a neonatal patient.

7. The probe according to claim 6, wherein the tissue comprises one of a forehead, a digit, a heel, and a foot.

8. The probe according to claim 1, wherein said disposable flexible wrap comprises a tape.

9. A method of assembling a noninvasive sensor configured to output signals indicative of light attenuated by body tissue, the method comprising:

acquiring a flex circuit assembly housing a plurality of conductors, ones of said conductors electrically communicating with at least one emitter and others electrically communicate with the detector, the detector capable of detecting light attenuated by body tissue at a measurement site, and wherein the flex circuit assembly also includes first and second branches, a cable connector portion, and an elongated neck portion electrically and mechanically connecting the first and second branches to the cable connector portion where each of the first and second branches diverges from one end of the elongated neck portion in a generally V-shaped configuration and the cable connector portion terminates the other end, the elongated neck portion being substantially longer than either of the first and second branches, the first branch positioning the at least one emitter and the second branch positioning the detector, the branches cooperating to provide variability in a distance from the at least one emitter to the detector; and acquiring a disposable flexible wrap and configuring said wrap to extend from an end of one of said branches;

positioning said assembly with respect to the body tissue using the wrap; and stabilizing said variability in said distance and materially reducing the effect of light noise on the detector, wherein the disposable flexible wrap is capable of removably attaching said optical probe to the measurement site.

10. The method according to claim 9, wherein said disposable flexible wrap comprises a soft wrap.

11. The method according to claim 10, wherein the soft wrap is removably attachable using a hook-and-loop material.

12. The method according to claim 10, wherein said soft wrap comprises a POSEY wrap.

13. The method according to claim 10, wherein the soft wrap includes at least one aperture positioning at least one of the first and second branches.

14. The method according to claim 9, wherein said measurement site comprises body tissue of one of an adult patient, a pediatric patient, an infant patient, and a neonatal patient.

15. The method according to claim 14, wherein the tissue comprises one of a forehead, a digit, a heel, and a foot.

16. The method according to claim 9, wherein said disposable flexible wrap comprises a tape.

* * * * *

UNITED STATES PATENT AND TRADEMARK OFFICE
CERTIFICATE OF CORRECTION

| | |
|---|---|
| PATENT NO. | : 8,670,814 B2 |
| APPLICATION NO. | : 12/360828 |
| DATED | : March 11, 2014 |
| INVENTOR(S) | : Diab et al. |

It is certified that error appears in the above-identified patent and that said Letters Patent is hereby corrected as shown below:

In the specification:

In column 3 at line 29, Change "as," to --as--.

In column 3 at line 59, Change "a an" to --an--.

In column 6 at line 18, Change "the a" to --the--.

In column 7 at line 10, Change "$\epsilon_1$" to --$\epsilon_i$--.

In column 16 at line 21, Change "5" to --50--.

In column 20 at line 50, Change "fixotropic" to --thixotropic--.

In column 33 at line 16, Change "MYLAR™" to --MYLAR™,--.

In the claims:

In column 34 at line 31, In Claim 1, change "A disposable optical" to --An optical--.

In column 34 at line 32, In Claim 1, change "circuit housing" to --circuit assembly housing--.

In column 34 at line 40, In Claim 1, change "branches" to --branches,--.

In column 35 at line 17, In Claim 9, change "communicate with the" to --communicating with a--.

Signed and Sealed this
Twenty-first Day of October, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,670,814 B2 | Page 1 of 1 |
| APPLICATION NO. | : 12/360828 | |
| DATED | : March 11, 2014 | |
| INVENTOR(S) | : Diab et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 681 days.

Signed and Sealed this
Eleventh Day of August, 2015

Michelle K. Lee
*Director of the United States Patent and Trademark Office*